US012734253B2

(12) United States Patent
Karve et al.

(10) Patent No.: US 12,734,253 B2
(45) Date of Patent: Sep. 15, 2026

(54) PROCESSES OF PREPARING mRNA-LOADED LIPID NANOPARTICLES

(71) Applicant: Translate Bio, Inc., Lexington, MA (US)

(72) Inventors: Shrirang Karve, Lexington, MA (US); Ashish Sarode, Lexington, MA (US); Frank DeRosa, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 147 days.

(21) Appl. No.: 18/602,227

(22) Filed: Mar. 12, 2024

(65) Prior Publication Data

US 2024/0366798 A1 Nov. 7, 2024

Related U.S. Application Data

(62) Division of application No. 17/185,587, filed on Feb. 25, 2021, now Pat. No. 11,969,480.

(60) Provisional application No. 62/981,425, filed on Feb. 25, 2020.

(51) Int. Cl.

| | |
|---|---|
| ***C07H 21/02*** | (2006.01) |
| ***A61K 9/51*** | (2006.01) |
| ***A61K 47/60*** | (2017.01) |
| ***A61K 47/69*** | (2017.01) |
| ***A61K 48/00*** | (2006.01) |
| ***B01F 23/451*** | (2022.01) |
| ***B01F 33/301*** | (2022.01) |
| ***B01J 13/20*** | (2006.01) |
| *B01F 101/22* | (2022.01) |

(52) U.S. Cl.

CPC ........ *A61K 48/0091* (2013.01); *A61K 9/5123* (2013.01); *A61K 47/60* (2017.08); *A61K 47/6925* (2017.08); *A61K 48/0033* (2013.01); *B01F 23/451* (2022.01); *B01F 33/3017* (2022.01); *B01J 13/203* (2013.01); *B01F 2101/22* (2022.01)

(58) Field of Classification Search

CPC ............................ A61K 31/7105; C12N 15/67

See application file for complete search history.

(56) References Cited

U.S. PATENT DOCUMENTS

| | | | |
|---|---|---|---|
| 4,857,319 | A | 8/1989 | Crowe et al. |
| 5,049,392 | A | 9/1991 | Weiner et al. |
| 7,094,423 | B1 | 8/2006 | Maurer et al. |
| 9,512,073 | B2 | 12/2016 | Dong et al. |
| 2014/0206753 | A1 | 7/2014 | Guild et al. |
| 2015/0110857 | A1 | 4/2015 | Derosa et al. |

FOREIGN PATENT DOCUMENTS

| | | | | |
|---|---|---|---|---|
| EP | 3020701 | A1 | 5/2016 | |
| EP | 3315125 | A1 * | 5/2018 | ............ A61K 38/00 |
| JP | 2014-534220 | A | 12/2014 | |
| WO | WO 1993/003709 | A1 | 3/1993 | |
| WO | WO 2001/05373 | A1 | 1/2001 | |
| WO | WO 2015/128030 | A1 | 9/2015 | |
| WO | WO 2018/089801 | A1 | 5/2018 | |
| WO | WO 2018/089846 | A1 | 5/2018 | |
| WO | WO 2019/207060 | A1 | 10/2019 | |
| WO | WO 2019/222277 | A1 | 11/2019 | |
| WO | WO 2019/232103 | A1 | 12/2019 | |
| WO | WO 2020/023533 | A1 | 1/2020 | |

OTHER PUBLICATIONS

Winter et al. (Journal of Nanoscience and Nanotechnology, vol. 16, 1321-1330, 2016).*

U.S. Appl. No. 17/185,587, filed Feb. 25, 2021, 2021/0275689, Sep. 9, 2021, U.S. Pat. No. 11,969,480, Apr. 30, 2024, Shrirang Karve, Processes of Preparing MRNA-Loaded Lipid Nanoparticles.

Alton et al., "A randomised, double-blind, placebo-controlled trial of repeated nebulisation of non-viral cystic fibrosis transmembrane conductance regulator (CFTR) gene therapy in patients with cystic fibrosis", NIHR Journals Library, Jul. 2016, 3.5.

Avnir et al., "Amphipathic weak acid glucocorticoid prodrugs remote-loaded into sterically stabilized nanoliposomes evaluated in arthritic rats and in a Beagle dog: a novel approach to treating autoimmune arthritis", Arthritis Rheum., Jan. 2008, 58(1): 119-129.

Ball et al., "Lipid Nanoparticle Formulations for Enhanced Co-delivery of siRNA and mRNA", Nano Lett., Jun. 13, 2018, 18(6): 3814-3822. Epub May 8, 2018.

Belliveau et al., "Microfluidic Synthesis of Highly Potent Limit-size Lipid Nanoparticles for In Vivo Delivery of siRNA", Mol. Ther. Nucleic Acids, Aug. 14, 2012, 1(8): e37.

Buyens et al., "Liposome based systems for systemic siRNA delivery: stability in blood sets the requirements for optimal carrier design", J. Control Release, Mar. 28, 2012, 158(3): 362-370. Epub Oct. 14, 2011.

Fenske et al., "Liposomal nanomedicines", Expert Opin. Drug Deliv., Jan. 2008, 5(1): 25-44.

Fritze et al., "Remote loading of doxorubicin into liposomes driven by a transmembrane phosphate gradient", Biochim. Biophys. Acta., Oct. 2006, 1758: 1633-1640. Epub Jun. 14, 2006.

Gibco, OPTI-MEM I product information, 2001.

Gjetting et al., "A simple protocol for preparation of a liposomal vesicle with encapsulated plasmid DNA that mediate high accumulation and reporter gene activity in tumor tissue", Results Pharma Sci., Sep. 3, 2011, 1(1): 49-56.

Hayes et al., "Genospheres: self-assembling nucleic acid-lipid nanoparticles suitable for targeted gene delivery", Gene Therapy, Apr. 2006, 13(7): 646-651.

(Continued)

*Primary Examiner* — Amy Rose Hudson

(74) *Attorney, Agent, or Firm* — LATHROP GPM LLP; James H. Velema, Esq.

(57) ABSTRACT

The present invention provides an improved process for lipid nanoparticle formulation and mRNA encapsulation. In some embodiments, the present invention provides a process of encapsulating messenger RNA (mRNA) in lipid nanoparticles comprising a step of mixing a suspension of preformed lipid nanoparticles and mRNA.

18 Claims, 19 Drawing Sheets

Specification includes a Sequence Listing.

(56) References Cited

OTHER PUBLICATIONS

Hood et al., "Microfluidic remote loading for rapid single-step liposomal drug preparation", Lab Chip, Sep. 7, 2014, 14(17): 3359-3367.
Jeffs et al., "A scalable, extrusion-free method for efficient liposomal encapsulation of plasmid DNA", Pharm. Res., Mar. 2005, 22(3): 362-372.
Kauffman et al., "Optimization of Lipid Nanoparticle Formulations for mRNA Delivery in Vivo with Fractional Factorial and Definitive Screening Designs", Nano Lett., Nov. 11, 2015, 15(11): 7300-7306. Epub Oct. 20, 2015.
Kubota et al., "Effect of the nanoformulation of siRNA-lipid assemblies on their cellular uptake and immune stimulation", Int. J. Nanomedicine, Jul. 19, 2017, 12: 5121-5133.
Leung et al., "Lipid Nanoparticles Containing siRNA Synthesized by Microfluidic Mixing Exhibit an Electron-Dense Nanostructured Core", J. Phys. Chem., Aug. 30, 2012, 116(34): 18440-18450. Epub Jul. 18, 2012.
Martinon et al., "Induction of virus-specific cytotoxic T lymphocytes in vivo by liposome-entrapped mRNA", Eur. J. Immunol., Jul. 1993, 23(7): 1719-1722.
Maurer et al., "Spontaneous entrapment of polynucleotides upon electrostatic interaction with ethanol-destabilized cationic liposomes", Biophys. J., May 2001, 80(5): 2310-2326.
Rejman et al., "mRNA transfection of cervical carcinoma and mesenchymal stem cells mediated by cationic carriers", J. Control Release, Nov. 1, 2010, 147(3):385-391. Epub Aug. 12, 2010.
Wan et al., "Lipid nanoparticle delivery systems for siRNA-based therapeutics", Drug Deliv. Transl. Res., Feb. 2014, 4(1): 74-83.
Wang et al., "Bone-Targeted 2,6,9-Trisubstituted Purines: Novel Inhibitors of Src Tyrosine Kinase for the Treatment of Bone Diseases", Bioorg. Med. Chem. Lett., Sep. 14, 2003, 13(18): 3067-3070.
Wang et al., "Encapsulating protein into preformed liposomes by ethanol-destabilized method", Artif. Cells Blood Substit. Immobil. Biotechnol., Aug. 2003, 31(3): 303-312.
Wang et al., "Systemic delivery of modified mRNA encoding herpes simplex virus 1 thymidine kinase for targeted cancer gene therapy", Mol. Ther., Feb. 2013, 21(2): 358-367. Epub Dec. 11, 2012.
Heyes et al., "Cationic lipid saturation influences intracellular delivery of encapsulated nucleic acids", Journal of Controlled Release, Oct. 3, 2005, 107(2): 276-287.

* cited by examiner

Stepwise Step Down Remix
N / P
Formulation process time
Stepwise Step Up Remix
N / P
Formulation process time
Continuous Step Down Remix
N / P
Formulation process time
Continuous Step Up Remix
N / P
Formulation process time
Step Up-Down Remix
N / P
Formulation process time
Step Down-Up Remix
N / P
Formulation process time Day
1
Dose
MRT
2
Dose
$NH_4Cl$
40 min
Plasma
$NH_3$
OTC Protein
ng OTC/mg protein
2500
2000
1500
1000
500
0
WT-saline
OTC-saline
0.2 mg/kg
0.4 mg/kg
0.6 mg/kg
0.8 mg/kg
1.0 mg/kg
Dose
Plasma $NH_3$
$NH_3$ (µmol/L)
2500
2000
1500
1000
500
0
WT-saline
OTC-saline
0.2 mg/kg
0.4 mg/kg
0.6 mg/kg
0.8 mg/kg
1.0 mg/kg
Dose

PROCESSES OF PREPARING mRNA-LOADED LIPID NANOPARTICLES

CROSS-REFERENCE TO RELATED APPLICATIONS

This application is a division of U.S. patent application Ser. No. 17/185,587, filed Feb. 25, 2021, which claims priority to U.S. Provisional Patent Application Ser. No. 62/981,425, filed Feb. 25, 2020, which are hereby incorporated by reference in their entirety for all purposes.

SEQUENCE LISTING

The instant application contains a Sequence Listing which has been submitted electronically in XML format and is hereby incorporated by reference in its entirety. Said XML file, created on Mar. 11, 2024, is named 752920_SA9-865DV_ST26.xml and is 19,913 bytes in size.

BACKGROUND

Messenger RNA therapy (MRT) is becoming an increasingly important approach for the treatment of a variety of diseases. MRT involves administration of messenger RNA (mRNA) to a patient in need of the therapy for production of the protein encoded by the mRNA within the patient's body. Lipid nanoparticles are commonly used to encapsulate mRNA for efficient in vivo delivery of mRNA.

To improve lipid nanoparticle delivery, much effort has focused on identifying novel lipids or particular lipid compositions that can affect intracellular delivery and/or expression of mRNA, e.g., in various types of mammalian tissue, organs and/or cells (e.g., mammalian liver cells). However, these approaches are costly, time consuming and unpredictable.

SUMMARY OF INVENTION

The present invention provides, among other things, an improved process for preparing mRNA-loaded lipid nanoparticles. In particular, the present invention is based on the surprising discovery that alteration of the N/P ratio during the loading of preformed lipid nanoparticles with mRNA as shown in FIG. 1 results in formulated lipid nanoparticles that exhibit unexpectedly efficient in vivo delivery of the mRNA and surprisingly potent expression of protein(s), polypeptide(s) and/or peptide(s) that the mRNA encodes.

As compared to conventional processes, the inventive process can therefore be employed to shift the therapeutic index of the resulting lipid nanoparticles in a positive direction. The associated advantages may include lower cost, better patient compliance, and more patient-friendly dosing regimens. The inventive process also results in efficient encapsulation and homogeneous particle sizes. Without wishing to be bound by any particular theory, the inventive process is particularly useful for preparing lipid nanoparticle compositions for systemic delivery, where exceptionally efficient in vivo delivery of mRNA to target cells and expression of the mRNA-encoded protein has been observed. In some embodiments, the systemic delivery comprises delivery to the liver and particularly to hepatocytes.

This inventive process can be performed using a pump system and is therefore scalable, allowing for improved particle formation/formulation in amounts sufficient for, e.g., performance of clinical trials and/or commercial sale.

In a first aspect, the invention provides a process of encapsulating messenger RNA (mRNA) in preformed empty lipid nanoparticles (LNPs), wherein the lipid component of the LNPs comprises or consists of a cationic lipid, a non-cationic lipid, a PEG-modified lipid, and optionally cholesterol and said process comprises the steps of (a) adding a first volume of a solution comprising the mRNA to a suspension comprising the preformed empty LNPs such that a mixture comprising LNPs encapsulating the mRNA is formed; and (b) adding one or more additional volumes of the solution comprising the mRNA to the mixture obtained in the preceding step until a desired molar ratio of cationic lipid to mRNA is achieved.

In some embodiments, the addition of the first volume of the solution comprising the mRNA results in an at least 10-fold molar excess of cationic lipid to mRNA. In some embodiments, the addition of the first volume of the solution comprising the mRNA results in an at least 15-fold molar excess of cationic lipid to mRNA. In some embodiments, the addition of the first volume of the solution comprising the mRNA results in a molar ratio of about 10-20 (cationic lipid) to 1 (mRNA). In some embodiments, the addition of the first volume of the solution comprising the mRNA results in a molar ratio of about 16 (cationic lipid) to 1 (mRNA).

In some embodiments, the first volume and the one or more additional volumes of the solution comprising the mRNA are of equal volume.

In some embodiments, the one or more additional volumes are no more than four volumes or no more than eight volumes. In some embodiments, the one or more additional volumes are one, two, three, four, five, six, seven, or eight additional volumes.

In some embodiments, a period of mixing occurs before addition of each of the one or more additional volumes of the solution comprising the mRNA. In some embodiments, each period is equal in length. In some embodiments, each period does not exceed 5 minutes. In some embodiments, each period is about 3-5 minutes. In some embodiments, each period is about 4 minutes.

In some embodiments, the addition of the final volume of the one or more additional volumes is followed by a further period of mixing. In some embodiments, the further period is equal in length to each of the preceding periods. In other embodiments, the further period exceeds the length of each of the preceding periods. In some embodiments, said further period is at least 1.5- to 2-fold longer than each of the preceding periods of time.

In some embodiments, the first volume and the one or more additional volumes of the solution comprising the mRNA are added continuously. In some embodiments, the continuous addition of the solution comprising the mRNA takes place over a period not exceeding 20 minutes. In some embodiments, the continuous addition of the solution comprising the mRNA occurs at a constant flow rate. In some embodiments, the continuous addition of the solution comprising the mRNA occurs at a flow rate that increases or decreases over time. In some embodiments, the period of continuous addition of the solution comprising the mRNA is followed by a period of mixing. In some embodiments, the period of continuous addition and the period of mixing following continuous addition do not exceed 20 minutes.

In a second aspect, the invention provides a process of encapsulating messenger RNA (mRNA) in preformed empty lipid nanoparticles (LNPs), wherein the lipid component of the LNPs comprises or consists of a cationic lipid, a non-cationic lipid, a PEG-modified lipid, and optionally cholesterol and said process comprises the steps of (a) adding a first volume of a suspension comprising the preformed empty LNPs to a solution comprising the mRNA such that a mixture comprising LNPs encapsulating the mRNA is formed; and (b) adding one or more additional volumes of the suspension comprising the preformed empty LNPs to the mixture obtained in the preceding step until a desired molar ratio of cationic lipid to mRNA is achieved.

In some embodiments, the addition of the first volume of the suspension comprising the preformed empty LNPs results in an approximately equimolar ratio of cationic lipid to mRNA. In some embodiments, the addition of the one or more additional volumes of the suspension comprising the preformed empty LNPs results in a molar excess of cationic lipid to mRNA. In some embodiments, the addition of the one or more additional volumes of the suspension comprising the preformed empty LNPs results in an approximately 2- to 4-fold molar excess of cationic lipid to mRNA.

In some embodiments, the first volume and the one more additional volumes of the suspension comprising the preformed empty LNPs are of equal volume.

In some embodiments, the one or more additional volumes are no more than four volumes or no more than eight volumes. In some embodiments, the one or more additional volumes are one, two, three, four, five, six, seven, or eight additional volumes.

In some embodiments, a period of mixing occurs before addition of each of the one or more additional volumes of the suspension comprising the preformed empty LNPs. In some embodiments, each period is equal in length. In some embodiments, the period does not exceed 5 minutes. In some embodiments, the period is about 3-5 minutes. In some embodiments, the period is about 4 minutes.

In some embodiments, the addition of the final volume of one or more additional volumes is followed by a further period of time of mixing. In some embodiments, the further period of mixing is equal in length to each of the preceding periods. In other embodiments, the further period of time exceeds the length of each of the preceding periods. In some embodiments, said further period of time is at least 1.5- to 2-fold longer than each of the preceding periods.

In some embodiments, the first volume and the one or more additional volumes of the suspension comprising the preformed empty LNPs are added continuously. In some embodiments, the continuous addition of the suspension comprising the preformed empty LNPs takes place over a period of time not exceeding 20 minutes. In some embodiments, the continuous addition of the suspension comprising the preformed empty LNPs occurs at a constant flow rate. In some embodiments, the continuous addition of the suspension comprising the preformed empty LNPs occurs at a flow rate that increases or decreases over time. In some embodiments, the period of continuous addition of the suspension comprising the preformed empty LNPs is followed by a period of mixing. In some embodiments, the period of continuous addition and the period of mixing following continuous addition do not exceed 20 minutes.

In these aspects of the invention, the suspension comprising the preformed empty LNPs may be at about 60° C. to about 70° C. and the solution comprising the mRNA may be at ambient temperature. In some embodiments, the wherein the suspension comprising the preformed empty LNPs is at about 65° C. In some embodiments, mixing comprises heating the combined mixture of LNPs and mRNA to between about 60° C. and about 70° C. In some embodiments, mixing comprises heating the combined mixture of LNPs and mRNA to about 65° C.

In these aspects of the invention, the desired molar ratio may be about 3-5 (cationic lipid) to 1 (mRNA). In some embodiments, the desired molar ratio is about 4 (cationic lipid) to 1 (mRNA).

In these aspects of the invention, the empty LNPs may be formed by mixing a lipid solution with an aqueous solution, wherein the lipid solution comprises a cationic lipid, a non-cationic lipid, and a PEG-modified lipid dissolved in ethanol. In some embodiments, the aqueous solution comprises citrate. In some embodiments, ethanol and/or citrate is/are removed by tangential flow filtration to form the solution comprising the empty LNPs.

In any of these aspects of the invention, greater than about 90% of the preformed empty LNPs have a size ranging from 75-150 nm. Typically, the processes described in the first and second aspects of the invention results in LNPs encapsulating the mRNA of which greater than about 90% have a size that is at least about 5% (e.g., at least about 10%) larger in size than the preformed empty LNPs. The mRNA encapsulation percentage is typically greater than about 80%, e.g., greater than about 90%.

In any of these aspects of the invention, the preformed empty LNPs and mRNA may be mixed using a pump system. In some embodiments, the pump system comprises a pulse-less flow pump, e.g., a gear pump or a centrifugal pump.

The processes described in the first and second aspects of the invention can be used to prepare a composition of lipid nanoparticles (LNPs) encapsulating mRNA, wherein the average size of LNPs is between 5% and 10% larger than LNPs that have been prepared by mixing preformed empty LNPs with mRNA without altering the molar ratio of cationic lipid to mRNA during encapsulation. In some embodiments, the nanoparticles have a size from about 75 nm to 150 nm. In some embodiments, the nanoparticles comprise a PDI from about less than 0.25 to less than 0.16.

A composition comprising the LNPs encapsulating mRNA prepared by the processes of the first and second aspects of the invention find use in methods of treating a subject suffering from a deficiency of a peptide, polypeptide or protein, wherein said methods comprise administering to the subject the composition and the mRNA encodes the peptide, polypeptide or protein. In some embodiments, the peptide, polypeptide or protein is selected from spinal motor neuron 1 (SMN), alpha-galactosidase (GLA), argininosuccinate synthetase (ASS1), ornithine transcarbamylase (OTC), Factor IX (FIX), phenylalanine hydroxylase (PAH), erythropoietin (EPO), cystic fibrosis transmembrane conductance receptor (CFTR).

A composition comprising the LNPs encapsulating mRNA prepared by the processes of the first and second aspects of the invention find use in methods of delivering mRNA for in vivo protein production. Such methods comprise administering into a subject a said composition. The mRNA typically encodes a protein of interest.

In a third aspect, the invention provides a method of manufacturing a lipid nanoparticle (LNP) composition, wherein the method comprises: (a) mixing a first set of preformed empty lipid nanoparticles (LNPs) comprising a first cationic lipid, a first non-cationic lipid, a first PEG-modified lipid, and optionally cholesterol with mRNA under conditions that allow encapsulation of the mRNA; (b) combining the mRNA-encapsulating LNPs formed in step (a) with a second set of preformed empty LNPs comprising a second cationic lipid, a second non-cationic lipid, a second PEG-modified lipid, and optionally cholesterol, resulting in the LNP composition. Typically, the mRNA encodes a peptide, polypeptide or protein.

In some embodiments, the first set of preformed empty LNPs and the second set of preformed empty LNPs have the same lipid formulation. In some embodiments, the first set of preformed empty LNPs and the second set of preformed empty LNPs have different lipid formulations. In some embodiments, the first cationic lipid and the second cationic lipid are different. In some embodiments, the first non-cationic lipid and the second non-cationic lipid are different. In some embodiments, the first cationic lipid and the second cationic lipid are the same and the first non-cationic lipid and the second non-cationic lipid are different. In some embodiments, the first non-cationic lipid is DOPE and the second non-cationic lipid is DEPE or the first non-cationic lipid is DEPE and the second non-cationic lipid is DOPE.

In some embodiments, the method further comprises a step of first mixing (i) the first cationic lipid, the first non-cationic lipid, the first PEG-modified lipid, and optionally cholesterol to form the first set of preformed empty LNPs prior to step (a) and/or (ii) the second cationic lipid, the second non-cationic lipid, the second PEG-modified lipid, and optionally cholesterol to form the second set of preformed empty LNPs prior to step (b).

In some embodiments, the mRNA-encapsulating LNPs and the second set of preformed empty LNPs are combined at a ratio ranging from 20:1 to 1:20, from 10:1 to 1:10, from 5:1 to 1:5, from 3:1 to 1:3, or from 2:1 to 1:2. In some embodiments, the mRNA-encapsulating LNPs and the second set of preformed empty LNPs are combined at a ratio of or greater than 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, or 1:20.

In some embodiments, the mRNA-encapsulating LNPs and the preformed empty LNPs in the first and second sets each have an average size ranging from about 75-150 nm in diameter. In some embodiments, the mRNA-encapsulating LNPs and the preformed empty LNPs in the first and second sets each have an average size of less than 100 nm in diameter.

In some embodiments, the composition has a ratio of total lipids to total mRNA ranging from 20:1 to 1:1, from 10:1 to 1:1, from 5:1 to 1:1, from 5:1 to 2:1, or from 4:1 to 2:1, or greater than 1:1, 2:1, 3:1, 4:1, 5:1, 6:1, 7:1, 8:1, 9:1, 10:1, 12:1, 15:1, or 20:1.

In a fourth aspect, the invention relates to a composition comprising a first set of mRNA-encapsulating lipid nanoparticles (LNPs) comprising a first cationic lipid, a first non-cationic lipid, a first PEG-modified lipid, and optionally cholesterol and a second set of empty LNPs comprising a second cationic lipid, a second non-cationic lipid, a second PEG-modified lipid, and optionally cholesterol, wherein the first set of LNPs and the second set of LNPs are present at a ratio ranging from 20:1 to 1:20, from 10:1 to 1:10, from 5:1 to 1:5, from 3:1 to 1:3, or from 2:1 to 1:2. Typically, the mRNA encodes a peptide, polypeptide or protein.

In some embodiments, the first set of LNPs and the second set of LNPs have the same lipid formulation. In some embodiments, the first set of LNPs and the second set of LNPs have different lipid formulations. In some embodiments, the first cationic lipid and the second cationic lipid are different between the first set of LNPs and the second set of LNPs. In some embodiments, the first non-cationic lipid and the second non-cationic lipid are different between the first set of LNPs and the second set of LNPs. In some embodiments, the first cationic lipid and the second cationic lipid are the same and the first non-cationic lipid and the second non-cationic lipid are different between the first set of LNPs and the second set of LNPs. In some embodiments, the first non-cationic lipid is DOPE and the second non-cationic lipid is DEPE or wherein the first non-cationic lipid is DEPE and the second non-cationic lipid is DOPE.

In some embodiments, the first set of LNPs and the second set of LNPs each have an average size ranging from about 75-150 nm in diameter. In some embodiments, the first set of LNPs and the second set of LNPs each have an average size of less than 100 nm in diameter.

A composition of the third and fourth aspects of the invention finds use in methods of treating a deficiency in a peptide, polypeptide or protein in a subject, wherein the method comprises administering to the subject the compositions, wherein the mRNA encodes the peptide, polypeptide or protein deficient in the subject. In some embodiments, the expression level of the peptide, polypeptide or protein encoded by the mRNA following administration of the composition to the subject is increased as compared to the expression level of the peptide, polypeptide or protein encoded by the same amount of mRNA administered with identical mRNA-encapsulating LNPs but without the second set of empty LNPs, with comparable expression levels of liver enzyme aspartate transaminase (AST) and/or alanine aminotransferase (ALT). In particular embodiments, the expression level of the protein, polypeptide, or peptide is increased by at least 20%, 40%, 50%, 60%, 70%, 80%, 90%, 1-fold, 1.5-fold, 2-fold, 3-fold, 4-fold, or 5-fold.

In a fifth aspect, the invention provides a method of encapsulating messenger RNA (mRNA) into preformed empty lipid nanoparticles (LNPs) by mixing a first fluid comprising preformed empty LNPs and a second fluid comprising mRNA, wherein the lipid component of the LNPs comprises a cationic lipid, the method comprising: (a) mixing, for a first time period, the first fluid at a flow rate $n_1$ with a first portion of the second fluid at a flow rate $n_2$ to produce a mixed fluid having a first molar ratio of cationic lipid to mRNA; (b) mixing, for a second time period, the mixed fluid at a flow rate greater than $n_1$ and a second portion of the second fluid at flow rate $n_2$, such that the molar ratio of cationic lipid to mRNA of the resulting mixed fluid is at least 20% lower than the first molar ratio; and (c) repeating step (b) by increasing the flow rate of the resulting mixed fluid with each repeat until a desired molar ratio of cationic lipid to mRNA is reached. In some embodiments, step (b) is repeated no more than four times, e.g. three times or twice.

In some embodiments, the desired molar ratio of cationic lipid to mRNA is 3-5 (cationic lipid):1 (mRNA). In some embodiments, the desired molar ratio of cationic lipid to mRNA is about 4:1.

In some embodiments, the first molar ratio of cationic lipid to mRNA is between 30:1 and 10:1, e.g., about 16:1. In some embodiments, the molar ratio of cationic lipid to mRNA after step (b) has been performed once is between 24:1 and 8:1, e.g., about 12:1. In some embodiments, the molar ratio of cationic lipid to mRNA after step (b) has been repeated once is between 20:1 and 6:1, e.g., about 8:1. In some embodiments, the molar ratio of cationic lipid to mRNA after step (b) has been repeated twice is between 16:1 and 4:1, e.g. about 4:1.

In some embodiments, mixing in any step comprises: pumping the first fluid to a mixing junction; and pumping a portion of the second fluid to the mixing junction, optionally wherein the mixing junction is a T-junction. In some embodiments, mixing in step (a) comprises mixing the first fluid and first portion of the second fluid for a first portion of the first time period; and storing, in an intermediary vessel, the mixed fluid for a second portion of the first time period. In some embodiments, mixing in step (b) comprises: (i) mixing the mixed fluid and second portion of the second fluid for a first portion of the second time period; and (ii) storing, in an, or the, intermediary vessel, the mixed fluid result of step (b)(i) for a second portion of the second time period.

In some embodiments a method in accordance with the fifth aspect of the invention further comprises: storing the product of step (b) or (c) in a final vessel. In some embodiments, the method further comprises: heating the product of step (a), (b), and/or (c) before the product is stored in an, or the, intermediary vessel or further mixed, optionally wherein the product of step (a), (b), and/or (c) is heated to a temperature between 60° C. and 70° C., e.g., between 63° C. and 67° C., e.g., about 65° C. In such embodiments, the method may further comprise: cooling the product of step (b) or (c) before storing it in the final vessel, optionally wherein the product of step (b) or (c) is cooled to a temperature of between 19° C. and 23° C., e.g. between 20° C. and 22° C., e.g. about 21° C.

In a sixth aspect, the invention provides a method of encapsulating messenger RNA (mRNA) into preformed empty lipid nanoparticles (LNPs) by mixing a first fluid comprising preformed empty LNPs and a second fluid comprising mRNA, wherein the lipid component of the LNPs comprises a cationic lipid, the method comprising: (a) mixing, for a first time period, a first portion of the first fluid at a flow rate $n_1$ with the second fluid at a flow rate $n_2$ to produce a mixed fluid having a first molar ratio of cationic lipid to mRNA; (b) mixing, for a second time period, the mixed fluid at a flow rate greater than $n_1$ and a second portion of the first fluid at flow rate $n_2$, such that the molar ratio of cationic lipid to mRNA of the resulting mixed fluid is at least 20% greater than the first molar ratio; and (c) repeating step (b) by increasing the flow rate of the resulting mixed fluid with each repeat until a desired molar ratio of cationic lipid to mRNA is reached. In some embodiments, step (b) is repeated no more than four times, e.g. three times or twice.

In some embodiments, the desired molar ratio of cationic lipid to mRNA is 3-5 (cationic lipid):1 (mRNA). In some embodiments, the desired molar ratio of cationic lipid to mRNA is about 4:1.

In some embodiments, the first molar ratio of cationic lipid to mRNA is between 1:10 and 1:1, e.g., about 1:1. In some embodiments, the molar ratio of cationic lipid to mRNA after step (b) has been performed once is between 1:5 and 2:1, e.g., about 2:1. In some embodiments, the molar ratio of cationic lipid to mRNA after step (b) has been repeated once is between 1:2 and 3:1, e.g., about 3:1. In some embodiments, the molar ratio of cationic lipid to mRNA after step (b) has been repeated twice is between 1:1 and 4:1, e.g., about 4:1.

In some embodiments, mixing in any step comprises: pumping a portion of the first fluid to a mixing junction; and pumping the second fluid to the mixing junction, optionally wherein the mixing junction is a T-junction. In some embodiments, mixing in step (a) comprises: mixing the first portion of the first fluid and the second fluid for a first portion of the first time period; and storing, in an intermediary vessel, the mixed fluid for a second portion of the first time period. In some embodiments, mixing in step (b) comprises: (i) mixing the mixed fluid and second portion of the first fluid for a first portion of the second time period; and (ii) storing, in an, or the, intermediary vessel, the mixed fluid result of step (b)(i) for a second portion of the second time period.

In some embodiments, a method in accordance with the sixth aspect of the invention further comprises: storing the product of step (b) or (c) in a final vessel. In some embodiments, the method further comprises: heating the product of step (a), (b), and/or (c) before the product is stored in an, or the, intermediary vessel or further mixed, optionally wherein the product of step (a), (b), and/or (c) is heated to a temperature between 60° C. and 70° C., e.g., between 63° C. and 67° C., e.g., about 65° C. In such embodiments, the method may further comprise: cooling the product of step (b) or (c) before storing it in the final vessel, optionally wherein the product of step (b) or (c) is cooled to a temperature of between 19° C. and 23° C., e.g. between 20° C. and 22° C., e.g. about 21° C.

The following embodiments may apply to a method in accordance with the fifth or sixth aspect of the invention. In some embodiments, the first time period does not exceed 5 minutes. In some embodiments, the second time period does not exceed 5 minutes. In some embodiments, the first portion of the first time period does not exceed 2 minutes, e.g. the first time period is about 1 minute. In some embodiments, the first portion of the second time period does not exceed 2 minutes, e.g. the second time period is about 1 minute.

In some embodiments, $n_1$ and $n_2$ are within the range of 20 mL/min to 20 L/min. In some embodiments, the first fluid has a volume of between 40 mL and 100 L. In some embodiments, the second fluid has a volume of 40 mL and 100 L. In some embodiments, the mRNA in the second fluid has a concentration of between 0.01 mg/mL and 5 mg/mL.

In some embodiments, the first fluid is a suspension of preformed empty LNPs. In some embodiments, the second fluid is a solution of mRNA in water for injection.

In a seventh aspect, the invention provides an apparatus for encapsulating messenger RNA (mRNA) into preformed empty lipid nanoparticles (LNPs) by mixing a first fluid comprising preformed empty LNPs and a second fluid comprising mRNA, the apparatus comprising: a first pump; a second pump; a mixing junction; an intermediary vessel; a first heat exchanger; an arrangement of LNP conduits, configured to direct the first fluid to the mixing junction via the first pump; an arrangement of mRNA conduits, configured to direct the second fluid to the mixing junction via the second pump, wherein the first and second fluids form a mixed fluid at the mixing junction; a recycle loop, configured to: direct the mixed fluid from the mixing junction to the first heat exchanger, and from the first heat exchanger to the intermediary vessel, and wherein the recycle loop is configurable to direct the mixed fluid from the intermediary vessel to: the arrangement of LNP conduits upstream of the first pump; or the arrangement of mRNA conduits upstream of the second pump.

In an eighth aspect, the invention provides an apparatus for encapsulating messenger RNA (mRNA) into preformed empty lipid nanoparticles (LNPs) by mixing a first fluid comprising preformed empty LNPs and a second fluid comprising mRNA, the apparatus comprising: a first pump; a second pump; a source of the first fluid; a source of the second fluid; a mixing junction; an arrangement of LNP conduits, configured to direct the first fluid from the source of first fluid to the mixing junction via the first pump; an arrangement of mRNA conduits, configured to direct the second fluid from the source of second fluid to the mixing junction via the second pump, wherein the first and second fluids form a mixed fluid at the mixing junction; a recycle loop, configurable to direct the mixed fluid to: the arrangement of LNP conduits upstream of the first pump; or the arrangement of mRNA conduits upstream of the second pump.

In some embodiments, the recycle loop is configured to direct the mixed fluid to the first arrangement of conduits upstream of the first pump. In some embodiments, the recycle loop is configured to direct the mixed fluid to the second arrangement of conduits upstream of the second pump.

In some embodiments, the first pump is configured to pump the first fluid at a flow rate $n_1$, and the second pump is configured to pump the second fluid at a flow rate $n_2$, wherein $n_1$ is greater than $n_2$. In some embodiments, the first pump is configured to pump the mixed fluid at a flow rate $n_3$, wherein $n_3$ is greater than $n_1$. In some embodiments, the first pump is configured to increase the flow rate of the mixed fluid each time the mixed fluid passes through the recycle loop.

In some embodiments, the first pump is configured to pump the first fluid at a flow rate $m_1$, and the second pump is configured to pump the second fluid at a flow rate $m_2$, wherein $m_2$ is greater than $m_1$. In some embodiments, the second pump is configured to pump the mixed fluid at a flow rate $m_3$, wherein $m_3$ is greater than $m_2$. In some embodiments, the second pump is configured to increase the flow rate of the mixed fluid each time the mixed fluid passes through the recycle loop.

The following embodiments may apply to a method in accordance with the seventh or eighth aspect of the invention. In some embodiments, the recycle loop is further configured to: direct the mixed fluid from the mixing junction to an, or the, intermediary vessel before directing the mixed fluid to the arrangement of LNP conduits or arrangement of mRNA conduits.

In some embodiments, the apparatus further comprises: a first heat exchanger, and wherein the recycle loop is further configured to direct the mixed fluid from the mixing junction to a, or the, first heat exchanger before directing the mixed fluid to the arrangement of LNP conduits or arrangement of mRNA conduits. In some embodiments, the recycle loop is further configured to: direct the mixed fluid to the first heat exchanger before directing the mixed fluid to the intermediary vessel. In some embodiments, the first heat exchanger is configured to heat the mixed fluid to a temperature of between 60° C. and 70° C., e.g., between 63° C. and 67° C., e.g., about 65° C.

In some embodiments, the apparatus further comprises: a first storage vessel, configured to store the first fluid, positioned upstream of the first pump, and in fluid connection with the arrangement of LNP conduits; and a second storage vessel, configured to store the second fluid, positioned upstream of the second pump, and in fluid connection with the arrangement of mRNA conduits. In some embodiments, the first storage vessel is configured to store the first fluid at a temperature between 60° C. and 70° C., e.g., between 63° C. and 67° C., e.g., about 65° C.

In some embodiments, the apparatus further comprises: an output arrangement of conduits, configured to direct the mixed fluid from the mixing junction to a final storage vessel. In some embodiments, the apparatus further comprises: a second heat exchanger, and wherein the output arrangement of conduits is further configured to direct the mixed fluid through the second heat exchanger before directing the mixed fluid to the final storage vessel. In some embodiments, the second heat exchanger is configured to cool the mixed fluid to a temperature of between 19° C. and 23° C., e.g., between 20° C. and 22° C., e.g., about 21° C.

In some embodiments, the first and/or second pump is a pulse-less flow pump, e.g. wherein the first and/or second pump is/are a gear pump or a centrifugal pump.

In some embodiments, the mixing junction is a T-junction.

In a ninth aspect, the invention provides an apparatus for encapsulating messenger RNA (mRNA) into preformed empty lipid nanoparticles (LNPs) by mixing a first fluid comprising preformed empty LNPs and a second fluid comprising mRNA, the apparatus comprising: a first pump; a second pump; a mixing junction; an arrangement of LNP conduits, configured to direct the first fluid to the mixing junction via the first pump; an arrangement of mRNA conduits, configured to direct the second fluid to the mixing junction via the second pump, wherein the first and second fluids form a mixed fluid at the mixing junction; a recycle loop, configured to direct the mixed fluid to: the arrangement of LNP conduits upstream of the first pump; or the arrangement of mRNA conduits upstream of the second pump; and a processor configured to: for a first time period, drive the first pump at a first flow rate and drive the second pump at a second flow rate; and for a second time period, if the recycle loop is configured to direct the mixed fluid to the arrangement of LNP conduits, drive the first pump at n1 times the first flow rate and drive the second pump at the second flow rate; or for a second time period, if the recycle loop is configured to direct the mixed fluid to the arrangement of LNP conduits, drive the first pump at the first flow rate and drive the second pump at $n_1$ times the first flow rate.

In some embodiments, wherein a method has been performed in accordance with the fifth or sixth aspect of the invention using an apparatus in accordance with the seventh, eighth or ninth aspect of the invention, the method further comprises: passing a first stream of RNase-free water through the apparatus; passing a stream of sodium hydroxide solution through the apparatus; and passing a second stream of RNase-free water through the apparatus.

In the various aspects of the invention, the cationic lipid may be selected from the group consisting of cKK-E12, OF-02, C12-200, MC3, DLinDMA, DLinkC2DMA, ICE (Imidazol-based), HGT5000, HGT5001, HGT4003, DODAC, DDAB, DMRIE, DOSPA, DOGS, DODAP, DODMA and DMDMA, DODAC, DLenDMA, DMRIE, CLinDMA, CpLinDMA, DMOBA, DOcarbDAP, DLinDAP, DLincarbDAP, DLinCDAP, KLin-K-DMA, DLin-K-XTC2-DMA, 3-(4-(bis(2-hydroxydodecyl)amino)butyl)-6-(4-((2-hydroxydodecyl)(2-hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione (Target 24), cDD-TE-4-E10, cDD-TE-4-E12, and combinations thereof. In some embodiments, the one or more cationic lipids comprise Target 24. In some embodiments, the one or more cationic lipids comprise ICE. In some embodiments, the one or more cationic lipids comprise cKK-E12. In some embodiments, the one or more cationic lipids comprise cDD-TE-4-E10. In some embodiments, the one or more cationic lipids comprise cDD-TE-4-E12.

In the various aspects of the invention, the non-cationic lipid may be selected from the group consisting of DSPC (1,2-distearoyl-sn-glycero-3-phosphocholine), DPPC (1,2-dipalmitoyl-sn-glycero-3-phosphocholine), DEPE (1,2-dierucoyl-sn-glycero-3-phosphoethanolamine), DOPE (1,2-dioleyl-sn-glycero-3-phosphoethanolamine), DOPC (1,2-dioleyl-sn-glycero-3-phosphotidylcholine) DPPE (1,2- dipalmitoyl-sn-glycero-3-phosphoethanolamine), DMPE (1,2-dimyristoyl-sn-glycero-3-phosphoethanolamine), DOPG (1,2-dioleoyl-sn-glycero-3-phospho-(1'-rac-glycerol)). In some embodiments, the non-cationic lipid is DEPE or DOPE.

In the various aspects of the invention, the PEG-modified lipids comprise a poly(ethylene) glycol chain of up to 5 kDa in length covalently attached to a lipid with alkyl chain(s) of $C_6$-$C_{20}$ length. In some embodiments, the PEG-modified lipid is 1,2-dimyristoyl-rac-glycero-3-methoxypolyethylene glycol-2000 (DMG-PEG2K).

In the various aspects of the invention, the mRNA may comprise one or more modified nucleotides. Alternatively, the mRNA is unmodified.

In this application, the use of "or" means "and/or" unless stated otherwise. As used in this disclosure, the term "comprise" and variations of the term, such as "comprising" and "comprises," are not intended to exclude other additives, components, integers or steps. As used in this application, the terms "about" and "approximately" are used as equivalents. Both terms are meant to cover any normal fluctuations appreciated by one of ordinary skill in the relevant art.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF THE DRAWINGS

The drawings are for illustration purposes only and not for limitation.

FIG. 2A is a schematic of a lipid nanoparticle mRNA encapsulation process that involves mixing a suspension of preformed empty lipid nanoparticles, with batches of a solution of mRNA that are added sequentially. In the exemplary process illustrated in FIG. 2A, four batches of mRNA are added. Each addition results in an intermediate mixture with a different molar ratio of cationic lipid to mRNA ("N/P"), starting with a ratio of 16 (cationic lipid) to 1 (mRNA), that decreases to 4 (cationic lipid) to 1 (mRNA) in the final formulation. This stepwise decrease in the N/P ratio is illustrated in FIG. 2B. This type of process is referred to herein as "Step Down Remix" process. FIG. 2C shows a corresponding process in which a suspension of preformed empty lipid nanoparticles is added in batches to an mRNA solution, starting with an equimolar ratio of cationic lipid to mRNA. In the exemplary process illustrated in FIG. 2C, four batches of preformed empty lipid nanoparticles are added until a ratio of 4 (cationic lipid) to 1 (mRNA) is reached. This stepwise increase in the N/P ratio is illustrated in FIG. 2D. This type of process is referred to herein as "Step Up Remix" process.

FIG. 3A and FIG. 3B show variations of these processes, in which batches of either preformed lipid nanoparticles or mRNA are added at three different occasions, followed each time by a period of mixing. The final mixing period is extended relative to the other mixing period. FIG. 3C and FIG. 3D show other variations of the Step Down and Step Up Remix processes, in which either preformed lipid nanoparticles or mRNA is added continuously over a period of time such that the molar ratio of cationic lipid to mRNA ("N/P" ratio) either decreases or increases during that period until a desired N/P ratio is reached. FIG. 3E and FIG. 3F show further variations that combine Step Down and Step Up Remix processes. These variant processes alternate between the addition of preformed lipid nanoparticles and mRNA, or vice versa, leading both to stepped increases and decreases of the N/P ratio before the desired final N/P ratio is reached.

FIG. 7A is a schematic illustration of the study protocol. The hOTC mRNA was encapsulated in a 4-component lipid nanoparticle (cDD-TE-4-E12, DEPE, cholesterol, and DMG-PEG2K) using the exemplary Step Down Remix Process shown in FIG. 2A. The mRNA-loaded lipid nanoparticles were administered to $OTC^{spf/ash}$ mice at the indicated doses. Saline-treated wild-type and $OTC^{spf/ash}$ mice served as controls. 24 hours post dose the animals were challenged with $NH_4Cl$, and plasma $NH_3$ levels were measured 40 minutes post challenge. Liver homogenates were analyzed by ELISA to determine hOTC protein expression levels. FIG. 7B shows that the amount of hOTC relative to total protein (shown in ng/mg) increased in a dose-dependent manner. FIG. 7C shows that plasma $NH_3$ levels decreased in a dose-dependent manner.

FIG. 8A is a schematic illustration of the study protocol. The hOTC mRNA was encapsulated in a 4-component lipid nanoparticle (cDD-TE-4-E12, DEPE, cholesterol, and DMG-PEG2K) using the exemplary Step Down Remix process shown in FIG. 2A. The mRNA-loaded lipid nanoparticles were administered to $OTC^{spf/ash}$ mice at a dose of 0.3 mg/kg. Saline-treated wild-type and $OTC^{spf/ash}$ mice served as controls. 1, 2 and 3 weeks post dose the animals were challenged with $NH_4Cl$, and plasma $NH_3$ levels were measured 40 minutes post challenge. FIG. 8B shows that amounts of OTC protein from the administered hOTC mRNA were adequate to reduce plasma $NH_3$ levels to levels close to or undistinguishable from saline-treated wildtype mice for at least 15 days post administration.

FIG. 10A shows the amount of human erythropoietin (hEPO) protein expressed in serum after 6 and 24 hours following a single bolus injection of mRNA-loaded lipid nanoparticles at a 1.0 mg/kg dose. Saline-treated mice served as a control. The hEPO expression level in mice treated with ML2-based lipid nanoparticles prepared with the conventional "Remix" process ("ML2 Remix") served as a benchmark. All three tested "Re-Blend" formulations showed a boost in hEPO expression at the 6 hour time point. FIG. 10B shows that tolerability of the "Re-Blend" formulations was comparable to the "Remix" formulation benchmark. Tolerability was assessed on the basis of ALT and AST expression levels in the liver of the test animals. An increase in ALT and AST expression levels is indicative of liver toxicity. The dashed line shows the average expression levels of hEPO, ALT and AST, respectively, of mice treated with the "ML2 Remix" benchmark formulation.

DEFINITIONS

Figure 1B:
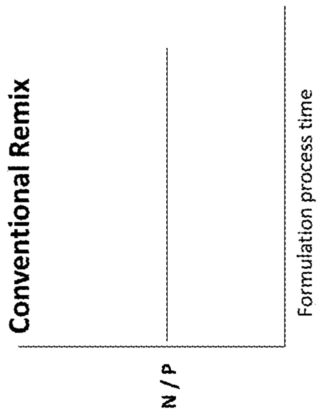
FIGS. 1A-1C show a schematic of a lipid nanoparticle mRNA encapsulation process that involves mixing a suspension of preformed empty lipid nanoparticles, with a solution of mRNA dissolved in an aqueous buffer (see FIG. 1A). This process is referred to herein as the conventional "Remix" process, or "Process B". The molar ratio of cationic lipid to mRNA (also colloquially referred to as "N/P" ratio) remains constant during the mixing process, as illustrated in FIG. 1B. The suspension comprising the preformed empty lipid nanoparticles is at 65° C., while the mRNA solution is at ambient temperature, as shown in FIG. 1C; the two liquids are mixed using a pump system and the combined mixture is heated to 65° C. to remove the temperature difference as indicated by the ΔT.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Amino acid: As used herein, the term "amino acid," in its broadest sense, refers to any compound and/or substance that can be incorporated into a polypeptide chain. In some embodiments, an amino acid has the general structure $H_2N—C(H)(R)—COOH$. In some embodiments, an amino acid is a naturally occurring amino acid. In some embodiments, an amino acid is a synthetic amino acid; in some embodiments, an amino acid is a d-amino acid; in some embodiments, an amino acid is an 1-amino acid. "Standard amino acid" refers to any of the twenty standard 1-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or more posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the term "biologically active" refers to a characteristic of any agent that has activity in a biological system, and particularly in an organism. For instance, an agent that, when administered to an organism, has a biological effect on that organism, is considered to be biologically active.

Delivery: As used herein, the term "delivery" encompasses both local and systemic delivery. For example, delivery of mRNA encompasses situations in which an mRNA is delivered to a target tissue and the encoded protein or peptide is expressed and retained within the target tissue (also referred to as "local distribution" or "local delivery"), and situations in which an mRNA is delivered to a target tissue and the encoded protein or peptide is expressed and secreted into a patient's circulation system (e.g., serum) and systematically distributed and taken up by other tissues (also referred to as "systemic distribution" or "systemic delivery").

Efficacy: As used herein, the term "efficacy," or its grammatical equivalents, refers to an improvement of a biologically relevant endpoint, as related to delivery of mRNA that encodes a relevant protein or peptide. In some embodiments, the biological endpoint is protecting against an ammonium chloride challenge at certain timepoints after administration.

Encapsulation: As used herein, the term "encapsulation," or its grammatical equivalents, refers to the process of confining a nucleic acid molecule (such as an individual mRNA molecule) within a nanoparticle.

Expression: As used herein, "expression" of a mRNA refers to translation of an mRNA into a peptide (e.g., an antigen), polypeptide, or protein (e.g., an enzyme) and also can include, as indicated by context, the post-translational modification of the peptide, polypeptide or fully assembled protein (e.g., enzyme). In this application, the terms "expression" and "production," and their grammatical equivalents, are used interchangeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control sample or subject (or multiple control samples or subjects) in the absence of the treatment described herein. A "control sample" is a sample subjected to the same conditions as a test sample, except for the test article. A "control subject" is a subject afflicted with the same form of disease as the subject being treated, who is about the same age as the subject being treated.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Lipid nanoparticle (LNP): as used herein, LNPs for use with the invention comprise three or four lipid components selected from: a cationic lipid, a non-cationic lipid (e.g., DOPE or DEPE), a cholesterol-based lipid (e.g., cholesterol) and a PEG-modified lipid (e.g., DMG-PEG2K). In some embodiments, an LNP comprises no more than three distinct lipid components. In some embodiments, one distinct lipid component is a sterol-based cationic lipid. An exemplary LNP comprises three lipid components: a sterol-based cationic lipid, a non-cationic lipid (e.g., DOPE or DEPE) and a PEG-modified lipid (e.g., DMG-PEG2K).

messenger RNA (mRNA): As used herein, the term "messenger RNA (mRNA)" refers to a polynucleotide that encodes at least one peptide, polypeptide or protein. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

Multimeric coding nucleic acid (MCNA): mRNA as defined above may include MCNA. MCNA compounds may for example comprise two or more encoding polynucleotides linked via their 3' ends such that the MCNA compound comprises two or more 5' ends. Various MCNA structures and methods of making the same are described in published U.S. Application No. US 2017/0314041, which is incorporated herein by reference in its entirety.

N/P Ratio: As used herein, the term "N/P ratio" refers to a molar ratio of cationic lipids in a lipid nanoparticle relative to mRNA encapsulated within that lipid nanoparticle. As such, N/P ratio is typically calculated as the ratio of moles of cationic lipids in a lipid nanoparticle relative to moles of mRNA encapsulated within that lipid nanoparticle. For example, a 4-fold molar excess of cationic lipid per mol mRNA is referred to as an "N/P ratio" of 4. Various aspects of the invention involve increasing ("stepping up", "Step Up") or decreasing ("stepping down", "Step Down") the N/P ratio during the encapsulation process until a desired ratio is achieved.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery. In some embodiments, the nucleotides T and U are used interchangeably in sequence descriptions.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In specific embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, sulfonate and aryl sulfonate. Further pharmaceutically acceptable salts include salts formed from the quarternization of an amine using an appropriate electrophile, e.g., an alkyl halide, to form a quarternized alkylated amino salt.

Potency: As used herein, the term "potency," or grammatical equivalents, refers to expression of protein(s) or peptide(s) that the mRNA encodes and/or the resulting biological effect.

Processor: As used herein, the term "processor" includes microprocessor, microelectronics which are configured to process data and/or control components of the apparatuses described herein, a virtual processor, and/or an integrated circuit.

Protein: As used herein, the term "protein" includes peptides (such as dipeptides), proteins, polypeptides, and/or assemblies of multiple peptides, polypeptides or proteins. In some embodiments, the term "protein" may exclude peptides. Proteins associated with the invention may be proteins of biological and/or therapeutic relevance.

Systemic distribution or delivery: As used herein, the terms "systemic distribution," "systemic delivery," or grammatical equivalents, refer to a delivery or distribution mechanism or approach that affects the entire body or an entire organism. Typically, systemic distribution or delivery is accomplished via the body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display a disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Yield: As used herein, the term "yield" refers to the percentage of mRNA recovered after encapsulation as compared to the total mRNA as starting material. In some embodiments, the term "recovery" is used interchangeably with the term "yield".

DETAILED DESCRIPTION

The present invention provides an improved process for lipid nanoparticle (LNP) formulation and mRNA encapsulation. In some embodiments, the present invention provides a process of encapsulating messenger RNA (mRNA) in lipid nanoparticles comprising the steps of forming lipids into preformed lipid nanoparticles (i.e., formed in the absence of mRNA) and then combining the preformed lipid nanoparticles with mRNA. In some embodiments, the novel formulation process results in an mRNA formulation with higher potency (peptide, polypeptide or protein expression) and higher efficacy (improvement of a biologically relevant endpoint) both in vitro and in vivo with potentially better tolerability as compared to the same mRNA formulation prepared without the step of preforming the lipid nanoparticles (e.g., combining the lipids directly with the mRNA). The higher potency and/or efficacy of such a formulation can provide for lower and/or less frequent dosing of the drug product. In some embodiments, the invention features an improved lipid formulation comprising a cationic lipid, a helper lipid and a PEG or PEG-modified lipid.

In some embodiments, the resultant encapsulation efficiencies for the present lipid nanoparticle formulation and preparation method are at least 80%, e.g., at least 90%. For the delivery of nucleic acids, achieving encapsulation is typically considered critical to attain protection of the drug substance and reduce loss of activity in vivo. Higher encapsulation efficiencies are typically correlated with the delivery of larger amounts of the encapsulated nucleic acid (e.g., mRNA) to target cells.

Various aspects of the invention are described in detail in the following sections. The use of sections is not meant to limit the invention. Each section can apply to any aspect of the invention.

Messenger RNA (mRNA)

The present invention may be used to encapsulate any mRNA. mRNA is typically thought of as the type of RNA that carries information from DNA to the ribosome. Typically, in eukaryotic organisms, mRNA processing comprises the addition of a "cap" on the 5' end, and a "tail" on the 3' end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The additional of a tail is typically a polyadenylation event whereby a polyadenylyl moiety is added to the 3' end of the mRNA molecule. The presence of this "tail" serves to protect the mRNA from exonuclease degradation. Messenger RNA is translated by the ribosomes into a series of amino acids that make up a protein.

mRNA Synthesis and Properties mRNAs may be synthesized according to any of a variety of known methods. Various methods are described in published U.S. Application No. US 2018/0258423, and can be used to practice the present invention, all of which are incorporated herein by reference. For example, mRNAs for use with the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application. In some embodiments, mRNA may be further purified for use with the present invention. In some embodiments, in vitro synthesized mRNA may be purified before formulation and encapsulation to remove undesirable impurities including various enzymes and other reagents used during mRNA synthesis.

Various methods may be used to purify mRNA for use with the present invention. For example, purification of mRNA can be performed using centrifugation, filtration and/or chromatographic methods. In some embodiments, the synthesized mRNA is purified by ethanol precipitation or filtration or chromatography, or gel purification or any other suitable means. In some embodiments, the mRNA is purified by HPLC. In some embodiments, the mRNA is extracted in a standard phenol: chloroform: isoamyl alcohol solution, well known to one of skill in the art.

In particular embodiments, the mRNA is purified using Tangential Flow Filtration (TFF). Suitable purification methods include those described in published U.S. Application No. US 2016/0040154, published U.S. Application No. US 2015/0376220, published U.S. Application No. US 2018/0251755, published U.S. Application No. US 2018/0251754, U.S. Provisional Application No. 62/757,612 filed on Nov. 8, 2018, and U.S. Provisional Application No. 62/891,781 filed on Aug. 26, 2019, all of which are incorporated by reference herein and may be used to practice the present invention.

In some embodiments, the mRNA is purified before capping and tailing. In some embodiments, the mRNA is purified after capping and tailing. In some embodiments, the mRNA is purified both before and after capping and tailing. In some embodiments, the mRNA is purified either before or after or both before and after capping and tailing, by centrifugation. In some embodiments, the mRNA is purified either before or after or both before and after capping and tailing, by filtration. In some embodiments, the mRNA is purified either before or after or both before and after capping and tailing, by TFF. In some embodiments, the mRNA is purified either before or after or both before and after capping and tailing by chromatography.

The present invention may be used to formulate and encapsulate mRNAs of a variety of lengths. In some embodiments, the present invention may be used to formulate and encapsulate in vitro synthesized mRNA of or greater than about 0.5 kb, 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, 20 kb, 30 kb, 40 kb, or 50 kb in length. In some embodiments, the present invention may be used to formulate and encapsulate in vitro synthesized mRNA ranging from about 1-20 kb, about 1-15 kb, about 1-10 kb, about 5-20 kb, about 5-15 kb, about 5-12 kb, about 5-10 kb, about 8-20 kb, about 8-15 kb, or about 8-50 kb in length.

mRNA Modification

The present invention may be used to formulate and encapsulate mRNA that is unmodified or mRNA containing one or more modifications that typically enhance stability. In some embodiments, modifications are selected from modified nucleotides, modified sugar phosphate backbones, and 5' and/or 3' untranslated region.

In some embodiments, an mRNA comprises or consists of naturally-occurring nucleosides (or unmodified nucleosides; i.e., adenosine, guanosine, cytidine, and uridine). In some embodiments, modifications of mRNA may include modifications of the nucleotides of the RNA (e.g. adenosine analog, guanosine analog, cytidine analog, uridine analog). In some embodiments, an mRNA comprises both unmodified and modified nucleosides. A modified mRNA according to the invention can include, for example, backbone modifications, sugar modifications or base modifications. In some embodiments, the one or more modified nucleosides is a nucleoside analog. In some embodiments, the one or more modified nucleosides comprises at least one modification selected from a modified sugar, and a modified nucleobase. In some embodiments, the mRNA comprises one or more modified internucleoside linkages. In some embodiments, the one or more modified nucleosides comprises a modified nucleobase, for example a chemically modified base, a biologically modified base (e.g., a methylated base), or an intercalated base.

In some embodiments, mRNAs may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine, pseudouridine (e.g., N-1-methyl-pseudouridine), 2-thiouridine, 2-thiocytidine, 5-methylcytidine, inosine, isocytosine, pseudoisocytosine, 5-bromouracil, 5-propynyluracil, 6-aminopurine, 2-aminopurine, diaminopurine and 2-chloro-6-aminopurine cytosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

In some embodiments, the mRNA may be RNA wherein 25% of U residues are 2-thio-uridine and 25% of C residues are 5-methylcytidine. Teachings for the use of such modified RNA are disclosed in US Patent Publication US 2012/0195936 and international publication WO 2011/012316, both of which are hereby incorporated by reference in their entirety. In some embodiments, the presence of one or more nucleoside analogs may render an mRNA more stable and/or less immunogenic than a control mRNA with the same sequence but containing only naturally-occurring nucleosides. See, e.g., U.S. Pat. No. 8,278,036 or WO 2011/012316 for a discussion of 5-methyl-cytidine, pseudouridine, and 2-thio-uridine and their incorporation into mRNA.

In some embodiments, the mRNA comprises one or more modified internucleoside linkages. For example, one or more of the modified nucleotides used to produce the mRNA of the invention may comprise a modified phosphate group. Therefore, in the mRNA, one or more phosphodiester linkages is substituted with another anionic, cationic or neutral group. For example, in some embodiments the one or more modified nucleotides comprises a modified phosphate group selected from methylphosphonates, methylphosphoramidates, phosphoramidates, phosphorothioates (e.g., cytidine 5'-O-(1-thiophosphate)), boranophosphates, and positively charged guanidinium groups. In some embodiments the one or more modified internucleoside linkages is a phosphorothioate linkage. In some embodiments the one or more modified internucleoside linkages is a 5'-N-phosphoramidite linkage.

In some embodiments, the one or more modified nucleosides comprises a modified sugar. In some embodiments the one or more modified nucleosides comprises a modification to the furanose ring. In some embodiments the one or more modified nucleosides comprises a modified sugar selected from 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate). In some embodiments the one or more modified nucleosides comprises a modified sugar selected from a 2'-O-alkyl modification or a locked nucleic acid (LNA). In some embodiments, where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In some embodiments the one or more modified nucleosides comprises a modified sugar selected from 2'-fluororibose, ribose, 2'-deoxyribose, arabinose, and hexose.

In some embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

In some embodiments, the RNAs may be complexed or hybridized with additional polynucleotides and/or peptide polynucleotides (PNA).

Typically, mRNA synthesis includes the addition of a "cap" on the 5' end, and a "tail" on the 3' end. The presence of the cap is important in providing resistance to nucleases found in most eukaryotic cells. The presence of a "tail" serves to protect the mRNA from exonuclease degradation. As described herein, the addition of the 5' cap and/or the 3' tail facilitates the detection of abortive transcripts generated during in vitro synthesis because without capping and/or tailing, the size of those prematurely aborted mRNA transcripts can be too small to be detected. Thus, in some embodiments, the 5' cap and/or the 3' tail are added to the synthesized mRNA before the mRNA is tested for purity (e.g., the level of abortive transcripts present in the mRNA). In some embodiments, the 5' cap and/or the 3' tail are added to the synthesized mRNA before the mRNA is purified as described herein. In other embodiments, the 5' cap and/or the 3' tail are added to the synthesized mRNA after the mRNA is purified as described herein.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. 2'-O-methylation may also occur at the first base and/or second base following the 7-methyl guanosine triphosphate residues. Examples of cap structures include, but are not limited to, m7GpppNp-RNA, m7GpppNmp-RNA, m7GpppNmpNmp-RNA (where m indicates 2'-Omethyl residues), m7G(5')ppp (5'(A,G(5')ppp(5')A and G(5')ppp(5') G. Additional cap structures are described in published U.S. Application No. US 2016/0032356 and published U.S. Application No. US 2018/0125989, which are incorporated herein by reference.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer. Typically, a tail structure includes a poly(A) and/or poly(C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly A or poly C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes or is a combination of poly (A) and poly (C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

While mRNA provided from in vitro transcription reactions may be desirable in some embodiments, other sources of mRNA are contemplated as within the scope of the invention including mRNA produced from bacteria, fungi, plants, and/or animals.

mRNA-Encoded Proteins

In some embodiments, a suitable mRNA sequence is an mRNA sequence encoding a peptide, polypeptide or protein. In some embodiments, a suitable mRNA sequence is codon optimized for efficient expression in human cells. Codon optimization typically includes modifying a naturally-occurring or wild-type nucleic acid sequence encoding a peptide, polypeptide or protein to achieve the highest possible G/C content, to adjust codon usage to avoid rare or rate-limiting codons, to remove destabilizing nucleic acid sequences or motifs and/or to eliminate pause sites or terminator sequences without altering the amino acid sequence of the mRNA encoded peptide, polypeptide or protein. In some embodiments, a suitable mRNA sequence is naturally-occurring or a wild-type sequence. In some embodiments, a suitable mRNA sequence encodes a protein, polypeptide, or peptide that contains one or more mutations in amino acid sequence.

The present invention may be used to formulate and encapsulate mRNAs encoding a variety of proteins. Non-limiting examples of mRNAs suitable for the present invention include mRNAs encoding spinal motor neuron 1 (SMN), alpha-galactosidase (GLA), argininosuccinate synthetase (ASS1), ornithine transcarbamylase (OTC), Factor IX (FIX), phenylalanine hydroxylase (PAH), erythropoietin (EPO), and cystic fibrosis transmembrane conductance receptor (CFTR). Exemplary mRNA sequences as disclosed herein are listed below:

Codon-Optimized Human OTC Coding Sequence (SEQ ID NO: 1)

```
AUGCUGUUCAACCUUCGGAUCUUGCUGAACAACGCUGCGUUCCGGAAUGG
UCACAACUUCAUGGUCCGGAACUUCAGAUGCGGCCAGCCGCUCCAGAACA
AGGUGCAGCUCAAGGGGAGGGACCUCCUCACCCUGAAAAACUUCACCGGA
GAAGAGAUCAAGUACAUGCUGUGGCUGUCAGCCGACCUCAAAUUCCGGAU
CAAGCAGAAGGGCGAAUACCUUCCUUUGCUGCAGGGAAAGUCCCUGGGGA
UGAUCUUCGAGAAGCGCAGCACUCGCACUAGACUGUCAACUGAAACCGGC
UUCGCGCUGCUGGGAGGACACCCCUGCUUCCUGACCACCCAAGAUAUCCA
UCUGGGUGUGAACGAAUCCCUCACCGACACAGCGCGGGUGCUGUCGUCCA
UGGCAGACGCGGUCCUCGCCCGCGUGUACAAGCAGUCUGAUCUGGACACU
CUGGCCAAGGAAGCCUCCAUUCCUAUCAUUAAUGGAUUGUCCGACCUCUA
CCAUCCCAUCCAGAUUCUGGCCGAUUAUCUGACUCUGCAAGAACAUUACA
GCUCCCUGAAGGGGCUUACCCUUUCGUGGAUCGGCGACGGCAACAACAUU
CUGCACAGCAUUAUGAUGAGCGCUGCCAAGUUUGGAAUGCACCUCCAAGC
AGCGACCCCGAAGGGAUACGAGCCAGACGCCUCCGUGACGAAGCUGGCUG
AGCAGUACGCCAAGGAGAACGGCACUAAGCUGCUGCUCACCAACGACCCU
CUCGAAGCCGCCCACGGUGGCAACGUGCUGAUCACCGAUACCUGGAUCUC
CAUGGGACAGGAGGAGGAAAAGAAGAAGCGCCUGCAAGCAUUUCAGGGGU
ACCAGGUGACUAUGAAAACCGCCAAGGUCGCCGCCUCGGACUGGACCUUC
UUGCACUGUCUGCCCAGAAAGCCCGAAGAGGUGGACGACGAGGUGUUCUA
CAGCCCGCGGUCGCUGGUCUUUCCGGAGGCCGAAAACAGGAAGUGGACUA
UCAUGGCCGUGAUGGUGUCCCUGCUGACCGAUUACUCCCCGCAGCUGCAG
AAACCAAAGUUCUGA
```

Codon-Optimized Human ASS1 Coding Sequence (SEQ ID NO: 2)

```
AUGAGCAGCAAGGGCAGCGUGGUGCUGGCCUACAGCGGCGGCCUGGACAC
CAGCUGCAUCCUGGUGUGGCUGAAGGAGCAGGGCUACGACGUGAUCGCCU
ACCUGGCCAACAUCGGCCAGAAGGAGGACUUCGAGGAGGCCCGCAAGAAG
GCCCUGAAGCUGGGCGCCAAGAAGGUGUUCAUCGAGGACGUGAGCCGCGA
GUUCGUGGAGGAGUUCAUCUGGCCCGCCAUCCAGAGCAGCGCCCUGUACG
AGGACCGCUACCUGCUGGGCACCAGCCUGGCCCGCCCCUGCAUCGCCCGC
AAGCAGGUGGAGAUCGCCCAGCGCGAGGGCGCCAAGUACGUGAGCCACGG
CGCCACCGGCAAGGGCAACGACCAGGUGCGCUUCGAGCUGAGCUGCUACA
GCCUGGCCCCCCAGAUCAAGGUGAUCGCCCCCUGGCGCAUGCCCGAGUUC
UACAACCGCUUCAAGGGCCGCAACGACCUGAUGGAGUACGCCAAGCAGCA
CGGCAUCCCCAUCCCCGUGACCCCCAAGAACCCCUGGAGCAUGGACGAGA
ACCUGAUGCACAUCAGCUACGAGGCCGGCAUCCUGGAGAACCCCAAGAAC
CAGGCCCCCCCCGGCCUGUACACCAAGACCCAGGACCCCGCCAAGGCCCC
CAACACCCCCGACAUCCUGGAGAUCGAGUUCAAGAAGGGCGUGCCCGUGA
AGGUGACCAACGUGAAGGACGGCACCACCCACCAGACCAGCCUGGAGCUG
```

-continued

UUCAUGUACCUGAACGAGGUGGCCGGCAAGCACGGCGUGGGCCGCAUCGA

CAUCGUGGAGAACCGCUUCAUCGGCAUGAAGAGCCGCGGCAUCUACGAGA

CCCCCGCCGGCACCAUCCUGUACCACGCCCACCUGGACAUCGAGGCCUUC

ACCAUGGACCGCGAGGUGCGCAAGAUCAAGCAGGGCCUGGGCCUGAAGUU

CGCCGAGCUGGUGUACACCGGCUUCUGGCACAGCCCCGAGUGCGAGUUCG

UGCGCCACUGCAUCGCCAAGAGCCAGGAGCGCGUGGAGGGCAAGGUGCAG

GUGAGCGUGCUGAAGGGCCAGGUGUACAUCCUGGGCCGCGAGAGCCCCCU

GAGCCUGUACAACGAGGAGCUGGUGAGCAUGAACGUGCAGGGCGACUACG

AGCCCACCGACGCCACCGGCUUCAUCAACAUCAACAGCCUGCGCCUGAAG

GAGUACCACCGCCUGCAGAGCAAGGUGACCGCCAAGUGA

Codon-Optimized Human CFTR Coding Sequence (SEQ ID NO: 3)

AUGCAACGCUCUCCUCUUGAAAAGGCCUCGGUGGUGUCCAAGCUCUUCUU

CUCGUGGACUAGACCCAUCCUGAGAAAGGGGUACAGACAGCGCUUGGAGC

UGUCCGAUAUCUAUCAAAUCCCUUCCGUGGACUCCGCGGACAACCUGUCC

GAGAAGCUCGAGAGAGAAUGGGACAGAGAACUCGCCUCAAAGAAGAACCC

GAAGCUGAUUAAUGCGCUUAGGCGGUGCUUUUUCUGGCGGUUCAUGUUCU

ACGGCAUCUUCCUCUACCUGGGAGAGGUCACCAAGGCCGUGCAGCCCCUG

UUGCUGGGACGGAUUAUUGCCUCCUACGACCCCGACAACAAGGAAGAAAG

AAGCAUCGCUAUCUACUUGGGCAUCGGUCUGUGCCUGCUUUUCAUCGUCC

GGACCCUCUUGUUGCAUCCUGCUAUUUUCGGCCUGCAUCACAUUGGCAUG

CAGAUGAGAAUUGCCAUGUUUUCCCUGAUCUACAAGAAAACUCUGAAGCU

CUCGAGCCGCGUGCUUGACAAGAUUUCCAUCGGCCAGCUCGUGUCCCUGC

UCUCCAACAAUCUGAACAAGUUCGACGAGGGCCUCGCCCUGGCCCACUUC

GUGUGGAUCGCCCCUCUGCAAGUGGCGCUUCUGAUGGGCCUGAUCUGGGA

GCUGCUGCAAGCCUCGGCAUUCUGUGGGCUUGGAUUCCUGAUCGUGCUGG

CACUGUUCCAGGCCGGACUGGGGCGGAUGAUGAUGAAGUACAGGGACCAG

AGAGCCGGAAAGAUUUCCGAACGGCUGGUGAUCACUUCGGAAAUGAUCGA

AAACAUCCAGUCAGUGAAGGCCUACUGCUGGGAAGAGGCCAUGGAAAAGA

UGAUUGAAAACCUCCGGCAAACCGAGCUGAAGCUGACCCGCAAGGCCGCU

UACGUGCGCUAUUUCAACUCGUCCGCUUUCUUCUUCUCCGGGUUCUUCGU

GGUGUUUCUCUCCGUGCUCCCCUACGCCCUGAUUAAGGGAAUCAUCCUCA

GGAAGAUCUUCACCACCAUUUCCUUCUGUAUCGUGCUCCGCAUGGCCGUG

ACCCGGCAGUUCCCAUGGGCCGUGCAGACUUGGUACGACUCCCUGGGAGC

CAUUAACAAGAUCCAGGACUUCCUUCAAAAGCAGGAGUACAAGACCCUCG

AGUACAACCUGACUACUACCGAGGUCGUGAUGGAAAACGUCACCGCCUUU

UGGGAGGAGGGAUUUGGCGAACUGUUCGAGAAGGCCAAGCAGAACAACAA

CAACCGCAAGACCUCGAACGGUGACGACUCCCUCUUCUUUUCAAACUUCA

GCCUGCUCGGGACGCCCGUGCUGAAGGACAUUAACUUCAAGAUCGAAAGA

GGACAGCUCCUGGCGGUGGCCGGAUCGACCGGAGCCGGAAAGACUUCCCU

-continued

GCUGAUGGUGAUCAUGGGAGAGCUUGAACCUAGCGAGGGAAAGAUCAAGC

ACUCCGGCCGCAUCAGCUUCUGUAGCCAGUUUUCCUGGAUCAUGCCCGGA

ACCAUUAAGGAAAACAUCAUCUUCGGCGUGUCCUACGAUGAAUACCGCUA

CCGGUCCGUGAUCAAAGCCUGCCAGCUGGAAGAGGAUAUUUCAAAGUUCG

CGGAGAAAGAUAACAUCGUGCUGGGCGAAGGGGGUAUUACCUUGUCGGGG

GGCCAGCGGGCUAGAAUCUCGCUGGCCAGAGCCGUGUAUAAGGACGCCGA

CCUGUAUCUCCUGGACUCCCCCUUCGGAUACCUGGACGUCCUGACCGAAA

AGGAGAUCUUCGAAUCGUGCGUGUGCAAGCUGAUGGCUAACAAGACUCGC

AUCCUCGUGACCUCCAAAAUGGAGCACCUGAAGAAGGCAGACAAGAUUCU

GAUUCUGCAUGAGGGGUCCUCCUACUUUUACGGCACCUUCUCGGAGUUGC

AGAACUUGCAGCCCGACUUCUCAUCGAAGCUGAUGGGUUGCGACAGCUUC

GACCAGUUCUCCGCCGAAAGAAGGAACUCGAUCCUGACGGAAACCUUGCA

CCGCUUCUCUUUGGAAGGCGACGCCCCUGUGUCAUGGACCGAGACUAAGA

AGCAGAGCUUCAAGCAGACCGGGGAAUUCGGCGAAAAGAGGAAGAACAGC

AUCUUGAACCCCAUUAACUCCAUCCGCAAGUUCUCAAUCGUGCAAAAGAC

GCCACUGCAGAUGAACGGCAUUGAGGAGGACUCCGACGAACCCCUUGAGA

GGCGCCUGUCCCUGGUGCCGGACAGCGAGCAGGGAGAAGCCAUCCUGCCU

CGGAUUUCCGUGAUCUCCACUGGUCCGACGCUCCAAGCCCGGCGGCGGCA

GUCCGUGCUGAACCUGAUGACCCACAGCGUGAACCAGGGCCAAAACAUUC

ACCGCAAGACUACCGCAUCCACCCGGAAAGUGUCCCUGGCACCUCAAGCG

AAUCUUACCGAGCUCGACAUCUACUCCCGGAGACUGUCGCAGGAAACCGG

GCUCGAAAUUUCCGAAGAAAUCAACGAGGAGGAUCUGAAAGAGUGCUUCU

UCGACGAUAUGGAGUCGAUACCCGCCGUGACGACUUGGAACACUUAUCUG

CGGUACAUCACUGUGCACAAGUCAUUGAUCUUCGUGCUGAUUUGGUGCCU

GGUGAUUUUCCUGGCCGAGGUCGCGGCCUCACUGGUGGUGCUCUGGCUGU

UGGGAAACACGCCUCUGCAAGACAAGGGAAACUCCACGCACUCGAGAAAC

AACAGCUAUGCCGUGAUUAUCACUUCCACCUCCUCUUAUUACGUGUUCUA

CAUCUACGUCGGAGUGGCGGAUACCCUGCUCGCGAUGGGUUUCUUCAGAG

GACUGCCGCUGGUCCACACCUUGAUCACCGUCAGCAAGAUUCUUCACCAC

AAGAUGUUGCAUAGCGUGCUGCAGGCCCCCAUGUCCACCCUCAACACUCU

GAAGGCCGGAGGCAUUCUGAACAGAUUCUCCAAGGACAUCGCUAUCCUGG

ACGAUCUCCUGCCGCUUACCAUCUUUGACUUCAUCCAGCUGCUGCUGAUC

GUGAUUGGAGCAAUCGCAGUGGUGGCGGUGCUGCAGCCUUACAUUUUCGU

GGCCACUGUGCCGGUCAUUGUGGCGUUCAUCAUGCUGCGGGCCUACUUCC

UCCAAACCAGCCAGCAGCUGAAGCAACUGGAAUCCGAGGGACGAUCCCCC

AUCUUCACUCACCUUGUGACGUCGUUGAAGGGACUGUGGACCCUCCGGGC

UUUCGGACGGCAGCCCUACUUCGAAACCCUCUUCCACAAGGCCCUGAACC

UCCACACCGCCAAUUGGUUCCUGUACCUGUCCACCCUGCGGUGGUUCCAG

AUGCGCAUCGAGAUGAUUUUCGUCAUCUUCUUCAUCGCGGUCACAUUCAU

CAGCAUCCUGACUACCGGAGAGGGAGAGGGACGGGUCGGAAUAAUCCUGA

-continued

CCCUCGCCAUGAACAUUAUGAGCACCCUGCAGUGGGCAGUGAACAGCUCG

AUCGACGUGGACAGCCUGAUGCGAAGCGUCAGCCGCGUGUUCAAGUUCAU

CGACAUGCCUACUGAGGGAAAACCCACUAAGUCCACUAAGCCCUACAAAA

AUGGCCAGCUGAGCAAGGUCAUGAUCAUCGAAAACUCCCACGUGAAGAAG

GACGAUAUUUGGCCCUCCGGAGGUCAAAUGACCGUGAAGGACCUGACCGC

AAAGUACACCGAGGGAGGAAACGCCAUUCUCGAAAACAUCAGCUUCUCCA

UUUCGCCGGGACAGCGGGUCGGCCUUCUCGGGCGGACCGGUUCCGGGAAG

UCAACUCUGCUGUCGGCUUUCCUCCGGCUGCUGAAUACCGAGGGGGAAAU

CCAAAUUGACGGCGUGUCUUGGGAUUCCAUUACUCUGCAGCAGUGGCGGA

AGGCCUUCGGCGUGAUCCCCCAGAAGGUGUUCAUCUUCUCGGGUACCUUC

CGGAAGAACCUGGAUCCUUACGAGCAGUGGAGCGACCAAGAAAUCUGGAA

GGUCGCCGACGAGGUCGGCCUGCGCUCCGUGAUUGAACAAUUUCCUGGAA

AGCUGGACUUCGUGCUCGUCGACGGGGGAUGUGUCCUGUCGCACGGACAU

AAGCAGCUCAUGUGCCUCGCACGGUCCGUGCUCUCCAAGGCCAAGAUUCU

GCUGCUGGACGAACCUUCGGCCCACCUGGAUCCGGUCACCUACCAGAUCA

UCAGGAGGACCCUGAAGCAGGCCUUUGCCGAUUGCACCGUGAUUCUCUGC

GAGCACCGCAUCGAGGCCAUGCUGGAGUGCCAGCAGUUCCUGGUCAUCGA

GGAGAACAAGGUCCGCCAAUACGACUCCAUUCAAAAGCUCCUCAACGAGC

GGUCGCUGUUCAGACAAGCUAUUUCACCGUCCGAUAGAGUGAAGCUCUUC

CCGCAUCGGAACAGCUCAAAGUGCAAAUCGAAGCCGCAGAUCGCAGCCUU

GAAGGAAGAGACUGAGGAAGAGGUGCAGGACACCCGGCUUUAA

Comparison Codon-Optimized Human CFTR mRNA Coding Sequence (SEQ ID NO: 4)

AUGCAGCGGUCCCCGCUCGAAAAGGCCAGUGUCGUGUCCAAACUCUUCUU

CUCAUGGACUCGGCCUAUCCUUAGAAAGGGGUAUCGGCAGAGGCUUGAGU

UGUCUGACAUCUACCAGAUCCCCUCGGUAGAUUCGGCGGAUAACCUCUCG

GAGAAGCUCGAACGGGAAUGGGACCGCGAACUCGCGUCUAAGAAAAACCC

GAAGCUCAUCAACGCACUGAGAAGGUGCUUCUUCUGGCGGUUCAUGUUCU

ACGGUAUCUUCUUGUAUCUCGGGGAGGUCACAAAAGCAGUCCAACCCCUG

UUGUUGGGUCGCAUUAUCGCCUCGUACGACCCCGAUAACAAAGAAGAACG

GAGCAUCGCGAUCUACCUCGGGAUCGGACUGUGUUUGCUUUUCAUCGUCA

GAACACUUUUGUUGCAUCCAGCAAUCUUCGGCCUCCAUCACAUCGGUAUG

CAGAUGCGAAUCGCUAUGUUUAGCUUGAUCUACAAAAAGACACUGAAACU

CUCGUCGCGGGUGUUGGAUAAGAUUUCCAUCGGUCAGUUGGUGUCCCUGC

UUAGUAAUAACCUCAACAAAUUCGAUGAGGGACUGGCGCUGGCACAUUUC

GUGUGGAUUGCCCCGUUGCAAGUCGCCCUUUUGAUGGGCCUUAUUUGGGA

GCUGUUGCAGGCAUCUGCCUUUUGUGGCCUGGGAUUUCUGAUUGUGUUGG

CAUUGUUUCAGGCUGGGCUUGGGCGGAUGAUGAUGAAGUAUCGCGACCAG

AGAGCGGGUAAAAUCUCGGAAAGACUCGUCAUCACUUCGGAAAUGAUCGA

AAACAUCCAGUCGGUCAAAGCCUAUUGCUGGGAAGAAGCUAUGGAGAAGA

UGAUUGAAAACCUCCGCCAAACUGAGCUGAAACUGACCCGCAAGGCGGCG

UAUGUCCGGUAUUUCAAUUCGUCAGCGUUCUUCUUUUCCGGGUUCUUCGU

UGUCUUUCUCUCGGUUUUGCCUUAUGCCUUGAUUAAGGGGAUUAUCCUCC

GCAAGAUUUUCACCACGAUUUCGUUCUGCAUUGUAUUGCGCAUGGCAGUG

ACACGGCAAUUUCCGUGGGCCGUGCAGACAUGGUAUGACUCGCUUGGAGC

GAUCAACAAAAUCCAAGACUUCUUGCAAAAGCAAGAGUACAAGACCCUGG

AGUACAAUCUUACUACUACGGAGGUAGUAAUGGAGAAUGUGACGGCUUUU

UGGGAAGAGGGUUUUGGAGAACUGUUUGAGAAAGCAAAGCAGAAUAACAA

CAACCGCAAGACCUCAAAUGGGGACGAUUCCCUGUUUUUCUCGAACUUCU

CCCUGCUCGGAACACCCGUGUUGAAGGACAUCAAUUUCAAGAUUGAGAGG

GGACAGCUUCUCGCGGUAGCGGGAAGCACUGGUGCGGGAAAAACUAGCCU

CUUGAUGGUGAUUAUGGGGGAGCUUGAGCCCAGCGAGGGGAAGAUUAAAC

ACUCCGGGCGUAUCUCAUUCUGUAGCCAGUUUUCAUGGAUCAUGCCCGGA

ACCAUUAAAGAGAACAUCAUUUUCGGAGUAUCCUAUGAUGAGUACCGAUA

CAGAUCGGUCAUUAAGGCGUGCCAGUUGGAAGAGGACAUUUCUAAGUUCG

CCGAGAAGGAUAACAUCGUCUUGGGAGAAGGGGGUAUUACAUUGUCGGGA

GGGCAGCGAGCGCGGAUCAGCCUCGCGAGAGCGGUAUACAAAGAUGCAGA

UUUGUAUCUGCUUGAUUCACCGUUUGGAUACCUCGACGUAUUGACAGAAA

AAGAAAUCUUCGAGUCGUGCGUGUGUAAACUUAUGGCUAAUAAGACGAGA

AUCCUGGUGACAUCAAAAAUGGAACACCUUAAGAAGGCGGACAAGAUCCU

GAUCCUCCACGAAGGAUCGUCCUACUUUUACGGCACUUUCUCAGAGUUGC

AAAACUUGCAGCCGGACUUCUCAAGCAAACUCAUGGGGUGUGACUCAUUC

GACCAGUUCAGCGCGGAACGGCGGAACUCGAUCUUGACGGAAACGCUGCA

CCGAUUCUCGCUUGAGGGUGAUGCCCCGGUAUCGUGGACCGAGACAAAGA

AGCAGUCGUUUAAGCAGACAGGAGAAUUUGGUGAGAAAAGAAAGAACAGU

AUCUUGAAUCCUAUUAACUCAAUUCGCAAGUUCUCAAUCGUCCAGAAAAC

UCCACUGCAGAUGAAUGGAAUUGAAGAGGAUUCGGACGAACCCCUGGAGC

GCAGGCUUAGCCUCGUGCCGGAUUCAGAGCAAGGGGAGGCCAUUCUUCCC

CGGAUUUCGGUGAUUUCAACCGGACCUACACUUCAGGCGAGGCGAAGGCA

AUCCGUGCUCAACCUCAUGACGCAUUCGGUAAACCAGGGGCAAAACAUUC

ACCGCAAAACGACGGCCUCAACGAGAAAAGUGUCACUUGCACCCCAGGCG

AAUUUGACUGAACUCGACAUCUACAGCCGUAGGCUUUCGCAAGAAACCGG

ACUUGAGAUCAGCGAAGAAAUCAAUGAAGAAGAUUUGAAAGAGUGUUUCU

UUGAUGACAUGGAAUCAAUCCCAGCGGUGACAACGUGGAACACAUACUUG

CGUUACAUCACGGUGCACAAGUCCUUGAUUUUCGUCCUCAUCUGGUGUCU

CGUGAUCUUUCUCGCUGAGGUCGCAGCGUCACUUGUGGUCCUCUGGCUGC

UUGGUAAUACGCCCUUGCAAGACAAAGGCAAUUCUACACACUCAAGAAAC

AAUUCCUAUGCCGUGAUUAUCACUUCUACAAGCUCGUAUUACGUGUUUUA

CAUCUACGUAGGAGUGGCCGACACUCUGCUCGCGAUGGGUUUCUUCCGAG

GACUCCCACUCGUUCACACGCUUAUCACUGUCUCCAAGAUUCUCCACCAU

-continued

AAGAUGCUUCAUAGCGUACUGCAGGCUCCCAUGUCCACCUUGAAUACGCU

CAAGGCGGGAGGUAUUUUGAAUCGCUUCUCAAAAGAUAUUGCAAUUUUGG

AUGACCUUCUGCCCCUGACGAUCUUCGACUUCAUCCAGUUGUUGCUGAUC

GUGAUUGGGGCUAUUGCAGUAGUCGCUGUCCUCCAGCCUUACAUUUUUGU

CGCGACCGUUCCGGUGAUCGUGGCGUUUAUCAUGCUGCGGGCCUAUUUCU

UGCAGACGUCACAGCAGCUUAAGCAACUGGAGUCUGAAGGGAGGUCGCCU

AUCUUUACGCAUCUUGUGACCAGUUUGAAGGGAUUGUGGACGUUGCGCGC

CUUUGGCAGGCAGCCCUACUUUGAAACACUGUUCCACAAAGCGCUGAAUC

UCCAUACGGCAAAUUGGUUUUUGUAUUUGAGUACCCUCCGAUGGUUUCAG

AUGCGCAUUGAGAUGAUUUUUGUGAUCUUCUUUAUCGCGGUGACUUUUAU

CUCCAUCUUGACCACGGGAGAGGGCGAGGGACGGGUCGGUAUUAUCCUGA

CACUCGCCAUGAACAUUAUGAGCACUUUGCAGUGGGCAGUGAACAGCUCG

AUUGAUGUGGAUAGCCUGAUGAGGUCCGUUUCGAGGGUCUUUAAGUUCAU

CGACAUGCCGACGGAGGGAAAGCCCACAAAAAGUACGAAACCCUAUAAGA

AUGGGCAAUUGAGUAAGGUAAUGAUCAUCGAGAACAGUCACGUGAAGAAG

GAUGACAUCUGGCCUAGCGGGGGUCAGAUGACCGUGAAGGACCUGACGGC

AAAAUACACCGAGGGAGGGAACGCAAUCCUUGAAAACAUCUCGUUCAGCA

UUAGCCCCGGUCAGCGUGUGGGGUUGCUCGGGAGGACCGGGUCAGGAAAA

UCGACGUUGCUGUCGGCCUUCUUGAGACUUCUGAAUACAGAGGGUGAGAU

CCAGAUCGACGGCGUUUCGUGGGAUAGCAUCACCUUGCAGCAGUGGCGGA

AAGCGUUUGGAGUAAUCCCCCAAAAGGUCUUUAUCUUUAGCGGAACCUUC

CGAAAGAAUCUCGAUCCUUAUGAACAGUGGUCAGAUCAAGAGAUUUGGAA

AGUCGCGGACGAGGUUGGCCUUCGGAGUGUAAUCGAGCAGUUUCCGGGAA

AACUCGACUUUGUCCUUGUAGAUGGGGGAUGCGUCCUGUCGCAUGGGCAC

AAGCAGCUCAUGUGCCUGGCGCGAUCCGUCCUCUCUAAAGCGAAAAUUCU

UCUCUUGGAUGAACCUUCGGCCCAUCUGGACCCGGUAACGUAUCAGAUCA

UCAGAAGGACACUUAAGCAGGCGUUUGCCGACUGCACGGUGAUUCUCUGU

GAGCAUCGUAUCGAGGCCAUGCUCGAAUGCCAGCAAUUUCUUGUCAUCGA

AGAGAAUAAGGUCCGCCAGUACGACUCCAUCCAGAAGCUGCUUAAUGAGA

GAUCAUUGUUCCGGCAGGCGAUUUCACCAUCCGAUAGGGUGAAACUUUUU

CCACACAGAAAUUCGUCGAAGUGCAAGUCCAAACCGCAGAUCGCGGCCUU

GAAAGAAGAGACUGAAGAAGAAGUUCAAGACACGCGUCUUUAA

Codon-Optimized Human PAH Coding Sequence (SEQ ID NO: 5)

AUGAGCACCGCCGUGCUGGAGAACCCCGGCCUGGGCCGCAAGCUGAGCGA

CUUCGGCCAGGAGACCAGCUACAUCGAGGACAACUGCAACCAGAACGGCG

CCAUCAGCCUGAUCUUCAGCCUGAAGGAGGAGGUGGGCGCCCUGGCCAAG

GUGCUGCGCCUGUUCGAGGAGAACGACGUGAACCUGACCCACAUCGAGAG

CCGCCCCAGCCGCCUGAAGAAGGACGAGUACGAGUUCUUCACCCACCUGG

ACAAGCGCAGCCUGCCCGCCCUGACCAACAUCAUCAAGAUCCUGCGCCAC

-continued

GACAUCGGCGCCACCGUGCACGAGCUGAGCCGCGACAAGAAGAAGGACAC

CGUGCCCUGGUUCCCCCGCACCAUCCAGGAGCUGGACCGCUUCGCCAACC

AGAUCCUGAGCUACGGCGCCGAGCUGGACGCCGACCACCCCGGCUUCAAG

GACCCCGUGUACCGCGCCCGCCGCAAGCAGUUCGCCGACAUCGCCUACAA

CUACCGCCACGGCCAGCCCAUCCCCCGCGUGGAGUACAUGGAGGAGGAGA

AGAAGACCUGGGGCACCGUGUUCAAGACCCUGAAGAGCCUGUACAAGACC

CACGCCUGCUACGAGUACAACCACAUCUUCCCCCUGCUGGAGAAGUACUG

CGGCUUCCACGAGGACAACAUCCCCCAGCUGGAGGACGUGAGCCAGUUCC

UGCAGACCUGCACCGGCUUCCGCCUGCGCCCCGUGGCCGGCCUGCUGAGC

AGCCGCGACUUCCUGGGCGGCCUGGCCUUCCGCGUGUUCCACUGCACCCA

GUACAUCCGCCACGGCAGCAAGCCCAUGUACACCCCCGAGCCCGACAUCU

GCCACGAGCUGCUGGGCCACGUGCCCCUGUUCAGCGACCGCAGCUUCGCC

CAGUUCAGCCAGGAGAUCGGCCUGGCCAGCCUGGGCGCCCCCGACGAGUA

CAUCGAGAAGCUGGCCACCAUCUACUGGUUCACCGUGGAGUUCGGCCUGU

GCAAGCAGGGCGACAGCAUCAAGGCCUACGGCGCCGGCCUGCUGAGCAGC

UUCGGCGAGCUGCAGUACUGCCUGAGCGAGAAGCCCAAGCUGCUGCCCCU

GGAGCUGGAGAAGACCGCCAUCCAGAACUACACCGUGACCGAGUUCCAGC

CCCUGUACUACGUGGCCGAGAGCUUCAACGACGCCAAGGAGAAGGUGCGC

AACUUCGCCGCCACCAUCCCCCGCCCCUUCAGCGUGCGCUACGACCCCUA

CACCCAGCGCAUCGAGGUGCUGGACAACACCCAGCAGCUGAAGAUCCUGG

CCGACAGCAUCAACAGCGAGAUCGGCAUCCUGUGCAGCGCCCUGCAGAAG

AUCAAGUAA

In some embodiments, an mRNA suitable for the present invention has a nucleotide sequence at least 50%, 55%, 60%, 65%, 70%, 75%, 80%, 85%, 90%, 91%, 92%, 93%, 94%, 95%, 96%, 97%, 98%, 99% or more identical SEQ ID NO: 1, SEQ ID NO: 2, SEQ ID NO:3, SEQ ID NO: 4 or SEQ ID NO: 5. In some embodiments, an mRNA suitable for the present invention comprises a nucleotide sequence identical to SEQ ID NO: 1, SEQ ID NO: 2, SEQ ID NO:3, SEQ ID NO: 4 or SEQ ID NO: 5.

mRNA Solution mRNA Solution Properties mRNA may be provided as a solution to be mixed with a suspension of preformed empty LNPs such that the mRNA may be encapsulated in LNPs. A suitable mRNA solution may be any aqueous solution containing mRNA to be encapsulated at various concentrations. For example, a suitable mRNA solution may contain an mRNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable mRNA solution may contain an mRNA at a concentration ranging from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml. In some embodiments, a suitable mRNA solution may contain an mRNA at a concentration up to about 5.0 mg/ml, 4.0 mg/ml, 3.0 mg/ml, 2.0 mg/ml, 1.0 mg/ml, 0.09 mg/ml, 0.08 mg/ml, 0.07 mg/ml, 0.06 mg/ml, or 0.05 mg/ml.

A suitable mRNA solution may not contain a buffering agent and/or salt. For example, in a particular embodiment, the mRNA may be in RNase-free water, such as water for injection.

In some embodiments, a suitable mRNA solution may contain a buffering agent and/or salt. Generally, buffering agents can include HEPES, ammonium sulfate, sodium bicarbonate, sodium citrate, sodium acetate, potassium phosphate and sodium phosphate. In some embodiments, suitable concentration of the buffering agent may range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM. In some embodiments, suitable concentration of the buffering agent is or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM.

Exemplary salts can include sodium chloride, magnesium chloride, and potassium chloride. In some embodiments, suitable concentration of salts in an mRNA solution may range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM. Salt concentration in a suitable mRNA solution is or greater than about 1 mM, 5 mM, 10 mM, 20 mM, 30 mM, 40 mM, 50 mM, 60 mM, 70 mM, 80 mM, 90 mM, or 100 mM.

In some embodiments, a suitable mRNA solution may have a pH ranging from about 3.5-6.5, 3.5-6.0, 3.5-5.5., 3.5-5.0, 3.5-4.5, 4.0-5.5, 4.0-5.0, 4.0-4.9, 4.0-4.8, 4.0-4.7, 4.0-4.6, or 4.0-4.5. In some embodiments, a suitable mRNA solution may have a pH of or no greater than about 3.5, 4.0, 4.1, 4.2, 4.3, 4.4, 4.5, 4.6, 4.7, 4.8, 4.9, 5.0, 5.2, 5.4, 5.6, 5.8, 6.0, 6.1, 6.3, and 6.5.

Preparation of mRNA Solution

Various methods may be used to prepare an mRNA solution suitable for the present invention. In some embodiments, mRNA may be directly dissolved in a buffer solution described herein. In some embodiments, an mRNA solution may be generated by mixing an mRNA stock solution with a buffer solution prior to mixing with a suspension of preformed empty LNPs for encapsulation. In some embodiments, an mRNA solution may be generated by mixing an mRNA stock solution with a buffer solution immediately before mixing with a suspension of preformed empty LNPs for encapsulation. In some embodiments, a suitable mRNA stock solution may contain mRNA in water at a concentration at or greater than about 0.2 mg/ml, 0.4 mg/ml, 0.5 mg/ml, 0.6 mg/ml, 0.8 mg/ml, 1.0 mg/ml, 1.2 mg/ml, 1.4 mg/ml, 1.5 mg/ml, or 1.6 mg/ml, 2.0 mg/ml, 2.5 mg/ml, 3.0 mg/ml, 3.5 mg/ml, 4.0 mg/ml, 4.5 mg/ml, or 5.0 mg/ml.

Lipid Nanoparticles

Various processes can be used to prepare a suspension of pre-formed empty lipid nanoparticles or mRNA-encapsulating lipid nanoparticles for use with the methods disclosed herein. Typically, the first step in preparing such a suspension is to provide a lipid solution. As used herein, a lipid solution contains a mixture of lipids suitable to form lipid nanoparticles for encapsulation of mRNA.

Lipid Solutions

In some embodiments, a suitable lipid solution is ethanol based. For example, a suitable lipid solution may contain a mixture of desired lipids dissolved in pure ethanol (i.e., 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. For example, a suitable lipid solution may contain a mixture of desired lipids at a total concentration of or greater than about 0.1 mg/ml, 0.5 mg/ml, 1.0 mg/ml, 2.0 mg/ml, 3.0 mg/ml, 4.0 mg/ml, 5.0 mg/ml, 6.0 mg/ml, 7.0 mg/ml, 8.0 mg/ml, 9.0 mg/ml, 10 mg/ml, 15 mg/ml, 20 mg/ml, 30 mg/ml, 40 mg/ml, 50 mg/ml, or 100 mg/ml. In some embodiments, a suitable lipid solution may contain a mixture of desired lipids at a total concentration ranging from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9.0 mg/ml, 1.0-8.0 mg/ml, 1.0-7.0 mg/ml, 1.0-6.0 mg/ml, or 1.0-5.0 mg/ml. In some embodiments, a suitable lipid solution may contain a mixture of desired lipids at a total concentration up to about 100 mg/ml, 90 mg/ml, 80 mg/ml, 70 mg/ml, 60 mg/ml, 50 mg/ml, 40 mg/ml, 30 mg/ml, 20 mg/ml, or 10 mg/ml.

Any desired lipids may be mixed at any ratios suitable for encapsulating mRNAs. In some embodiments, a suitable lipid solution contains a mixture of desired lipids including cationic lipids, helper lipids (e.g. non cationic lipids and/or cholesterol lipids) and/or PEG-modified lipids. In some embodiments, a suitable lipid solution contains a mixture of desired lipids including a cationic lipid, one or more helper lipids (e.g. non cationic lipids and optionally cholesterol-based lipids) and a PEG-modified lipids.

Cationic Lipids

As used herein, the phrase "cationic lipids" refers to any of a number of lipid species that have a net positive charge at a selected pH, such as physiological pH, or under selected conditions, such as conditions under which the composition is formulated and/or administered. Several cationic lipids have been described in the literature, many of which are commercially available. Particularly suitable cationic lipids for use in the compositions and methods of the invention include those described in international patent publications WO 2010/053572 (and particularly, cationic lipids described as aminoalcohol lipidoids, more particularly C12-200 described at paragraph [00225]) and WO 2012/170930, both of which are incorporated herein by reference. In certain embodiments, cationic lipids suitable for the compositions and methods of the invention include an ionizable cationic lipid described in U.S. provisional patent application 61/617,468, filed Mar. 29, 2012 (corresponding to International Patent Application WO2013/149140—both incorporated herein by reference), such as, e.g, (15Z, 18Z)—N,N-dimethyl-6-((9Z, 12Z)-octadeca-9, 12-dien-1-yl)tetracosa-15,18-dien-1-amine (HGT5000), (15Z, 18Z)—N,N-dimethyl-6-((9Z, 12Z)-octadeca-9, 12-dien-1-yl)tetracosa-4, 15,18-trien-1-amine (HGT5001), and (15Z,18Z)—N,N-dimethyl-6-((9Z, 12Z)-octadeca-9, 12-dien-1-yl)tetracosa-5, 15, 18-trien-1-amine (HGT5002).

In some embodiments, cationic lipids suitable for the compositions and methods of the invention include cationic lipids such as 3,6-bis(4-(bis((9Z,12Z)-2-hydroxyoctadeca-9, 12-dien-1-yl)amino)butyl)piperazine-2,5-dione (OF-02).

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of:

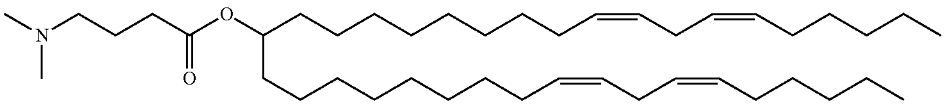 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

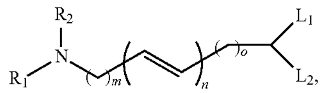

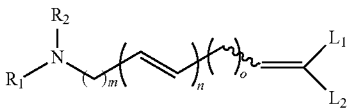

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)—N,N-dimethyl-6-((9Z,12Z)-octadeca-9,12-dien-1-yl) tetracosa-15,18-dien-1-amine ("HGT5000"), having a compound structure of:

(HGT-5000)

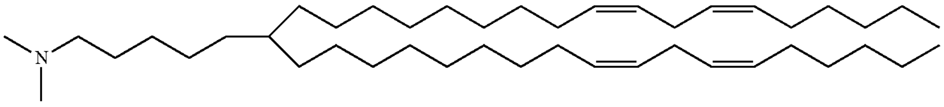

and pharmaceutically acceptable salts thereof. In certain embodiments, the compositions and methods of the present invention include the cationic lipid (15Z, 18Z)—N,N-dimethyl-6-((9Z,12Z)-octadeca-9,12-dien-1-yl) tetracosa-4,15,18-trien-1-amine ("HGT5001"), having a compound structure of:

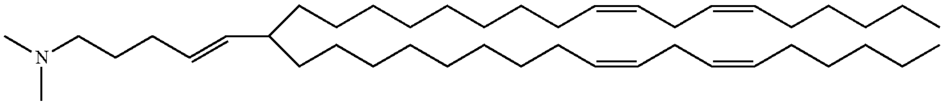

(HGT-5001)

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of:

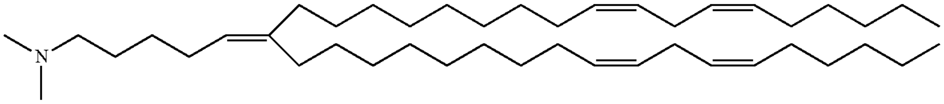

(HGT-5002)

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

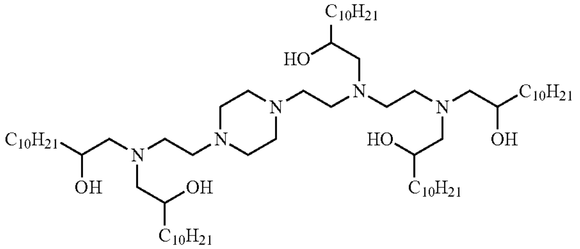

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

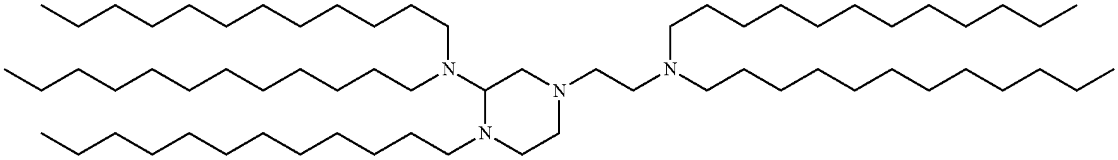 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

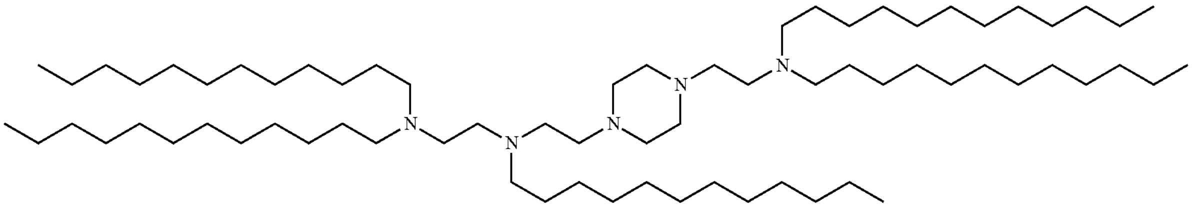 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

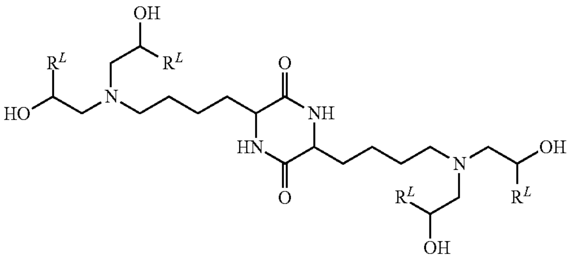

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

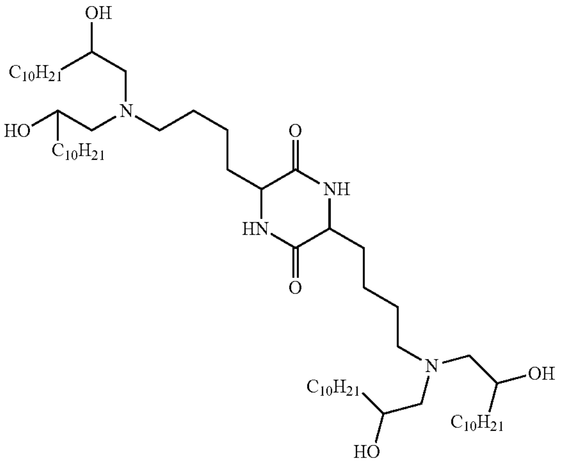

(cKK-E12; TBL-(0346))

and pharmaceutically acceptable salts thereof. In certain embodiments, the compositions and methods of the present invention include a cationic lipid having a compound structure of:

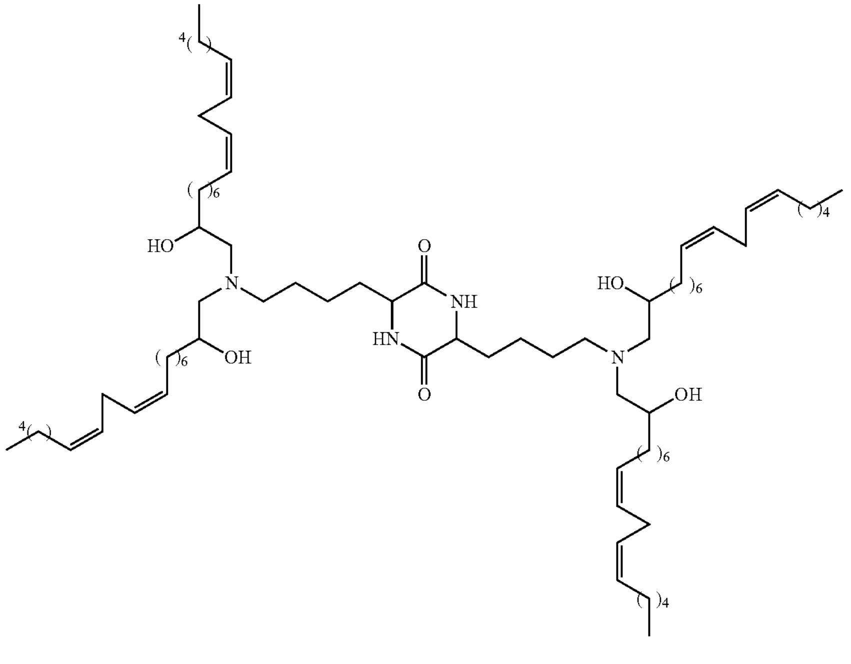

and pharmaceutically acceptable salts thereof. In certain embodiments, the compositions and methods of the present invention include a cationic lipid having a compound structure of:

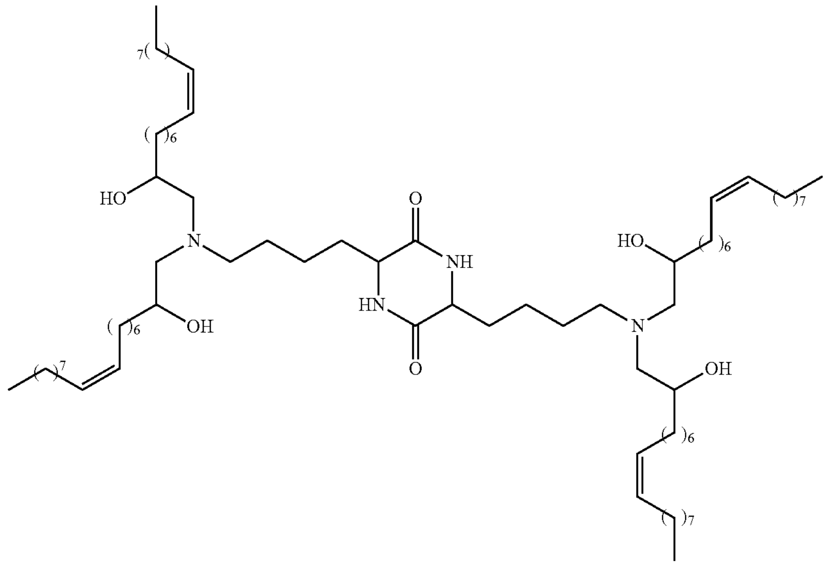

and pharmaceutically acceptable salts thereof. In certain embodiments, the compositions and methods of the present invention include a cationic lipid having a compound structure of:

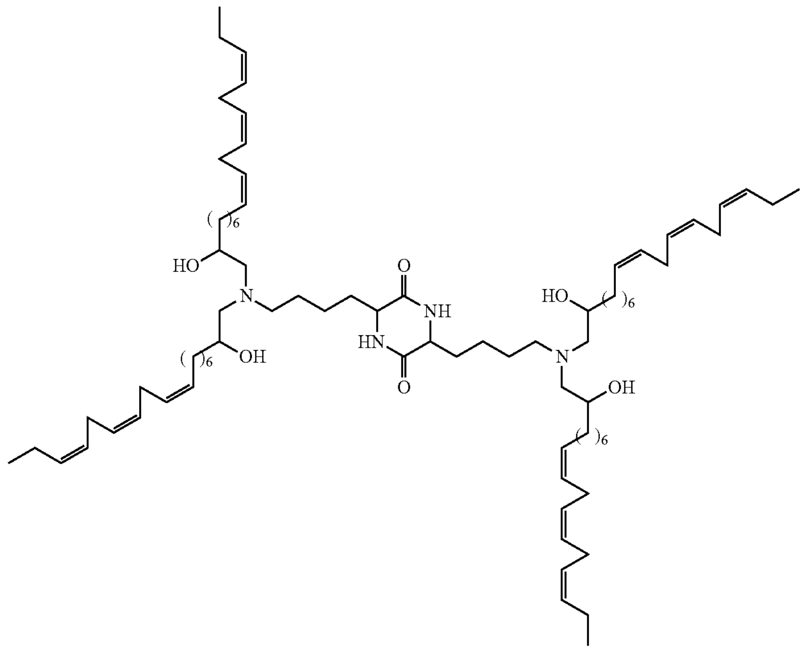

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

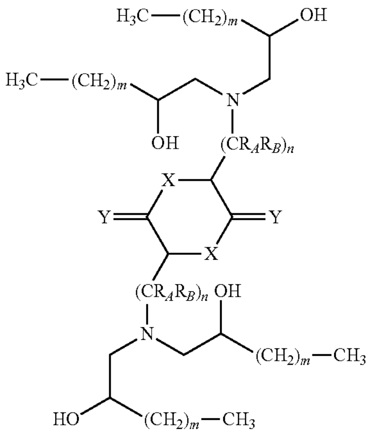

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

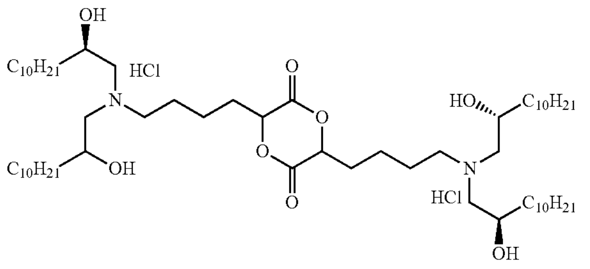

(Target 23)

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

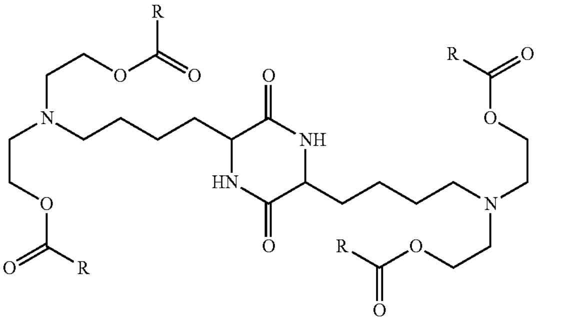

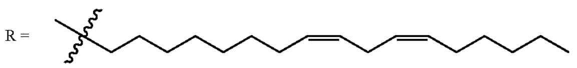

or a pharmaceutically acceptable salt thereof. In some embodiments, the compositions and methods of the present invention include a cationic lipid having the compound structure:

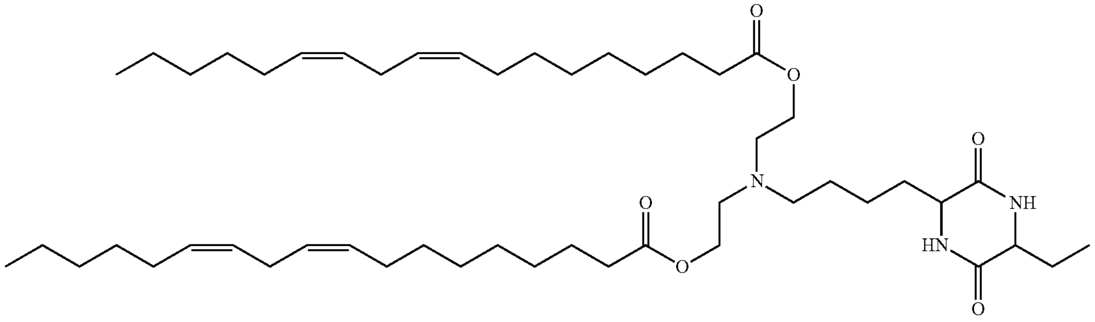 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

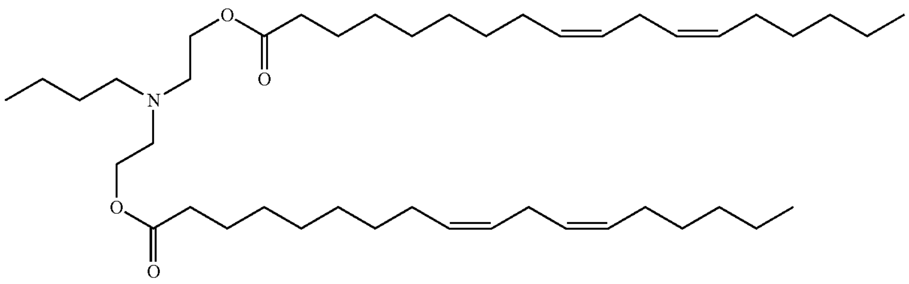 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include cationic lipids as described in U.S. Provisional Patent Application Ser. No. 62/758,179, filed on Nov. 9, 2018, and Provisional Patent Application Ser. No. 62/871,510, filed on Jul. 8, 2019, which are incorporated herein by reference. In some embodiments, the compositions and methods of the present invention include a cationic lipid of the following formula:

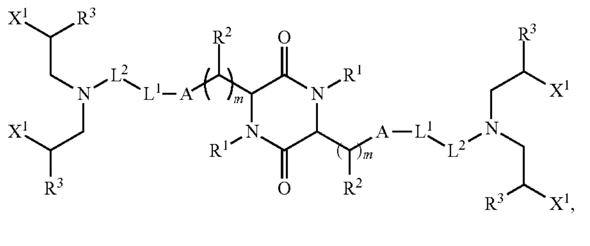

or a pharmaceutically acceptable salt thereof, wherein each $R^1$ and $R^2$ is independently H or $C_1$-$C_6$ aliphatic; each m is independently an integer having a value of 1 to 4; each A is independently a covalent bond or arylene; each $L^1$ is independently an ester, thioester, disulfide, or anhydride group; each $L^2$ is independently $C_2$-$C_{10}$ aliphatic; each $X^1$ is independently H or OH; and each $R^3$ is independently $C_6$-$C_{20}$ aliphatic. In some embodiments, the compositions and methods of the present invention include a cationic lipid of the following formula:

(Compound 1)

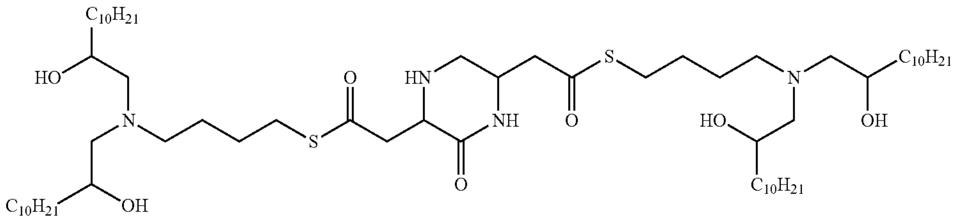

or a pharmaceutically acceptable salt thereof. In some embodiments, the compositions and methods of the present invention include a cationic lipid of the following formula:

(Compound 2; cHse-E-3-E10; TBL-0098)

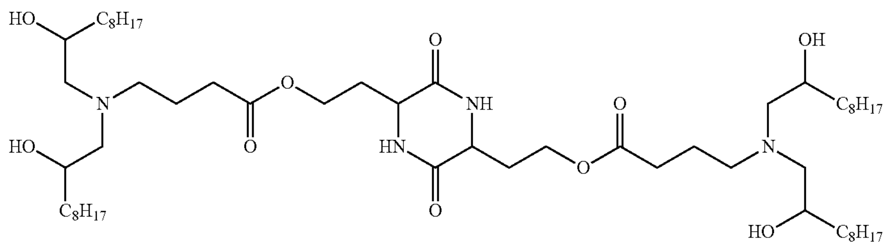

or a pharmaceutically acceptable salt thereof. In some embodiments, the compositions and methods of the present invention include a cationic lipid of the following formula:

(Compound 3)

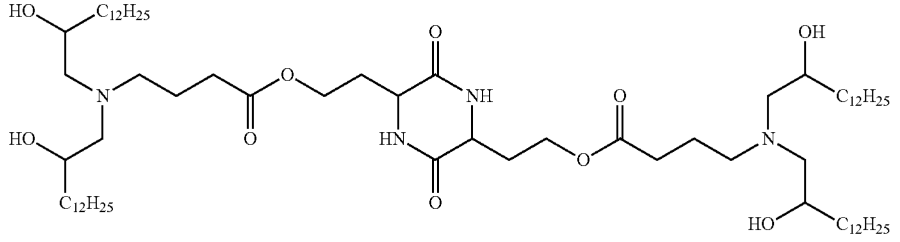

or a pharmaceutically acceptable salt thereof. In some embodiments, the compositions and methods of the present invention include a cationic lipid of the following formula:

(cDD-TE-4-E10)

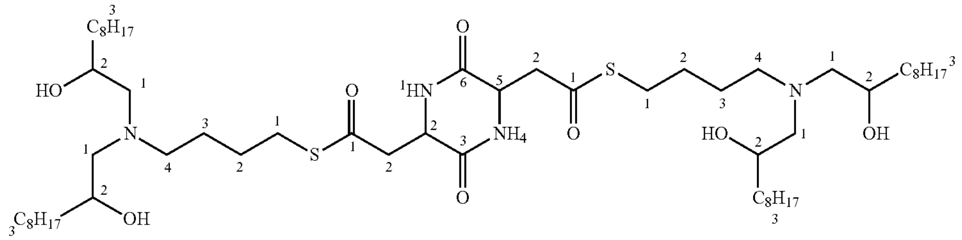

S,S-bis(4-(bis(2-hydroxydecyl)amino)butyl) 2,2′-(3,6-dioxopiperazine-2,5-diyl)diethanethioate and pharmaceutically acceptable salts thereof. In some embodiments, the compositions and methods of the present invention include a cationic lipid of the following formula:

(cDD-TE-4-E12)

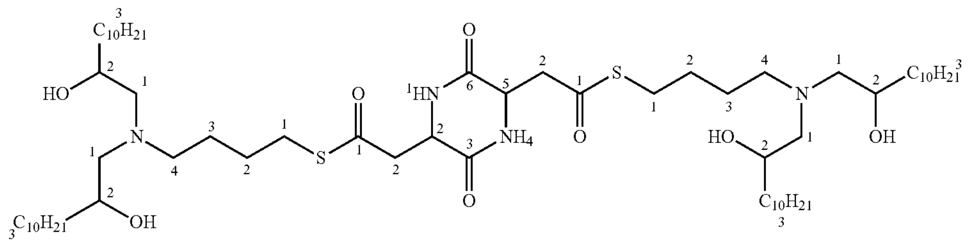

S,S-bis(4-(bis(2-hydroxydodecyl)amino)butyl) 2,2′-(3,6-dioxopiperazine-2,5-diyl)diethanethioate and pharmaceutically acceptable salts thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which are incorporated herein by reference. In certain embodiments, the cationic lipids of the compositions and methods of the present invention include a cationic lipid having a compound structure of:

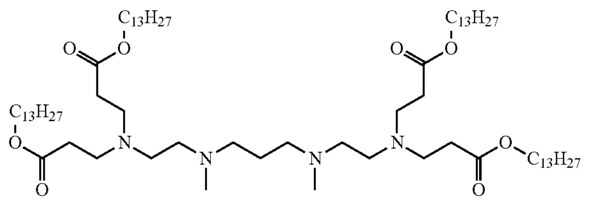

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

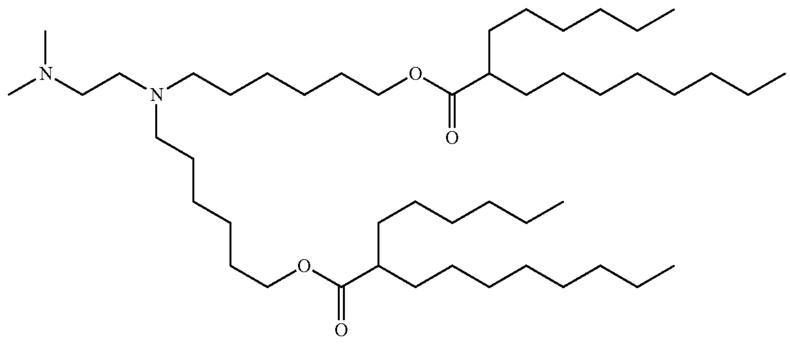 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

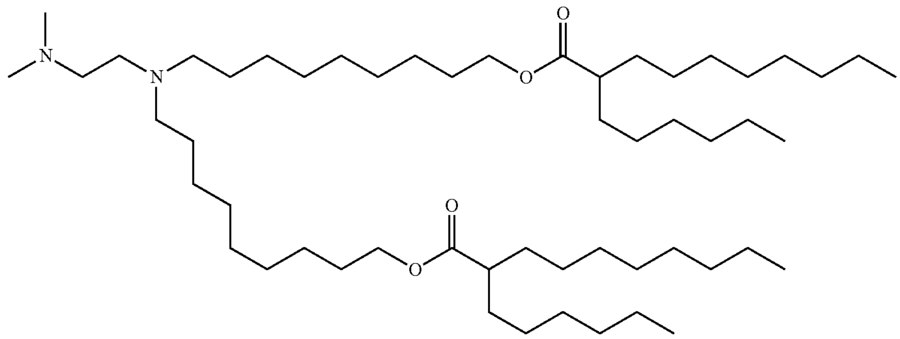 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

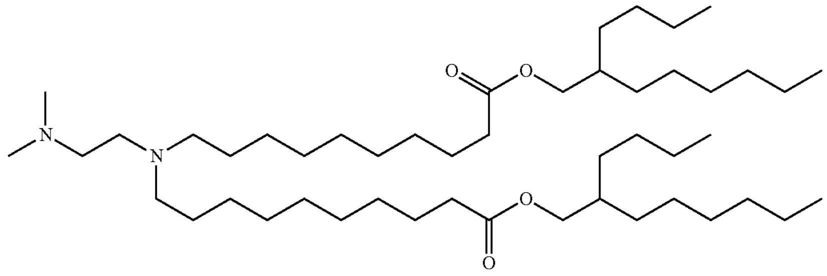 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

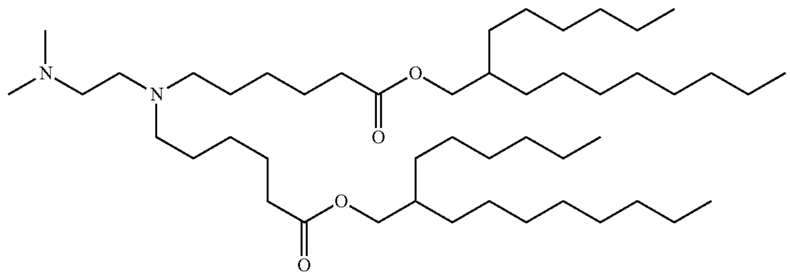 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

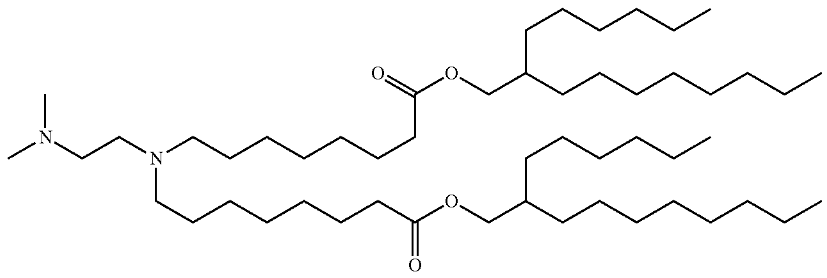 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

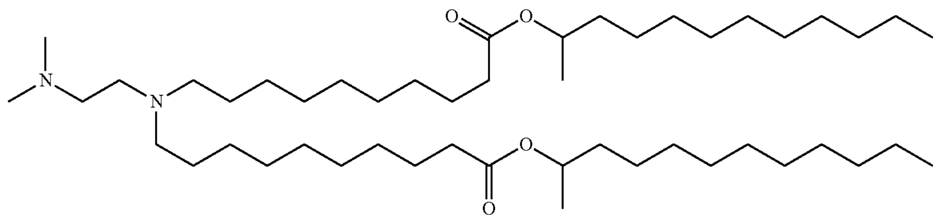 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

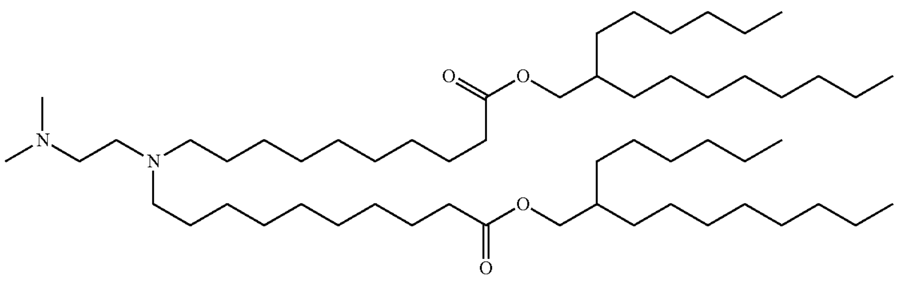 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

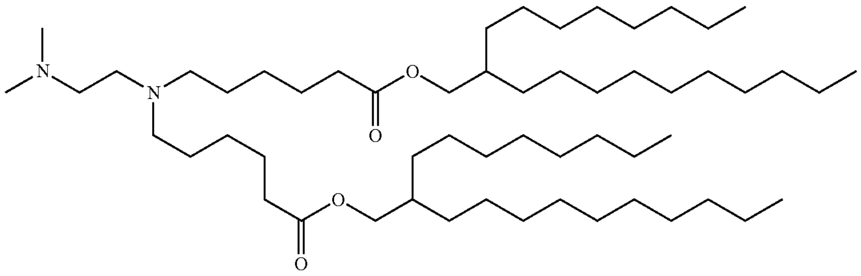 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

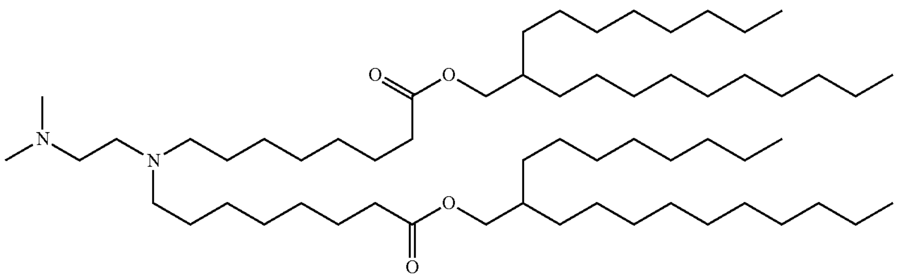 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

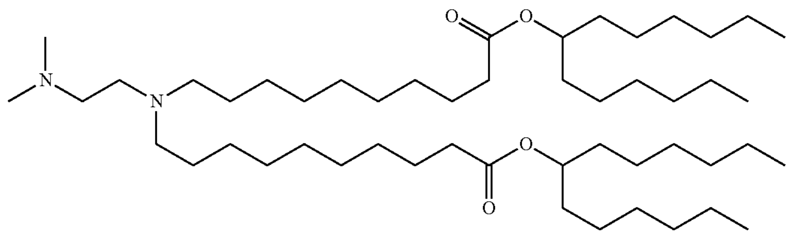 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

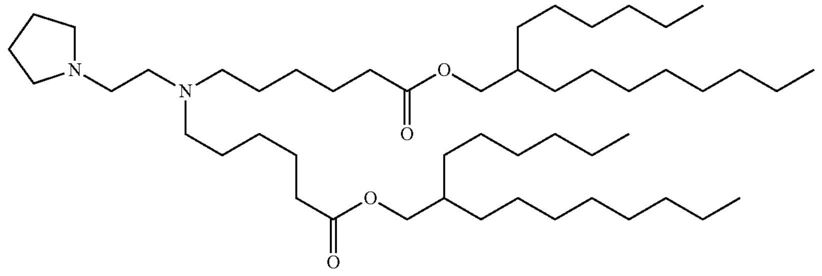 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

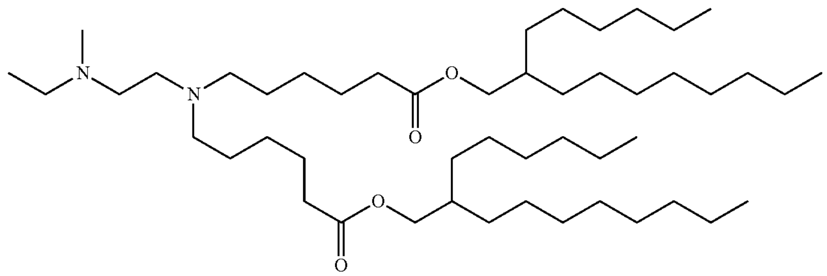 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

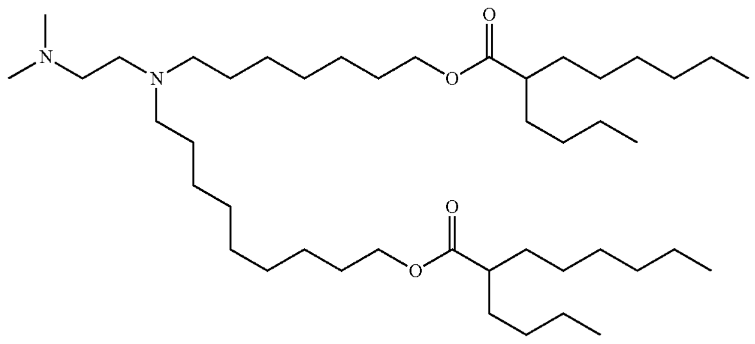 [SMILES: CCCCCCC(CCCC)C(=O)OCCCCCCCCCN(CCCCCCCOC(=O)C(CCCC)CCCCCC)CCN(C)C]

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

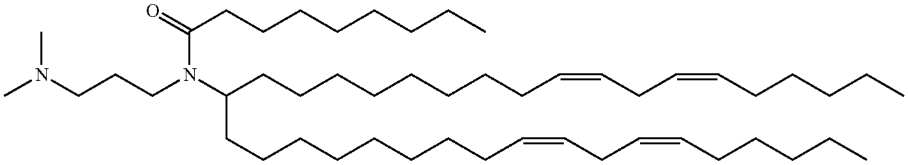 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

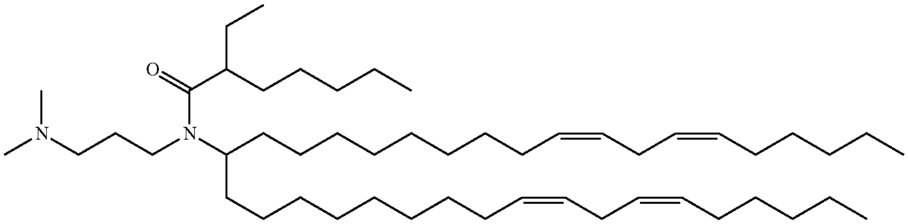 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

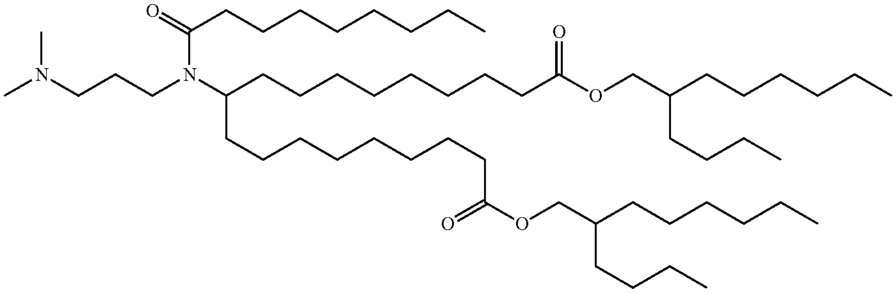 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

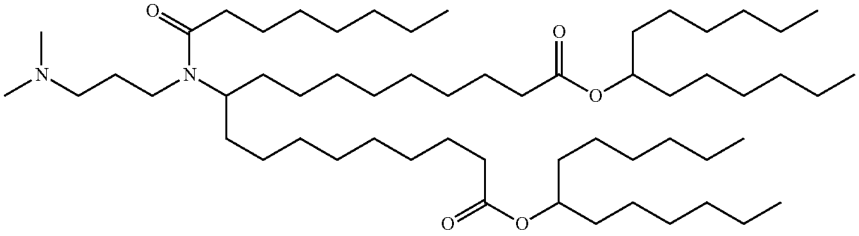 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

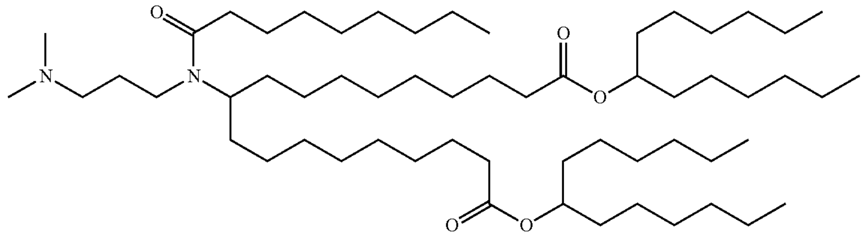 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

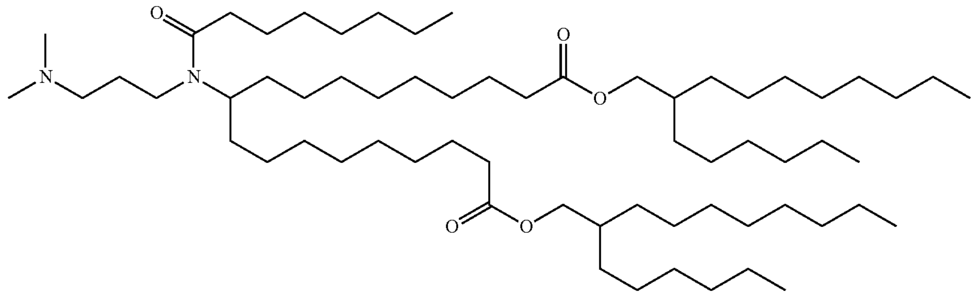 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

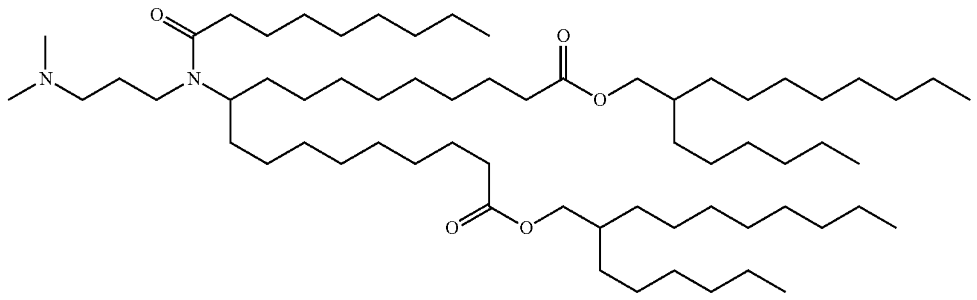 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

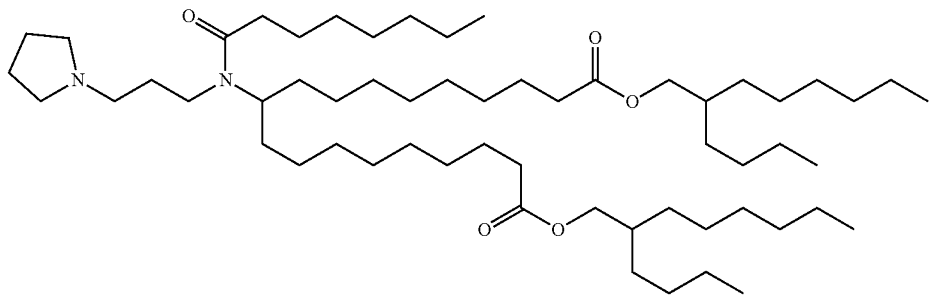 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

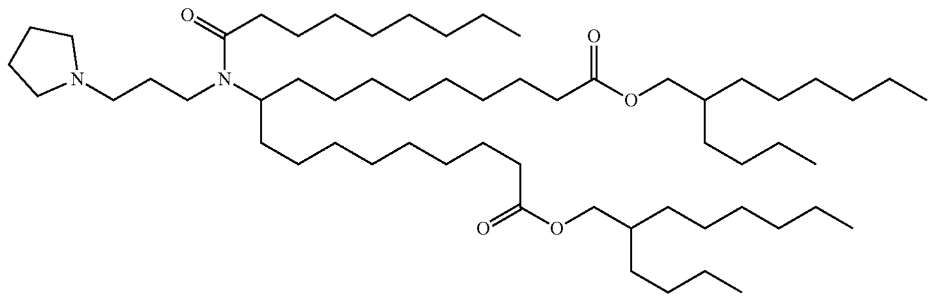 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

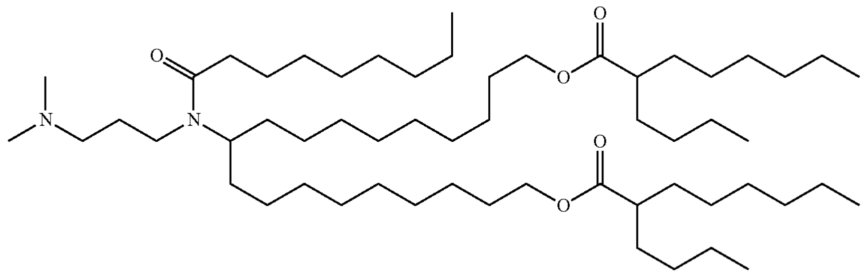 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

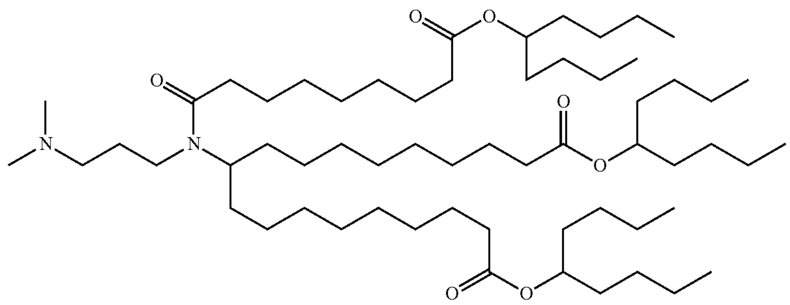 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC]

and pharmaceutically acceptable salts thereof. In some embodiments, the compositions and methods of the present invention include a cationic lipid having the compound structure:

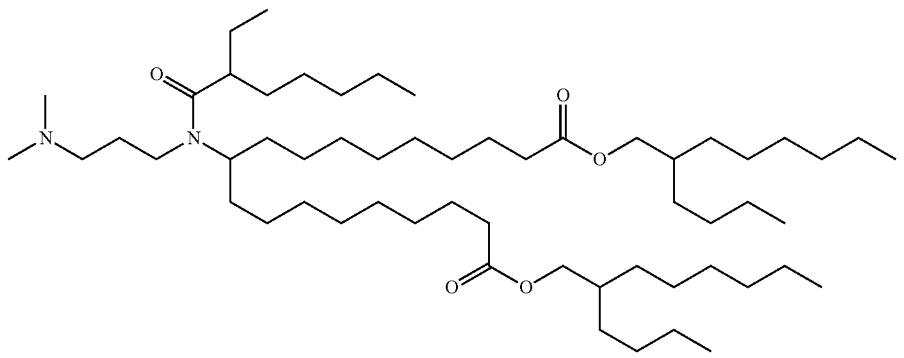 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

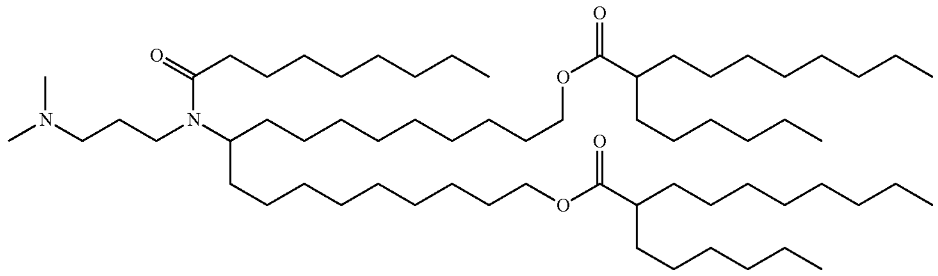 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

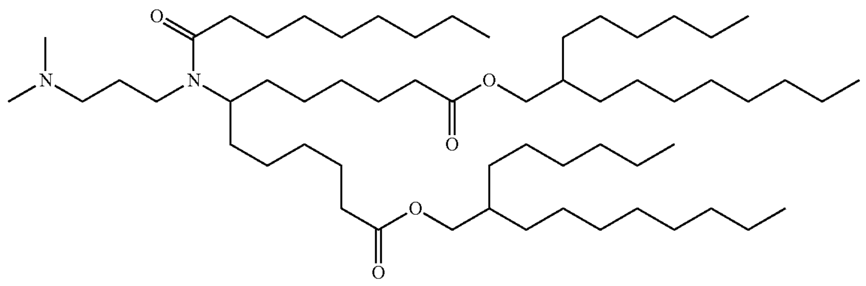 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

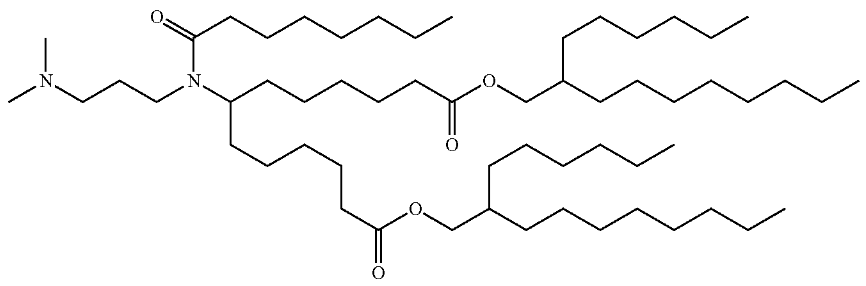 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

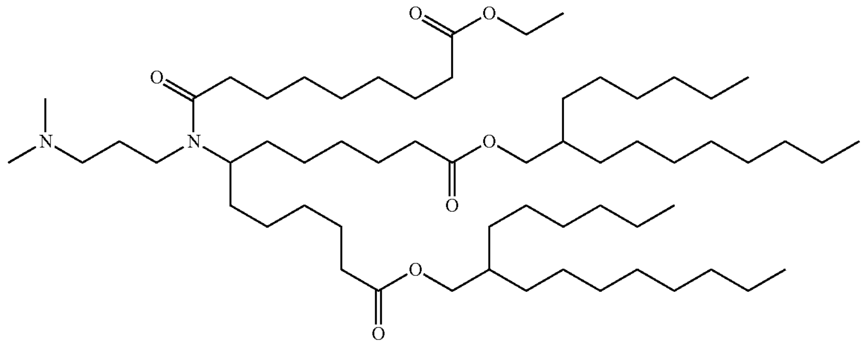 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

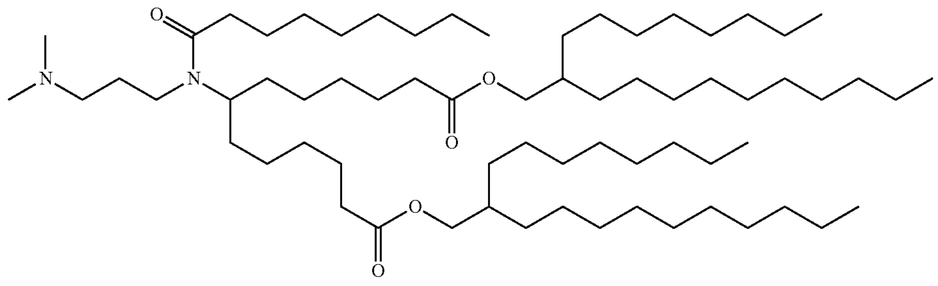 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

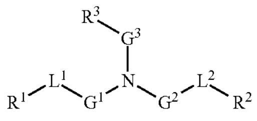

or a pharmaceutically acceptable salt thereof, wherein one of $L^1$ or $L^2$ is —O(C=O)—, —(C=O)O—, —C(═O)—, —O—, —S(O)$_x$, —S—S—, —C(═O)S—, —SC(═O)—, —NRaC(═O)—, —C(═O)NR$^a$—, NR$^a$C(═O)NR$^a$—, —OC(═O)NR$^a$—, or —NR$^a$C(═O)O—; and the other of $L^1$ or $L^2$ is —O(C=O)—, —(C=O)O—, —C(═O)—, —O—, —S(O)$_x$, —S—S—, —C(═O)S—, SC(═O)—, —NRaC(═O)—, —C(═O)NR$^a$—, NR$^a$C(═O)NR$^a$—, —OC(═O)NR$^a$— or —NR$^a$C(═O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, $OR^5$, CN, —C(═O)OR$^4$, —OC(═O)R$^4$ or —NR$^5$C(═O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

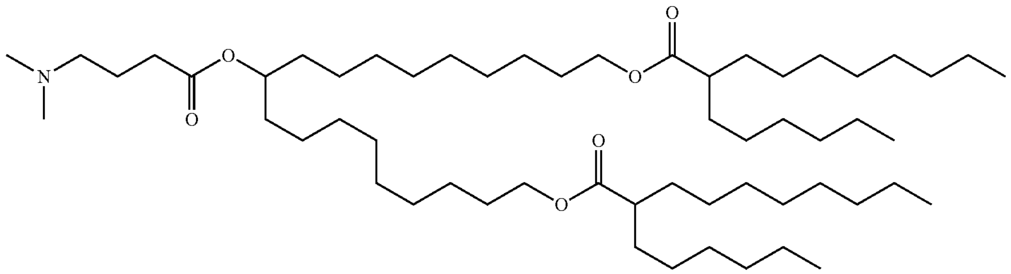 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

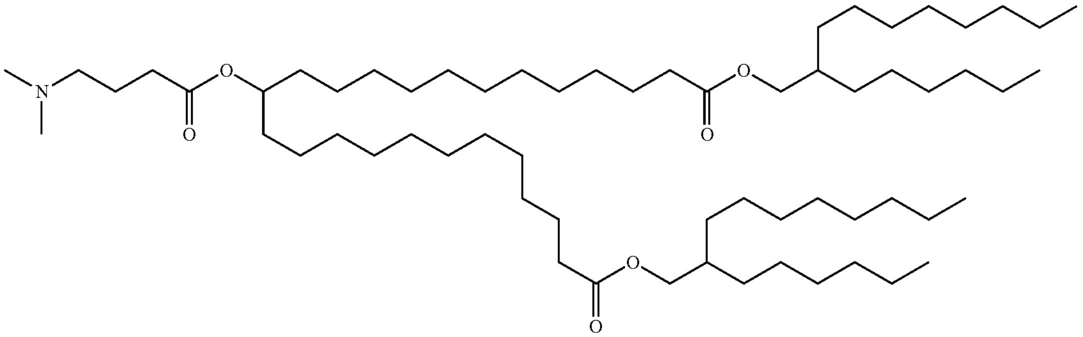 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

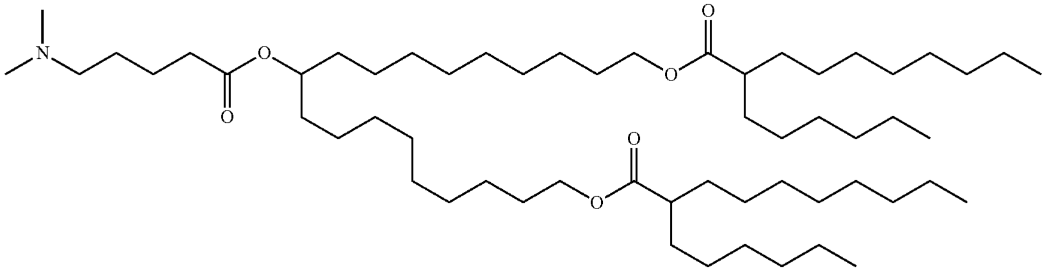 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

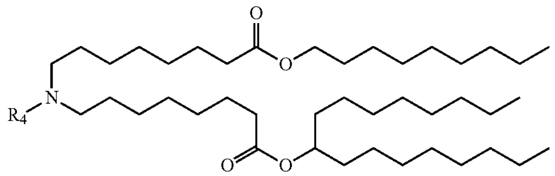

,

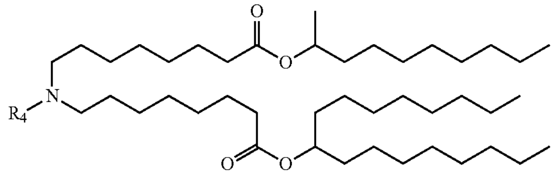

,

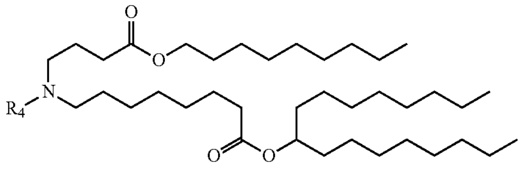

, and

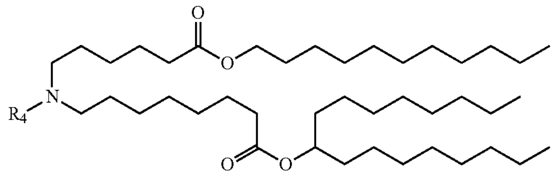

, and pharmaceutically acceptable salts thereof. For any one of these four formulas, $R_4$ is independently selected from —$(CH_2)_nQ$ and —$(CH_2)_nCHQR$; Q is selected from the group consisting of —OR, —OH, —$O(CH_2)_nN(R)_2$, —OC(O)R, —$CX_3$, —CN, —N(R)C(O)R, —N(H)C(O)R, —$N(R)S(O)_2R$, —$N(H)S(O)_2R$, —$N(R)C(O)N(R)_2$, —$N(H)C(O)N(R)_2$, —N(H)C(O)N(H)(R), —$N(R)C(S)N(R)_2$, —$N(H)C(S)N(R)_2$, —N(H)C(S)N(H)(R), and a heterocycle; and n is 1, 2, or 3. In certain embodiments, the compositions and methods of the present invention include a cationic lipid having a compound structure of:

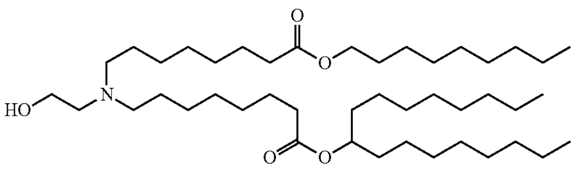 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

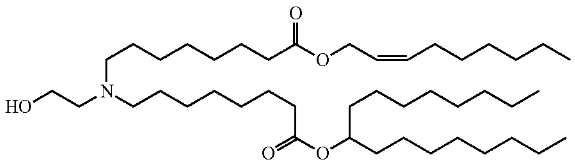 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

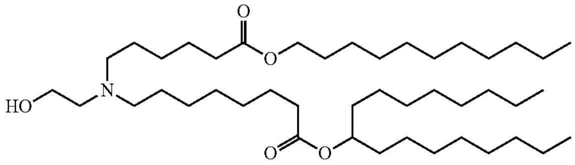 [SMILES: CCCCCCCCCCCOC(=O)CCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

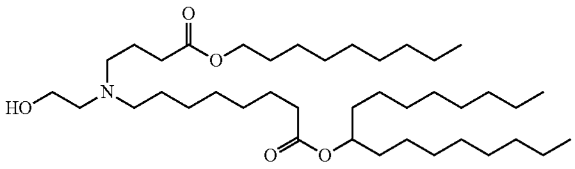 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

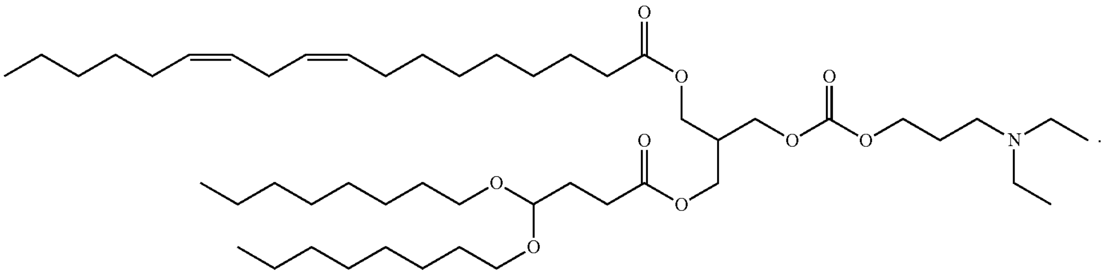 [SMILES: CCCCC/C=C\C/C=C\CCCCCCCC(=O)OCC(COC(=O)CCC(OCCCCCCCC)OCCCCCCCC)COC(=O)OCCCN(CC)CC]

and pharmaceutically acceptable salts thereof. In certain embodiments, the compositions and methods of the present invention include a cationic lipid having a compound structure of:

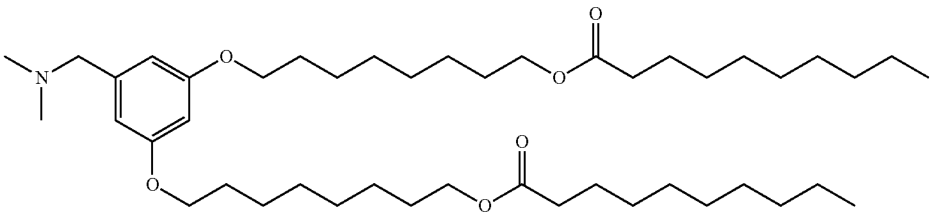 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

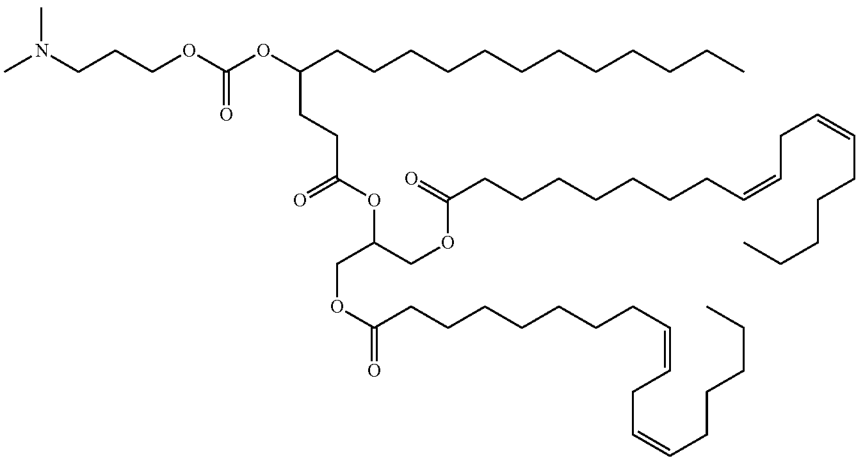 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

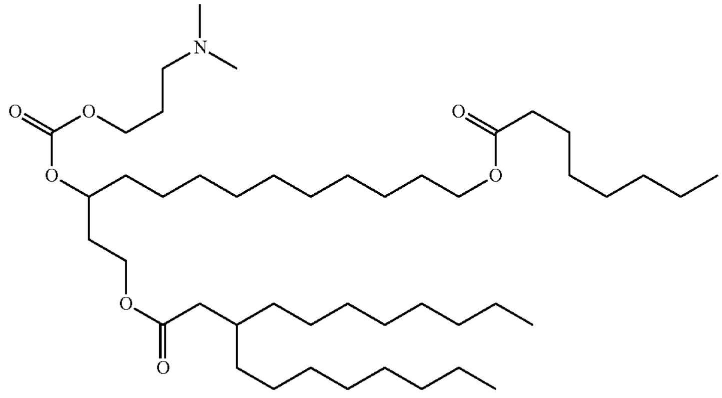 [SMILES: CCCCCCCCC(CCCCCCCC)CC(=O)OCCC(CCCCCCCCCCOC(=O)CCCCCCC)OC(=O)OCCCN(C)C]

and pharmaceutically acceptable salts thereof.

Other suitable cationic lipids for use in the pharmaceutical compositions and methods of the present invention include cationic lipids as described in U.S. Provisional Patent Application Ser. No. 62/865,555, filed on Jun. 24, 2019, which is incorporated herein by reference. In some embodiments, the pharmaceutical compositions and methods of the present invention include a cationic lipid having a compound structure of:

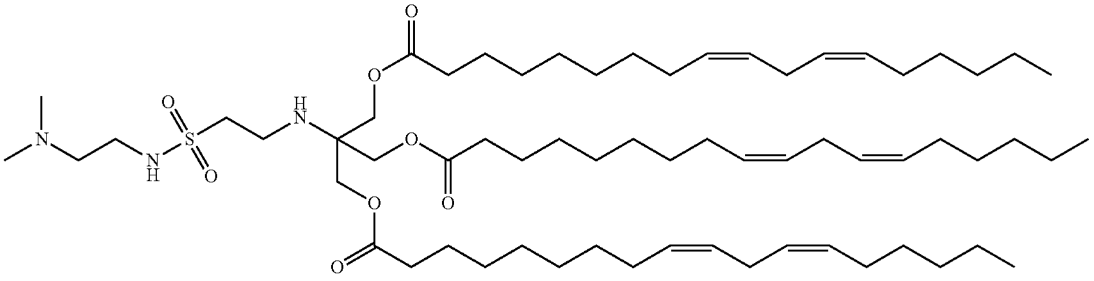

(GL-TES-SA-DME-E18-2; TBL-0132)

and pharmaceutically acceptable salts thereof.

Other suitable cationic lipids for use in the pharmaceutical compositions and methods of the present invention include cationic lipids as described in U.S. Provisional Patent Application Ser. No. 62/864,818, filed on Jun. 21, 2019, which is incorporated herein by reference. In some embodiments, the pharmaceutical compositions and methods of the present invention include a cationic lipid having a compound structure according to the following formula:

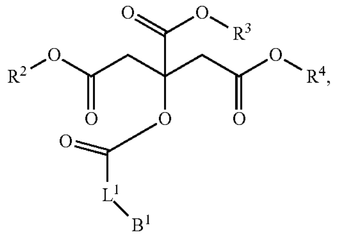

or a pharmaceutically acceptable salt thereof, wherein each of $R^2$, $R^3$, and $R^4$ is independently $C_6$-$C_{30}$ alkyl, $C_6$-$C_{30}$ alkenyl, or $C_6$-$C_{30}$ alkynyl; $L^1$ is $C_1$-$C_{30}$ alkylene; $C_2$-$C_{30}$ alkenylene; or $C_2$-$C_{30}$ alkynylene and $B^1$ is an ionizable nitrogen-containing group. In embodiments, $L^1$ is $C_1$-$C_{10}$ alkylene. In embodiments, $L^1$ is unsubstituted $C_1$-$C_{10}$ alkylene. In embodiments, $L^1$ is $(CH_2)_2$, $(CH_2)_3$, $(CH_2)_4$, or $(CH_2)_5$. In embodiments, $L^1$ is $(CH_2)$, $(CH_2)_6$, $(CH_2)_7$, $(CH_2)_8$, $(CH_2)_9$, or $(CH_2)_{10}$. In embodiments, $B^1$ is independently $NH_2$, guanidine, amidine, a mono- or dialkylamine, 5- to 6-membered nitrogen-containing heterocycloalkyl, or 5- to 6-membered nitrogen-containing heteroaryl. In embodiments, $B^1$ is

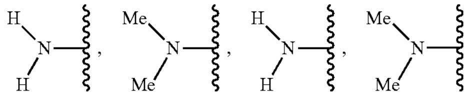

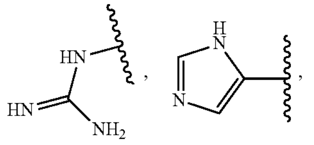

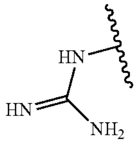

or

-continued

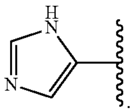

In embodiments, $B^1$ is

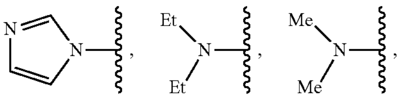

or

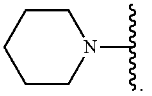

In embodiments, $B^1$ is

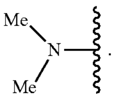

In embodiments, each of $R^2$, $R^3$, and $R^4$ is independently unsubstituted linear $C_6$-$C_{22}$ alkyl, unsubstituted linear $C_6$-$C_{22}$ alkenyl, unsubstituted linear $C_6$-$C_{22}$ alkynyl, unsubstituted branched $C_6$-$C_{22}$ alkyl, unsubstituted branched $C_6$-$C_{22}$ alkenyl, or unsubstituted branched $C_6$-$C_{22}$ alkynyl. In embodiments, each of $R^2$, $R^3$, and $R^4$ is unsubstituted $C_6$-$C_{22}$ alkyl. In embodiments, each of $R^2$, $R^3$, and $R^4$ is $—C_6H_{13}$, $—C_7H_{15}$, $—C_8H_{17}$, $—C_9H_{19}$, $—C_{10}H_{21}$, $—C_{11}H_{23}$, $—C_{12}H_{25}$, $—C_{13}H_{27}$, $—C_{14}H_{29}$, $—C_{15}H_{31}$, $—C_{16}H_{33}$, $—C_{17}H_{35}$, $—C_{18}H_{37}$, $—C_{19}H_{39}$, $—C_{20}H_{41}$, $—C_{21}H_{43}$, $—C_{22}H_{45}$, $—C_{23}H_{47}$, $—C_{24}H_{49}$, or $—C_{25}H_{51}$. In embodiments, each of $R^2$, $R^3$, and $R^4$ is independently $C_6$-$C_{12}$ alkyl substituted by $—O(CO)R^5$ or $—C(O)OR^5$, wherein $R^5$ is unsubstituted $C_6$-$C_{14}$ alkyl. In embodiments, each of $R^2$, $R^3$, and $R^4$ is unsubstituted $C_6$-$C_{22}$ alkenyl. In embodiments, each of $R^2$, $R^3$, and $R^4$ is $—(CH_2)_4CH═CH_2$, $—(CH_2)_5CH═CH_2$, $—(CH_2)_6CH═CH_2$, $—(CH_2)_7CH═CH_2$, $—(CH_2)_8CH═CH_2$, $—(CH_2)_9CH═CH_2$, $—(CH_2)_{10}CH═CH_2$, $—(CH_2)_{11}CH═CH_2$, $—(CH_2)_{12}CH═CH_2$, $—(CH_2)_{13}CH═CH_2$, $—(CH_2)_{14}CH═CH_2$, $—(CH_2)_{15}CH═CH_2$, $—(CH_2)_{16}CH═CH_2$, $—(CH_2)_{17}CH═CH_2$, $—(CH_2)_{18}CH═CH_2$, $—(CH_2)_7CH═CH(CH_2)_3CH_3$, $—(CH_2)_7CH═CH(CH_2)_5CH_3$, $—(CH_2)_4CH═CH(CH_2)_8CH_3$, $—(CH_2)_7CH═CH(CH_2)_7CH_3$, $—(CH_2)_6CH═CHCH_2CH═CH(CH_2)_4CH_3$, $—(CH_2)_7CH═CHCH_2CH═CH(CH_2)_4CH_3$, $—(CH_2)_7CH═CHCH_2CH═CHCH_2CH═CHCH_2CH_3$, $—(CH_2)_3CH═CHCH_2CH═CHCH_2CH═CHCH_2CH═CH(CH_2)_4CH_3$, $—(CH_2)_3CH═CHCH_2CH═CHCH_2CH═CHCH_2CH═CHCH_2CH═CHCH_2CH_3$, $—(CH_2)_{11}CH═CH(CH_2)_7CH_3$, or $—(CH_2)_2CH═CHCH_2CH═CHCH_2CH═CHCH_2CH═CHCH_2CH═CHCH_2CH═CHCH_2CH_3$.

In embodiments, said $C_6$-$C_{22}$ alkenyl is a monoalkenyl, a dienyl, or a trienyl. In embodiments, each of $R^2$, $R^3$, and $R^4$ is

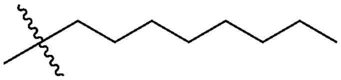
;
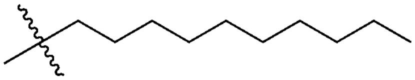
;
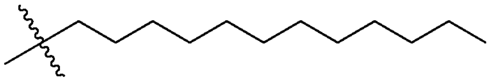
;
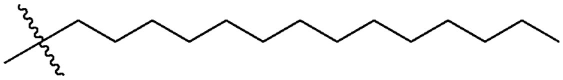
;
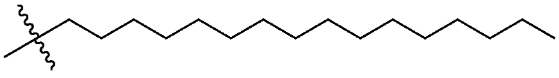
;
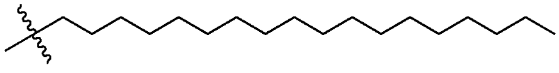
;
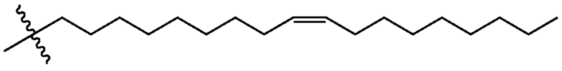
;
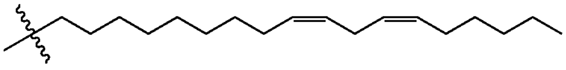
;
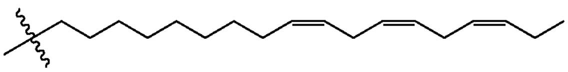
;
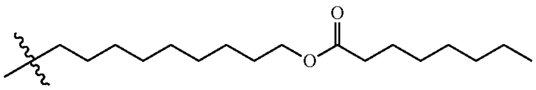
; or
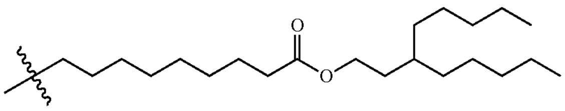
.

In some embodiments, the pharmaceutical compositions and methods of the present invention include a cationic lipid having a compound structure of:

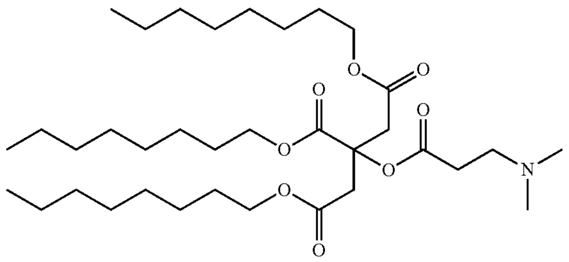

(TL1-01D-DMA; TBL-0134)

and pharmaceutically acceptable salts thereof. In some embodiments, the pharmaceutical compositions and methods of the present invention include a cationic lipid having a compound structure of:

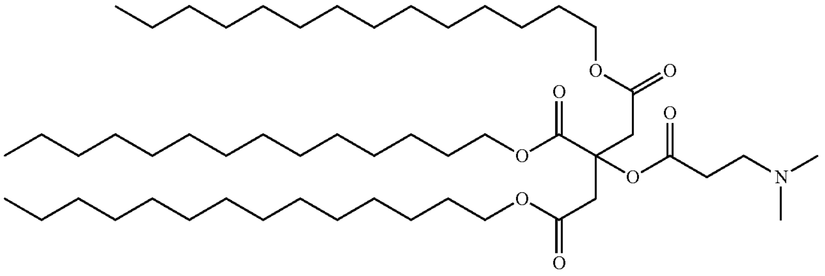

(TL1-04D-DMA; TBL-0227)

and pharmaceutically acceptable salts thereof. In some embodiments, the pharmaceutical compositions and methods of the present invention include a cationic lipid having a compound structure of:

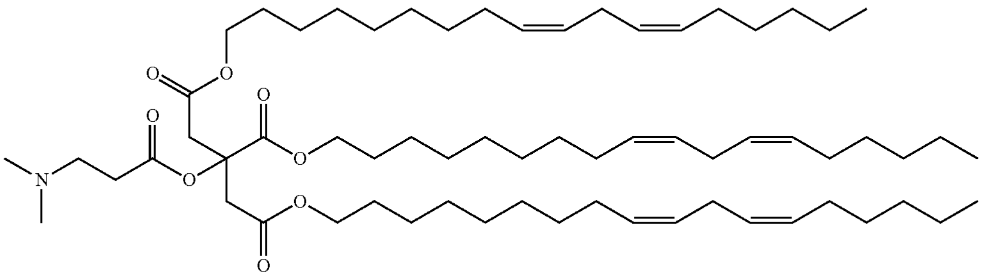

(TL1-08D-DMA; TBL-0245)

and pharmaceutically acceptable salts thereof. In some embodiments, the pharmaceutical compositions and methods of the present invention include a cationic lipid having a compound structure of:

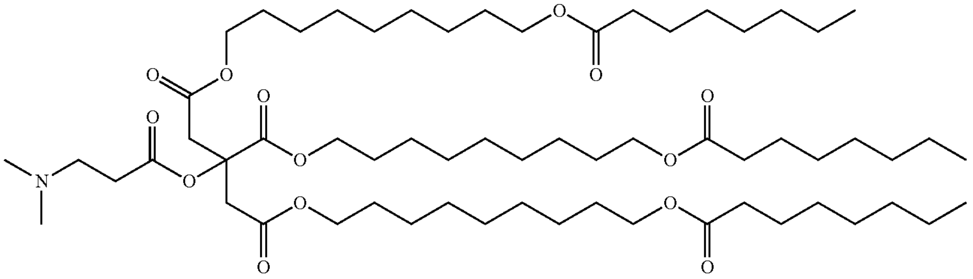

(TL1-10D-DMA; TBL-0246)

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

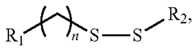

and pharmaceutically acceptable salts thereof, wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

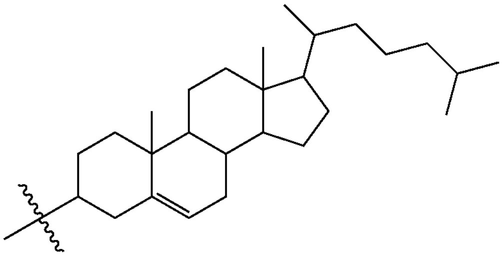

and

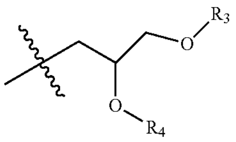

and pharmaceutically acceptable salts thereof, and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, “HGT4001”, having a compound structure of:

(HGT4001; TBL-0279)

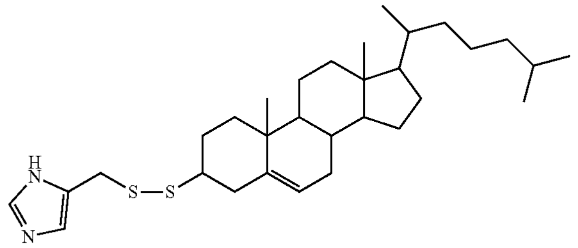

and pharmaceutically acceptable salts thereof. In certain embodiments, the compositions and methods of the present invention include a cationic lipid, “HGT4002,” having a compound structure of:

(HGT4002; TBL-0279)

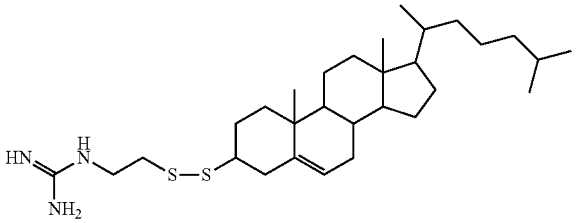

and pharmaceutically acceptable salts thereof. In certain embodiments, the compositions and methods of the present invention include a cationic lipid, “HGT4003,” having a compound structure of:

(HGT4003)

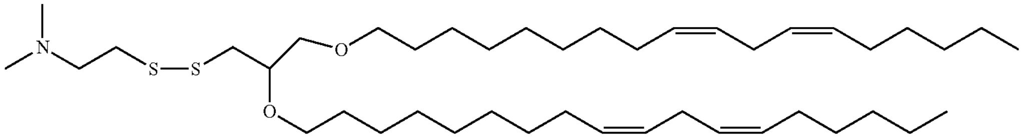

and pharmaceutically acceptable salts thereof. In certain embodiments, the compositions and methods of the present invention include a cationic lipid, “HGT4004,” having a compound structure of:

(HGT4004)

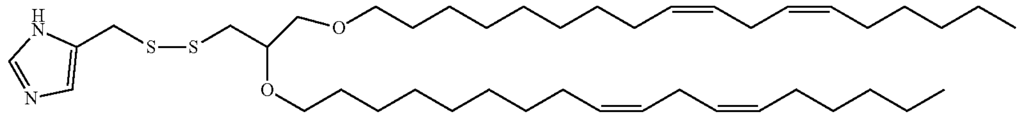

and pharmaceutically acceptable salts thereof. In certain embodiments, the compositions and methods of the present invention include a cationic lipid “HGT4005,” having a compound structure of:

(HGT4005)

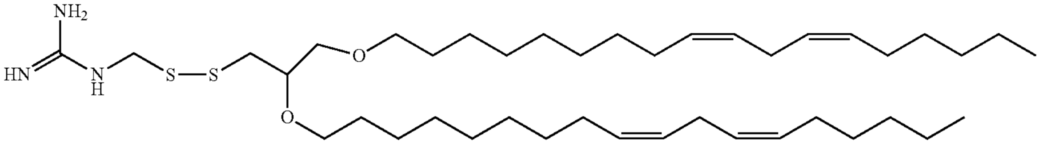

and pharmaceutically acceptable salts thereof.

Other suitable cationic lipids for use in the compositions and methods of the present invention include cleavable cationic lipids as described in Patent Publication WO 2019/222424, and incorporated herein by reference. In certain embodiments, the compositions and methods of the present invention include a cationic lipid that is any of general formulas or any of structures (1a)-(21a) and (1b)-(21b) and (22)-(237) described in Patent Publication WO 2019/222424. In certain embodiments, the compositions and methods of the present invention include a cationic lipid that has a structure according to Formula (I'), (I')

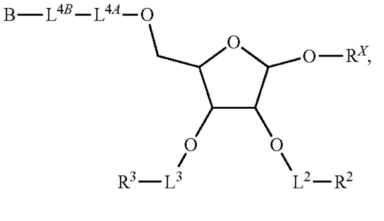

and pharmaceutically acceptable salts thereof, wherein:

$R^X$ is independently —H, $-L^1-R^1$, or $-L^{5A}-L^{5B}-B'$;

each of $L^1$, $L^2$, and $L^3$ is independently a covalent bond, —C(O)—, —C(O)O—, —C(O)S—, or —C(O)$NR^L$—;

each $L^{4A}$ and $L^{5A}$ is independently —C(O)—, —C(O)O—, or —C(O)$NR^L$—;

each $L^{4B}$ and $L^{5B}$ is independently $C_1$-$C_{20}$ alkylene; $C_2$-$C_{20}$ alkenylene; or $C_2$-$C_{20}$ alkynylene;

each B and B' is $NR^4R^5$ or a 5- to 10-membered nitrogen-containing heteroaryl;

each $R^1$, $R^2$, and $R^3$ is independently $C_6$-$C_{30}$ alkyl, $C_6$-$C_{30}$ alkenyl, or $C_6$-$C_{30}$ alkynyl;

each $R^4$ and $R^5$ is independently hydrogen, $C_1$-$C_{10}$ alkyl; $C_2$-$C_{10}$ alkenyl; or $C_2$-$C_{10}$ alkynyl; and each $R^L$ is independently hydrogen, $C_1$-$C_{20}$ alkyl, $C_2$-$C_{20}$ alkenyl, or $C_2$-$C_{20}$ alkynyl.

In certain embodiments, the compositions and methods of the present invention include a cationic lipid that is Compound (139) of Patent Publication WO 2019/222424, having a compound structure of:

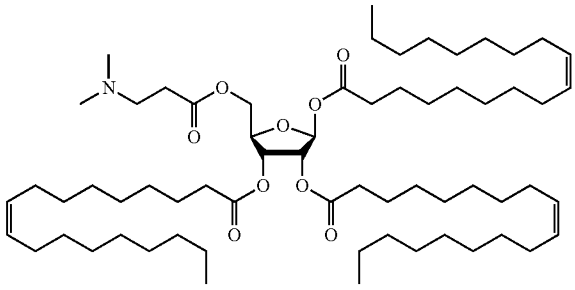

("18:1 Carbon tail-ribose lipid")

and pharmaceutically acceptable salts thereof.

In some embodiments, the pharmaceutical compositions and methods of the present invention include a cationic lipid that is TBL-0070 (RL3-DMA-07D) having a compound structure of:

(RL3-DMA-07D; TBL-0070)

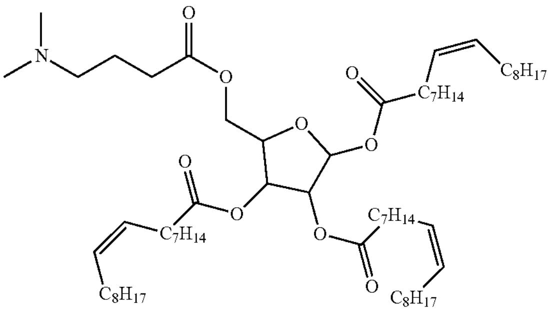

and pharmaceutically acceptable salts thereof.

In some embodiments, cationic lipids suitable for the compositions and methods of the invention include a cationic lipid described in WO 2015/184256 A2 entitled "Biodegradable lipids for delivery of nucleic acids" which is incorporated by reference herein such as 3-(4-(bis(2-hydroxydodecyl)amino)butyl)-6-(4-((2-hydroxydodecyl)(2-hydroxyundecyl)amino)butyl)-1,4-dioxane-2,5-dione (Target 23), 3-(5-(bis(2-hydroxydodecyl)amino)pentan-2-yl)-6-(5-((2-hydroxydodecyl)(2-hydroxyundecyl)amino)pentan-2-yl)-1,4-dioxane-2,5-dione (Target 24).

In some embodiments, cationic lipids suitable for the compositions and methods of the invention include a cationic lipid described in WO 2013/063468 and in U.S. provisional application entitled "Lipid Formulations for Delivery of Messenger RNA" and in WO 2015/061467, both of which are incorporated by reference herein. In some embodiments, a cationic lipid comprises a compound of formula I-c1-a:

I-c1-a

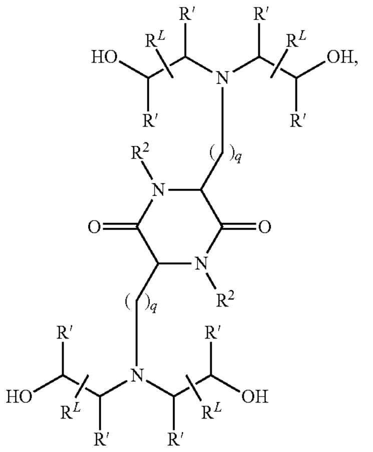

or a pharmaceutically acceptable salt thereof, wherein:

each $R^2$ independently is hydrogen or $C_{1-3}$ alkyl;

each q independently is 2 to 6;

each R' independently is hydrogen or $C_{1-3}$ alkyl;

and each $R^L$ independently is $C_{8-12}$ alkyl.

In some embodiments, each $R^2$ independently is hydrogen, methyl or ethyl. In some embodiments, each $R^2$ independently is hydrogen or methyl. In some embodiments, each $R^2$ is hydrogen.

In some embodiments, each q independently is 3 to 6. In some embodiments, each q independently is 3 to 5. In some embodiments, each q is 4.

In some embodiments, each R' independently is hydrogen, methyl or ethyl. In some embodiments, each R' independently is hydrogen or methyl. In some embodiments, each R' independently is hydrogen.

In some embodiments, each $R^L$ independently is $C_{8-12}$ alkyl. In some embodiments, each $R^L$ independently is n-$C_{812}$ alkyl. In some embodiments, each $R^L$ independently is $C_{9-11}$ alkyl. In some embodiments, each $R^L$ independently is n-$C_{911}$ alkyl. In some embodiments, each $R^L$ independently is $C_{10}$ alkyl. In some embodiments, each $R^L$ independently is n-$C_{10}$ alkyl.

In some embodiments, each $R^2$ independently is hydrogen or methyl; each q independently is 3 to 5; each R' independently is hydrogen or methyl; and each $R^L$ independently is $C_{8-12}$ alkyl.

In some embodiments, each $R^2$ is hydrogen; each q independently is 3 to 5; each R' is hydrogen; and each $R^L$ independently is $C_{8-12}$ alkyl.

In some embodiments, each $R^2$ is hydrogen; each q is 4; each R' is hydrogen; and each $R^L$ independently is $C_{8-12}$ alkyl.

In some embodiments, a cationic lipid comprises a compound of formula I-g:

I-g

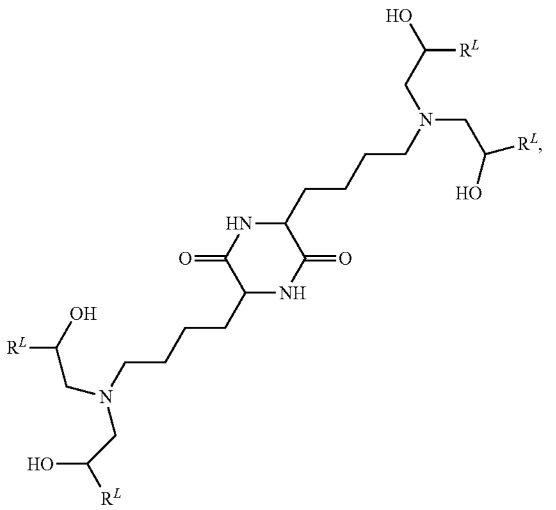

or a pharmaceutically acceptable salt thereof, wherein each $R^L$ independently is $C_{8-12}$ alkyl. In some embodiments, each $R^L$ independently is n-$C_{8-12}$ alkyl. In some embodiments, each $R^L$ independently is $C_{9-11}$ alkyl. In some embodiments, each $R^L$ independently is n-$C_{9-11}$ alkyl. In some embodiments, each $R^L$ independently is $C_{10}$ alkyl. In some embodiments, each $R^L$ is n-$C_{10}$ alkyl.

In particular embodiments, a suitable cationic lipid is cKK-E12, or (3,6-bis(4-(bis(2-hydroxydodecyl)amino)butyl)piperazine-2,5-dione), and pharmaceutically acceptable salts thereof. Structure of cKK-E12 is shown below:

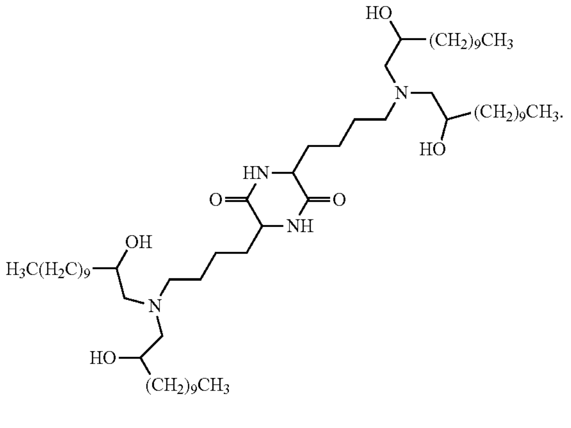

Additional exemplary cationic lipids include those of formula I:

I

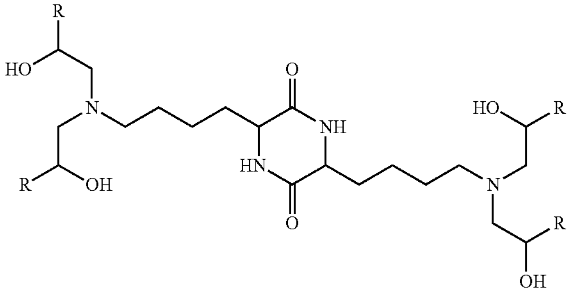

and pharmaceutically acceptable salts thereof, wherein, ("OF-00")

R is 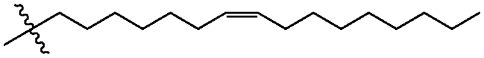 , ("OF-01")

R is 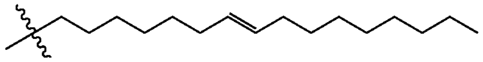 , ("OF-02")

R is 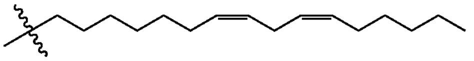 , or ("OF-03")

R is 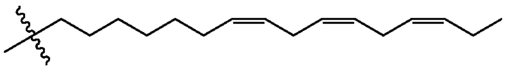

(see, e.g., Fenton, Owen S., et al. "Bioinspired Alkenyl Amino Alcohol Ionizable Lipid Materials for Highly Potent In Vivo mRNA Delivery." *Advanced materials* (2016)).

In some embodiments, one or more cationic lipids suitable for the present invention may be N-[1-(2,3-dioleyloxy)propyl]-N,N,N-trimethylammonium chloride or "DOTMA". (Feigner et al. (Proc. Nat'l Acad. Sci. 84, 7413 (1987); U.S. Pat. No. 4,897,355, which are incorporated herein by reference). Other suitable cationic lipids include, for example, 5-carboxyspermylglycinedioctadecylamide or "DOGS," 2,3-dioleyloxy-N-[2(spermine-carboxamido)ethyl]-N,N-dimethyl-1-propanaminium or "DOSPA" (Behr et al. Proc. Nat.'l Acad. Sci. 86, 6982 (1989); U.S. Pat. Nos. 5,171,678; 5,334,761), 1,2-Dioleoyl-3-Dimethylammonium-Propane or "DODAP", 1,2-Dioleoyl-3-Trimethylammonium-Propane or "DOTAP".

Additional exemplary cationic lipids also include 1,2-distearyloxy-N,N-dimethyl-3-aminopropane or "DSDMA", 1,2-dioleyloxy-N,N-dimethyl-3-aminopropane or "DODMA", 1,2-dilinoleyloxy-N,N-dimethyl-3-aminopropane or "DLinDMA", 1,2-dilinolenyloxy-N,N-dimethyl-3-aminopropane or "DLenDMA", N-dioleyl-N,N-dimethylammonium chloride or "DODAC", N,N-distearyl-N,N-dimethylammonium bromide or "DDAB", N-(1,2-dimyristyloxyprop-3-yl)-N,N-dimethyl-N-hydroxyethyl ammonium bromide or "DMRIE", 3-dimethylamino-2-(cholest-5-en-3-beta-oxybutan-4-oxy)-1-(cis,cis-9,12-octadecadienoxy)propane or "CLinDMA", 2-[5'-(cholest-5-en-3-beta-oxy)-3'-oxapentoxy)-3-dimethyl-1-(cis,cis-9', 1-2'-octadecadienoxy)propane or "CpLinDMA", N,N-dimethyl-3,4-dioleyloxybenzylamine or "DMOBA", 1,2-N,N'-dioleylcarbamyl-3-dimethylaminopropane or "DOcarbDAP", 2,3-Dilinoleoyloxy-N,N-dimethylpropylamine or "DLinDAP", 1,2-N,N'-Dilinoleylcarbamyl-3-dimethylaminopropane or "DLincarbDAP", 1,2-Dilinoleoylcarbamyl-3-dimethylaminopropane or "DLinCDAP", 2,2-dilinoleyl-4-dimethylaminomethyl-[1,3]-dioxolane or ("DLin-K-DMA"), 2-((8-[(3P)-cholest-5-en-3-yloxy]octyl)oxy)-N, N-dimethyl-3-[(9Z, 12Z)-octadeca-9, 12-dien-1-yloxy]propane-1-amine ("Octyl-CLinDMA"), (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"), (2S)-2-((8-[(3P)-cholest-5-en-3-yloxy]octyl)oxy)-N, fsl-dimethyh3-[(9Z, 12Z)-octadeca-9, 12-dien-1-yloxy]propan-1-amine ("Octyl-CLinDMA (2S)"); 2,2-dilinoleyl-4-dimethylaminoethyl-[1,3]-dioxolane or "DLin-K-XTC2-DMA", and 2-(2,2-di((9Z,12Z)-octadeca-9,12-dien-1-yl)-1,3-dioxolan-4-yl)-N,N-dimethylethanamine (DLin-KC2-DMA)) (see, WO 2010/042877, which is incorporated herein by reference; Semple et al., Nature Biotech. 28: 172-176 (2010)), or mixtures thereof. (Heyes, J., et al., J Controlled Release 107: 276-287 (2005); Morrissey, D V., et al., Nat. Biotechnol. 23(8): 1003-1007 (2005); International Patent Publication WO2005/121348). In some embodiments, one or more of the cationic lipids comprise at least one of an imidazole, dialkylamino, or guanidinium moiety.

In some embodiments, one or more cationic lipids may be chosen from XTC (2,2-Dilinoleyl-4-dimethylaminoethyl-[1,3]-dioxolane), MC3 (((6Z,9Z,28Z,31Z)-heptatriaconta-6,9,28,31-tetraen-19-yl 4-(dimethylamino)butanoate), ALNY-100 ((3aR,5s,6aS)—N,N-dimethyl-2,2-di((9Z,12Z)-octadeca-9,12-dienyl)tetrahydro-3aH-cyclopenta[d][1,3]dioxol-5-amine)), NC98-5 (4,7,13-tris(3-oxo-3-(undecylamino)propyl)-N1,N16-diundecyl-4,7,10,13-tetraazahexadecane-1,16-diamide), DODAP (1,2-dioleyl-3-dimethylammonium propane), HGT4003 (WO2012/170889, the teachings of which are incorporated herein by reference in their entirety), ICE (WO2011/068810, the teachings of which are incorporated herein by reference in their entirety), HGT5000 (U.S. Provisional Patent Application No. 61/617,468 and International Patent Application WO2013/149140, the teachings of which are incorporated herein by reference in their entirety) or HGT5001 (cis or trans) (Provisional Patent Application No. 61/617,468 and International Patent Application WO2013/149140), aminoalcohol lipidoids such as those disclosed in WO2010/053572, DOTAP (1,2-dioleyl-3-trimethylammonium propane), DOTMA (1,2-di-O-octadecenyl-3-trimethylammonium propane), DLinDMA (Heyes, J.; Palmer, L.; Bremner, K.; MacLachlan, I. "Cationic lipid saturation influences intracellular delivery of encapsulated nucleic acids" J. Contr. Rel. 2005, 107, 276-287), DLin-KC2-DMA (Semple, S. C. et al. "Rational Design of Cationic Lipids for siRNA Delivery" Nature Biotech. 2010, 28, 172-176), C12-200 (Love, K. T. et al. "Lipid-like materials for low-dose in vivo gene silencing" PNAS 2010, 107, 1864-1869), N1GL, N2GL, V1GL and combinations thereof.

In some embodiments, the one or more cationic lipids are amino lipids. Amino lipids suitable for use in the invention include those described in WO2017180917, which is hereby incorporated by reference. Exemplary amino lipids in WO2017180917 include those described at paragraph [0744] such as DLin-MC3-DMA (MC3), (13Z,16Z)—N,N-dimethyl-3-nonyldocosa-13,16-dien-1-amine (L608), and Compound 18. Other amino lipids include Compound 2, Compound 23, Compound 27, Compound 10, and Compound 20. Further amino lipids suitable for use in the invention include those described in WO2017112865, which is hereby incorporated by reference. Exemplary amino lipids in WO2017112865 include a compound according to one of formulae (I), (Ia1)-(Ia6), (Ib), (II), (IIa), (III), (IIia), (IV), (17-1), (19-1), (19-11), and (20-1), and compounds of paragraphs [00185], [00201], [0276]. In some embodiments, cationic lipids suitable for use in the invention include those described in WO2016118725, which is hereby incorporated by reference. Exemplary cationic lipids in WO2016118725 include those such as KL22 and KL25. In some embodiments, cationic lipids suitable for use in the invention include those described in WO2016118724, which is hereby incorporated by reference. Exemplary cationic lipids in WO2016118725 include those such as KL10, 1,2-dilinoleyloxy-N,N-dimethylaminopropane (DLin-DMA), and KL25.

In some embodiments, cationic lipids constitute at least about 5%, 10%, 20%, 30%, 35%, 40%, 45%, 50%, 55%, 60%, 65%, or 70% of the total lipids in a suitable lipid solution by weight or by molar. In some embodiments, cationic lipid(s) constitute(s) about 30-70% (e.g., about 30-65%, about 30-60%, about 30-55%, about 30-50%, about 30-45%, about 30-40%, about 35-50%, about 35-45%, or about 35-40%) of the total lipid mixture by weight or by molar.

Non-Cationic/Helper Lipids

As used herein, the phrase "non-cationic lipid" refers to any neutral, zwitterionic or anionic lipid at a selected pH, such as physiological pH, or under selected conditions, such as conditions under which the composition is formulated and/or administered. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 1,2-dierucoyl-sn-glycero-3-phosphoethanolamine (DEPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a mixture thereof. In some embodiments, a suitable lipid solution includes DOPE as the non-cationic lipid component. In other embodiments, a suitable lipid solution includes DEPE as the non-cationic lipid component.

In some embodiments, non-cationic lipids may constitute at least about 5%, 10%, 15%, 20%, 25%, 30%, 35%, 40%, 45%, 50%, 55%, 60%, 65% or 70% of the total lipids in a suitable lipid solution by weight or by molar. In some embodiments, total non-cationic lipid(s) constitute(s) about 30-50% (e.g., about 30-45%, about 30-40%, about 35-50%, about 35-45%, or about 35-40%) of the total lipids in a suitable lipid solution by weight or by molar.

Cholesterol-Based Lipids

A suitable lipid solution typically includes at least one cholesterol-based lipid. For example, suitable cholesterol-based cationic lipids include, for example, DC-Choi (N,N-dimethyl-N-ethylcarboxamidocholesterol), 1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or imidazole cholesterol ester (ICE) as disclosed in International Patent Publication WO 2011/068810, which has the following structure,

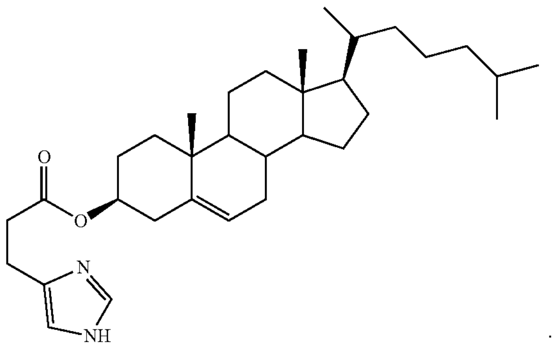

("ICE")

In embodiments, a cholesterol-based lipid is cholesterol. In other embodiments, a cholesterol-based lipid is ICE. In a particular embodiment, ICE is both the cholesterol-based lipid component and the cationic lipid component of a lipid nanoparticle disclosed herein.

In some embodiments, cholesterol-based lipid(s) constitute (s) at least about 5%, 10%, 20%, 30%, 40%, 50%, 60%, or 70% of the total lipids in a suitable lipid solution by weight or by molar. In some embodiments, cholesterol-based lipid (s) constitute(s) about 30-50% (e.g., about 30-45%, about 30-40%, about 35-50%, about 35-45%, or about 35-40%) of the total lipids in a suitable lipid solution by weight or by molar.

PEG-Modified Lipids

The presence of PEG-modified lipids in a lipid nanoparticle may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613).

For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention. Contemplated PEG-modified lipids include, but are not limited to, a polyethylene glycol chain of up to 2 kDa, up to 3 kDa, up to 4 kDa or up to 5 kDa in length covalently attached to a lipid with alkyl chain(s) of $C_6$-$C_{20}$ length. In some embodiments, a PEG-modified or PEG-modified lipid is PEG-modified cholesterol or PEG-2K. In some embodiments, particularly useful exchangeable lipids are PEG-ceramides having shorter acyl chains (e.g., $C_{14}$ or $C_{18}$).

PEG-modified phospholipid and derivatized lipids may constitute at least about 5%, 10%, 20%, 30%, 40%, 50%, 60%, or 70% of the total lipids in a suitable lipid solution by weight or by molar. In some embodiments, PEG-modified lipid lipid(s) constitute(s) about 30-50% (e.g., about 30-45%, about 30-40%, about 35-50%, about 35-45%, or about 35-40%) of the total lipids in a suitable lipid solution by weight or by molar.

Lipid solutions suitable for use with the invention typically include a PEG-modified lipid such as 1,2-dimyristoyl-rac-glycero-3-methoxypolyethylene glycol-2000 (DMG-PEG2K).

Exemplary Lipid Formulations

Various combinations of lipids, i.e., cationic lipids, non-cationic lipids, PEG-modified lipids and optionally cholesterol, that can used to prepare, and that are comprised in, preformed lipid nanoparticles are described in the literature and herein. A preferred lipid solution comprises cDD-TE-4-E12, DOPE, and DMG-PEG2K. Another preferred lipid solution comprises cDD-TE-4-E12, DOPE, cholesterol and DMG-PEG2K. Another preferred lipid solution comprises cDD-TE-4-E12, DEPE, and DMG-PEG2K. Another preferred lipid solution comprises cDD-TE-4-E12, DEPE, cholesterol and DMG-PEG2K. Another preferred lipid solution comprises cDD-TE-4-E10, DOPE, and DMG-PEG2K. Another preferred lipid solution comprises cDD-TE-4-E10, DOPE, cholesterol and DMG-PEG2K. Another preferred lipid solution comprises cDD-TE-4-E10, DEPE, and DMG-PEG2K. Another preferred lipid solution comprises cDD-TE-4-E10, DEPE, cholesterol and DMG-PEG2K.

However, other lipid formulations are contemplated, for example, a suitable lipid solution may contain cKK-E12, DOPE, cholesterol, and DMG-PEG2K; C12-200, DOPE, cholesterol, and DMG-PEG2K; HGT5000, DOPE, cholesterol, and DMG-PEG2K; HGT5001, DOPE, cholesterol, and DMG-PEG2K; cKK-E12, DPPC, cholesterol, and DMG-PEG2K; C12-200, DPPC, cholesterol, and DMG-PEG2K; HGT5000, DPPC, cholesterol, and DMG-PEG2K; HGT5001, DPPC, cholesterol, and DMG-PEG2K; or ICE, DOPE and DMG-PEG2K. Additional combinations of lipids are described in the art, e.g., U.S. Ser. No. 62/420,421 (filed on Nov. 10, 2016, and corresponding International Patent Application WO2018/089790), U.S. Ser. No. 62/421,021 (filed on Nov. 11, 2016, and corresponding International Patent Application WO2018/089790), U.S. Ser. No. 62/464,327 (filed on Feb. 27, 2017, and corresponding International Patent Application WO2018/089790), and PCT Application entitled "Novel ICE-based Lipid Nanoparticle Formulation for Delivery of mRNA," filed on Nov. 10, 2017, the disclosures of which are included here in their full scope by reference.

The selection of cationic lipids, non-cationic lipids and PEG-modified lipids which comprise the lipid mixture as well as the relative molar ratio of such lipids to each other, is based upon the characteristics of the selected lipid(s) and the nature and characteristics of the mRNA to be encapsulated. Additional considerations include, for example, the saturation of the alkyl chain, as well as the size, charge, pH, pKa, fusogenicity and toxicity of the selected lipid(s). Thus the molar ratios may be adjusted accordingly.

mRNA Encapsulation

As used herein, "Process A" refers to a conventional method of encapsulating mRNA by mixing an mRNA solution and lipid solution, wherein the mRNA solution and/or the lipid solution are heated to greater than ambient temperature prior to mixing, without first pre-forming the lipids into lipid nanoparticles (as described in U.S. patent application Ser. No. 14/790,562 entitled "Encapsulation of messenger RNA", filed Jul. 2, 2015 and its provisional U.S. patent application Ser. No. 62/020,163, filed Jul. 2, 2014, and in International Patent Application WO2016/004318, and in US 2016/0038432).

As used herein, "Remix Process" (or "Process B") refers to another conventional method of encapsulating mRNA by mixing a suspension comprising preformed lipid nanoparticles with an mRNA solution, as described in US 2018/0153822.

The present invention relates to a novel method of formulating mRNA-containing lipid nanoparticles. As in the "Remix Process", this process involves combining preformed empty lipid nanoparticles with mRNA. The inventors surprisingly found that changing the N/P ratio during combination of empty preformed lipid nanoparticles and mRNA improves potency and efficacy of the resulting lipid nanoparticles encapsulating the mRNA.

Empty lipid nanoparticles are formed by mixing a lipid solution containing dissolved lipids with an aqueous or buffer solution. The resulting suspension of preformed empty lipid nanoparticles is then added to an mRNA solution to encapsulate the mRNA. In some embodiments, empty lipid nanoparticles are formed by mixing a lipid solution containing lipids dissolved in a solvent with an aqueous solution. In some embodiments, the solvent can be ethanol. In some embodiments, the aqueous solution can be a citrate buffer.

In some embodiments, ethanol, citrate buffer, and other destabilizing agents are absent during the addition of mRNA and hence the formulation does not require any further downstream processing. In particular embodiments, after formation of empty preformed lipid nanoparticles, the buffer is exchanged for a suitable storage buffer. In some embodiments, the storage buffer comprises or consists of an aqueous solution comprising about 5%, about 10%, about 15%, about 20%, about 25%, about 30%, about 35%, about 40%, about 45%, or about 50% disaccharide (w/v). Suitable disaccharides include sucrose and trehalose. In some embodiments, addition of mRNA to empty lipid nanoparticles in the storage buffer can result in a final formulation that does not require any downstream purification or processing and can be stably stored in frozen form. In a typical embodiment, the storage buffer comprises or consists of an aqueous solution comprising about 10% trehalose.

Heating During Encapsulation

As used herein, the term "ambient temperature" refers to the temperature in a room, or the temperature which surrounds an object of interest (e.g., a preformed empty lipid nanoparticle suspension, an mRNA solution, or a lipid nanoparticle suspension containing mRNA) without heating or cooling.

In some embodiments, the solution comprising the mRNA is at ambient temperature prior to any mixing step. In some embodiments, the ambient temperature is or is less than about 35° C., 30° C., 25° C., 20° C., or 16° C. In some embodiments, the ambient temperature ranges from about 15-35° C., about 15-30° C., about 15-25° C., about 15-20° C., about 20-35° C., about 25-35° C., about 30-35° C., about 20-30° C., about 25-30° C. or about 20-25° C. In some embodiments, the ambient temperature is 20-25° C. In some embodiments, ambient temperature ranges from about 19° C. to 23° C., e.g., between 20° C. and 22° C., e.g. about 21° C.

In particular embodiments, the suspension comprising the empty LNPs is at a temperature greater than ambient temperature prior to being combined with the mRNA solution. In some embodiments, the combined mixture of the mRNA solution and the suspension comprising the empty LNPs is heated to a temperature greater than ambient temperature. A temperature greater than ambient temperature is typically greater than about 25° C. In some embodiments, a temperature greater than ambient temperature is greater than about 30° C., 35° C., 40° C., 45° C., 50° C., 55° C., 60° C., 65°

C., or 70° C. In some embodiments, a temperature greater than ambient temperature ranges from about 25-70° C., about 30-70° C., about 35-70° C., about 40-70° C., about 45-70° C., about 50-70° C., or about 60-70° C. In particular embodiments, a temperature greater than ambient temperature is about 60-70° C. In particular embodiments, a temperature greater than ambient temperature is about 65° C.

In a typical embodiment, the total heating time is limited to 20 min or less (e.g. 16 min, 15 min, 14 min, or less). In some embodiments, the total heating time is between 10 min and 20 min, e.g. about 15 min.

In some embodiments, no heating of one or more of the suspension comprising the preformed lipid nanoparticles, the solution comprising the mRNA and the combination of the suspension and solution occurs before or after the formulation process.

Addition of Volumes and Mixing

In one aspect, the invention relates to a process of encapsulating mRNA in preformed empty lipid nanoparticles (LNPs). Such a process involves combining a solution comprising the mRNA with a suspension comprising the preformed empty LNPs such that a mixture comprising LNPs encapsulating the mRNA (also referred to herein as a "mixed fluid") are formed. In subsequent steps, one or more additional volumes of the solution comprising the mRNA or of the preformed empty LNPs are added to the mixture obtained in the preceding step until a desired molar ratio of cationic lipid to mRNA is achieved. In some embodiments, the subsequent steps of adding one or more additional volumes of the solution comprising the mRNA or of the preformed empty LNPs comprises or consists of a period of mixing. The one or more additional volumes may either be added continuously or stepwise. In some embodiments, the number of additional volumes is 3, 4, or 5. In particular embodiments, the number of additional volumes is 3.

Periods of mixing may be performed following the addition of any one of, or each of, the one or more additional volumes. The first volume and the one or more additional volumes may have the same, a greater, or a smaller volume relative to each preceding volume. Typically, the first volume and the one or more additional volumes are the same. Each period of time of mixing may be the same, longer, or shorter relative to each preceding period. Typically, each period of time of mixing is the same.

A period of mixing may not exceed 5 minutes. For example, a period of between 1 min and 5 minutes may be sufficient to achieve high encapsulation efficiencies. In some embodiments, a period of mixing (e.g., 1 min) is followed by an incubation period (e.g., 4 min) in which the mixed fluid is stored, e.g., in an intermediate storage level. When the suspension of preformed LNPs, the mixed fluid, or both are heated during the encapsulation process, minimizing the periods of mixing and/or subsequent incubation periods and hence heat exposure of the encapsulated mRNA can be beneficial to avoid or reduce mRNA degradation (in particular for large mRNA, e.g., mRNAs of 4 kb and larger, e.g. 5 kb and larger).

In some embodiments, encapsulating mRNA in preformed empty LNPs can be performed by pumping a first fluid comprising mRNA and a second fluid comprising preformed empty LNPs to a mixing junction within which the first and second fluids are mixed. Typically, the mRNA is encapsulated into the LNPs upon mixing in the mixing junction. Incubating the mixed fluid for a period of time after mixing may increase encapsulation efficiency. This can be done in an intermediary storage vessel as described in more detail below.

In some embodiments, an mRNA solution and a suspension of preformed empty LNPs may be mixed using one or more pump(s). As the encapsulation procedure can occur on a wide range of scales, different types of pumps may be used to accommodate the desired scale. It is typically desirable to use a pulse-less flow pumps. As used herein, a pulse-less flow pump refers to any pump that can establish a continuous flow with a stable flow rate. Types of suitable pumps may include, but are not limited to, gear pumps, positive displacement pumps, and centrifugal pumps. Exemplary gear pumps include, but are not limited to, Cole-Parmer or Diener gear pumps. Exemplary centrifugal pumps include, but are not limited to, those manufactured by Grainger or Cole-Parmer.

Table 1 (below) illustrates a method for encapsulating mRNA in preformed empty LNPs according to an embodiment of the invention. The flow rate X may be measured (or expressed) in mL/min. In a first step, a first fluid comprising preformed empty LNPs may be pumped to a mixing junction at a flow rate of 4× and a portion of second fluid comprising mRNA may be pumped to the mixing junction at a flow rate of X. In a second step, the mixed fluid produced in step 1 may be pumped to the mixing junction at a flow rate of 5× and a further portion of second fluid comprising mRNA may be pumped to the mixing junction at a flow rate of X. In a third step, the mixed fluid produced in step 2 may be pumped to the mixing junction at a flow rate of 6× and a further portion of second fluid comprising mRNA may be pumped to the mixing junction at a flow rate of X. In a fourth step, the mixed fluid produced in step 3 may be pumped to the mixing junction at a flow rate of 7× and a further portion of second fluid comprising mRNA may be pumped to the mixing junction at a flow rate of X. In some embodiments, each portion of the second fluid is about the same volume.

The N/P ratio, or molar ratio of cationic lipid in a LNP relative to mRNA encapsulated within that LNP, after each step is shown in the rightmost column of Table 1. In some embodiments, Y may be a molar ratio of about 4 (cationic lipid):1 (mRNA). As can be seen in Table 1, the N/P ratio of the resultant fluid is reduced after each step, thus the method is referred to herein as "Step Down" process, or "Step Down Remix" process.

TABLE 1

Exemplary Flow Rates for a Step Down Remix Process
Step Down Remix Process

| Step | Flow rate of Empty LNPs (N) | Flow rate of mRNA (P) | Flow rate of result of any previous step | Resultant 'N/P' |
|---|---|---|---|---|
| 1 | 4X | X | — | 4Y |
| 2 | 0 | X | 5X | 2Y |
| 3 | 0 | X | 6X | 1.33Y |
| 4 | 0 | X | 7X | Y |

Table 2 (below) illustrates a method for encapsulating mRNA in preformed empty LNPs according to an embodiment of the invention. X may be measured (or expressed) in mL/min. In a first step, a portion of first fluid comprising preformed empty LNPs may be pumped to a mixing junction at a flow rate of X and a second fluid comprising mRNA may be pumped to the mixing junction at a flow rate of 4×. In a second step, the mixed fluid produced in step 1 may be pumped to the mixing junction at a flow rate of 5× and a further portion of first fluid comprising preformed empty LNPs may be pumped to the mixing junction at a flow rate of X. In a third step, the mixed fluid produced in step 2 may be pumped to the mixing junction at a flow rate of 6× and a further portion of first fluid comprising preformed empty LNPs may be pumped to the mixing junction at a flow rate of X. In a fourth step, the mixed fluid produced in step 3 may be pumped to the mixing junction at a flow rate of 7× and a further portion of first fluid comprising preformed empty LNPs may be pumped to the mixing junction at a flow rate of X. In some embodiments, each portion of the first fluid is about the same volume.

The N/P ratio, or molar ratio of cationic lipid in a LNP relative to mRNA encapsulated within that LNP, after each step is shown in the rightmost column of Table 2. In some embodiments, Y may be a molar ratio of about 4 (cationic lipid):1 (mRNA). As can be seen in Table 2, the N/P ratio of the resultant fluid is increased after each step, thus the method is referred to herein as a "Step Up" process, or "Step Up Remix" process.

TABLE 2

Exemplary Flow Rates for a Step Up Remix Process
Step up Remix Process

| Step | Flow rate of Empty LNPs (N) | Flow rate of mRNA (P) | Flow rate of result of any previous step | Resultant 'N/P' |
|---|---|---|---|---|
| 1 | X | 4X | — | Y/4 |
| 2 | X | 0 | 5X | Y/2 |
| 3 | X | 0 | 6X | 3Y/4 |
| 4 | X | 0 | 7X | Y |

The mRNA solution may be pumped at a flow rate of between 20 mL/min and 20 L/min. The preformed empty LNP suspension may be pumped at a flow rate of between 20 mL/min and 20 L/min. In a commercial scale embodiment of the invention, the mRNA solution and preformed empty LNP suspension may be pumped at flow rates of between 1 L/min and 20 L/min, e.g. between 5 L/min and 15 L/min, e.g., 10 L/min. In a laboratory scale embodiment of the invention, the mRNA solution and preformed empty LNP suspension may be pumped at flow rates of between 20 mL/min and 1 L/min, e.g., between 50 mL/min and 500 mL/min, e.g. 250 mL/min.

In some embodiments, the periods of mixing may last for between 1 minute and 5 minutes. In some embodiments, there are between 2 and 4 periods of mixing. There may, therefore, be a total time of pumping the mRNA solution and/or preformed empty LNP suspension of between 2 minutes and 20 minutes. Accordingly, in some embodiments, there may be an initial total volume of mRNA solution of between 40 mL and 100 L, and an initial total volume of preformed empty LNP suspension of between 40 mL and 100 L. The total volume of mixed fluid may be between 80 mL and 200 L.

In a commercial scale embodiment of the invention, the initial total volume of mRNA solution may be between 5 L and 100 L, and the initial total volume of preformed empty LNP suspension may be between 5 L and 100 L, and the total volume of mixed fluid may be between 10 L and 200 L. In a laboratory scale embodiment of the invention, the initial total volume of mRNA solution may be between 100 mL and 5 L, and the initial total volume of preformed empty LNP suspension may be between 100 mL and 5 L, and the total volume of mixed fluid may be between 200 mL and 10 L.

Apparatuses Used for Encapsulation

Apparatuses which are configured to perform the methods described herein are described below. In some embodiments, the apparatuses are configurable to perform either a Step Down Remix method or a Step Up Remix method, in that components of the apparatus can at one time be configured to perform a Step Up Remix method and not a Step Down Remix method and at another time be configured to perform a Step Down Remix method and not a Step Up Remix method. In some embodiments, the apparatuses are configured to perform, selectively, either a Step Up Remix or a Step Down Remix method. In some embodiments, the apparatuses are configured to perform either a Step Up Remix or a Step Down Remix method.

Apparatuses as described herein are exemplary and as such are not limiting on the scope of the claims. It will be apparent to a person skilled in the art that certain modifications, replacements, and additions can be made to the apparatuses described herein without departing from the scope and spirit of the invention.

Figure 11:
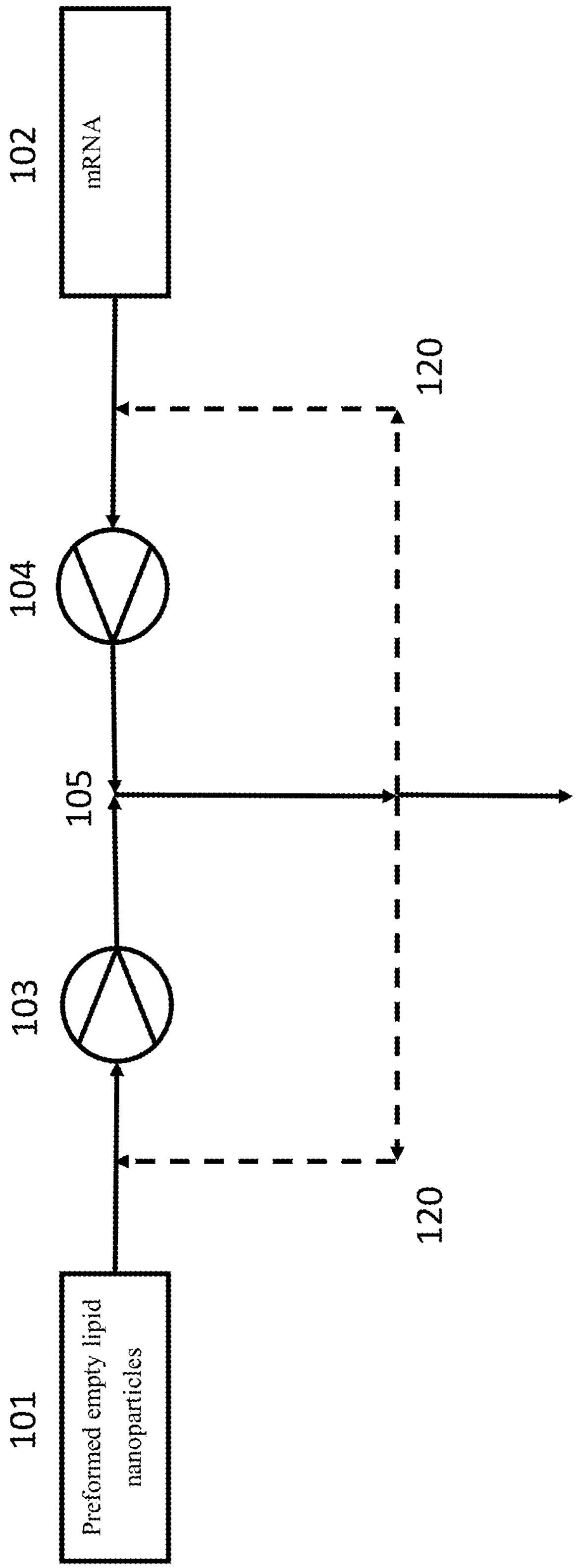
FIG. 11 illustrates an apparatus for encapsulating messenger mRNA into preformed empty LNPs by mixing a first fluid comprising preformed empty LNPs and a second fluid comprising mRNA for use with the methods described herein.

FIG. 11 shows an apparatus configured for use with mRNA encapsulation processes described here. A first fluid comprising mRNA may be stored in a first storage vessel 101 and a second fluid comprising preformed empty LNPs may be stored in a second storage vessel 102. The first fluid may be pumped to a mixing junction 105 by a first pump 103 and the second fluid may be pumped to the mixing junction 105 by a second pump 104. The conduits through which the first fluid is transported from the first storage vessel 101 to the mixing junction 105 may be referred to as an arrangement of LNP conduits, and the conduits through which the second fluid is transported from the second storage vessel 102 to the mixing junction 105 may be referred to as an arrangement of mRNA conduits. During operation of the apparatus, the mixing junction 105 may produce a mixed fluid when the first and second fluids are pumped into it at the same time. A recycle loop 120 is configurable to direct the mixed fluid to a position in the arrangement of LNP conduits upstream of the first pump 103 or to a position in the arrangement of mRNA conduits upstream of the second pump, when the apparatus is in operation.

Figure 12B:
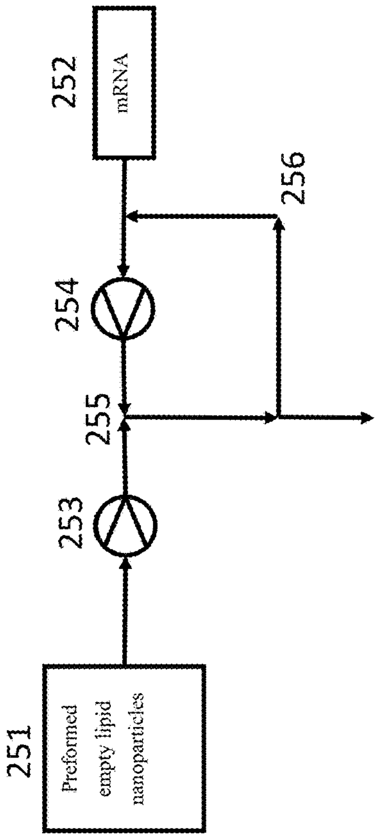
FIG. 12B illustrates a configuration of the apparatus of FIG. 11 in which the recycle loop is configured to direct the mixed fluid upstream of the second pump. When the apparatus is in operation, the recycle loop 260 is configured to direct the mixed fluid from the mixing junction 205 to a position in the arrangement of mRNA conduits upstream of the second pump 204.
Figure 12A:
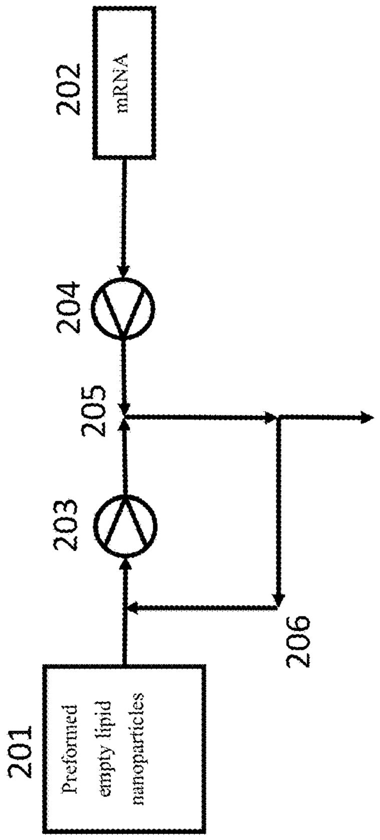
FIG. 12A illustrates a configuration of the apparatus of FIG. 11 in which the recycle loop is configured to direct the mixed fluid upstream of the first pump. When the apparatus is in operation, the recycle loop 260 is configured to direct the mixed fluid from the mixing junction 205 to a position in the arrangement of LNP conduits upstream of the first pump 203.

FIG. 12A shows an apparatus configured for use with mRNA encapsulation processes described here. The apparatus may operate substantially in the same way as the apparatus shown in FIG. 11. When the apparatus is in operation, the recycle loop 260 is configured to direct the mixed fluid from the mixing junction 205 to a position in the arrangement of LNP conduits upstream of the first pump 203. It may be said that the apparatus is operating in a Step Down Remix mode of operation when the recycle loop 260 is configured to direct the mixed fluid from the mixing junction 205 to a position in the arrangement of LNP conduits upstream of the first pump 203. When the apparatus is configured to operate in a Step Down Remix mode of operation, the molar ratio of cationic lipids to mRNA in the mixed fluid reduces every time the mixed fluid passes through the mixing junction 205.

FIG. 12B shows an apparatus configured for use with mRNA encapsulation processes described here. The apparatus may operate substantially in the same way as the apparatus shown in FIG. 11. When the apparatus is in operation, the recycle loop 260 is configured to direct the mixed fluid from the mixing junction 205 to a position in the arrangement of mRNA conduits upstream of the second pump 204. It may be said that the apparatus is operating in a Step Up Remix mode of operation when the recycle loop 260 is configured to direct the mixed fluid from the mixing junction 205 to a position in the arrangement of LNP conduits upstream of the second pump 204. When the apparatus is configured to operate in a Step Up Remix mode of operation, the molar ratio of cationic lipids to mRNA in the mixed fluid increases every time the mixed fluid passes through the mixing junction 205.

Figure 13:
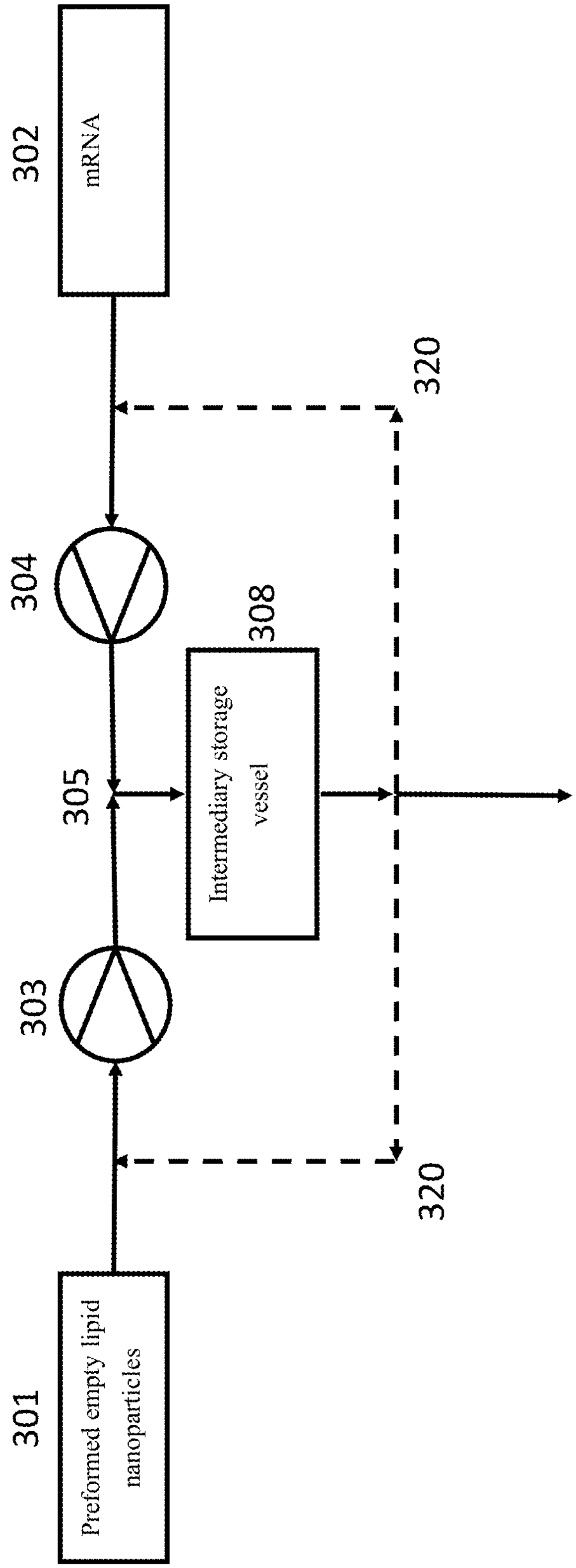
FIG. 13 illustrates an apparatus including an intermediary storage vessel for use with the methods described herein.

FIG. 13 shows an apparatus configured for use with mRNA encapsulation processes described here. The apparatus may operate substantially in the same way as the apparatus shown in FIG. 11, but incorporating an intermediary storage vessel 308. When the apparatus is in operation, the mixed fluid may be directed from the mixing junction 305 to the intermediary storage vessel 308, in which the mixed fluid is stored before being directed to the recycling loop 320. The mixed fluid stored in the intermediary storage vessel 308 may be pumped to the recycle loop by a pump (not shown) or by the first or second pump when the recycle loop 320 is configured in a Step Down Remix or Step Up Remix mode of operation, respectively.

Figure 14:
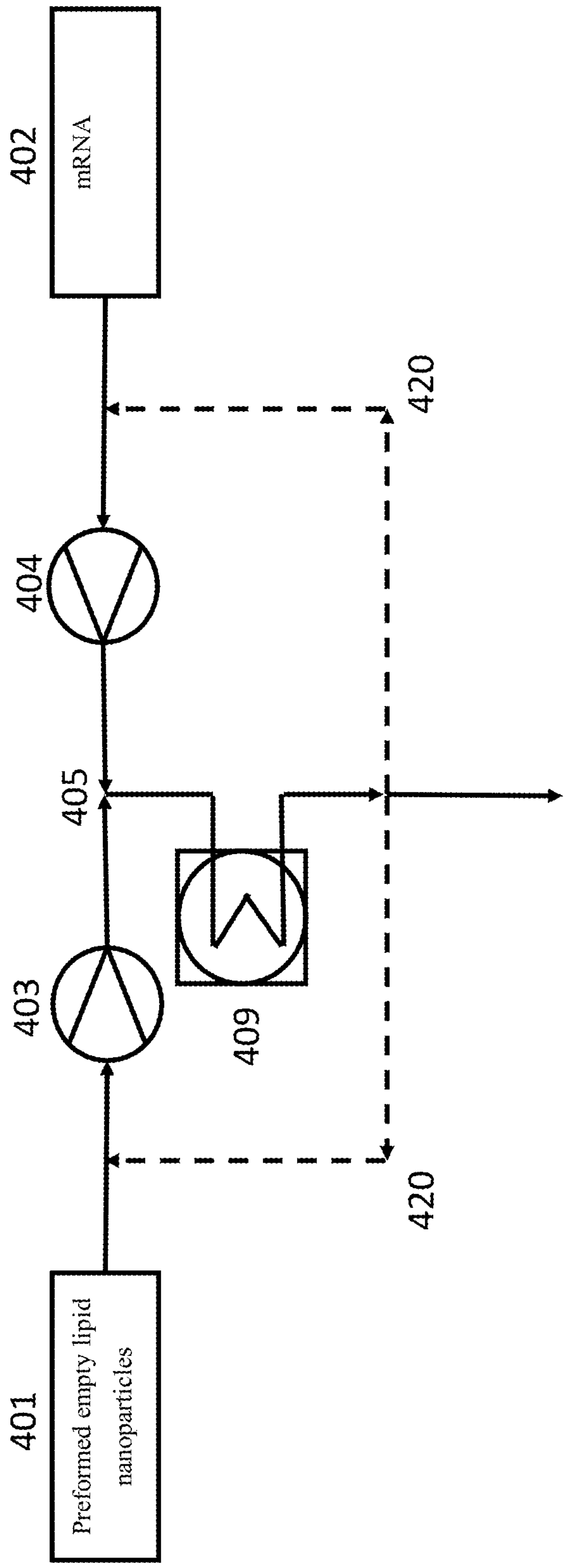
FIG. 14 illustrates an apparatus including a first heat exchanger for use with the methods described herein.

FIG. 14 shows an apparatus configured for use with mRNA encapsulation processes described here. The apparatus may operate substantially in the same way as the apparatus shown in FIG. 11, but incorporating a first heat exchanger 409. When the apparatus is in operation, the mixed fluid may be directed from the mixing junction 405 to the first heat exchanger 409, in which the mixed fluid is heated before being directed to the recycling loop 420. The heat exchanger may be configured to heat the mixed fluid to a desired temperature before the mixed fluid is directed to the recycling loop 420.

Figure 15:
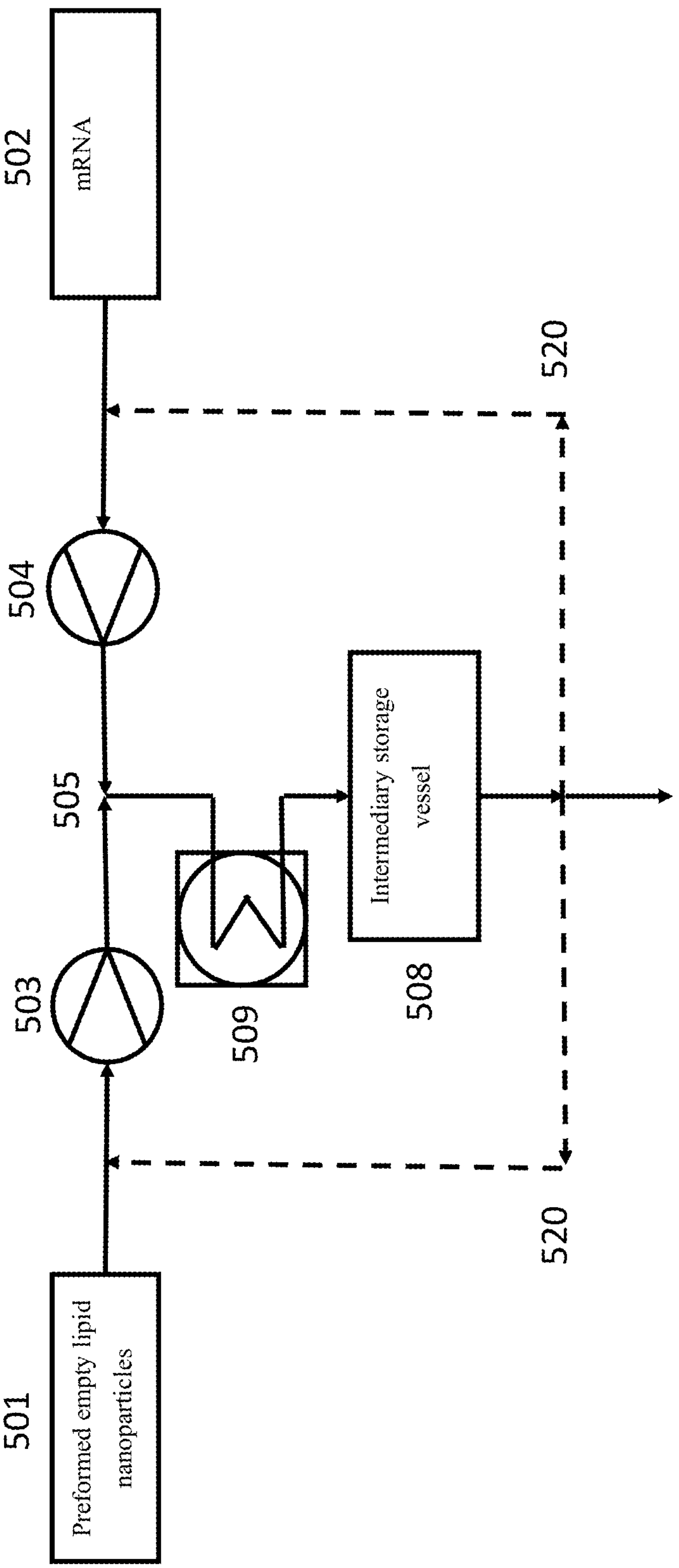
FIG. 15 illustrates an apparatus including an intermediary storage vessel and first heat exchanger for use with the methods described herein.

FIG. 15 shows an apparatus configured for use with mRNA encapsulation processes described here. The apparatus may operate substantially in the same way as the apparatus shown in FIG. 14, but incorporating an intermediary storage vessel 508. When the apparatus is in operation, the mixed fluid may be directed from mixing junction 505 to the first heat exchanger 509, and from the first heat exchanger 509 to the intermediary storage vessel 508. The intermediary storage vessel 508 may operate in substantially the same way as the intermediary storage vessel described in relation to FIG. 13. Optionally, the mixed fluid may be directed from the mixing junction 505 to the intermediary storage vessel 508 before being directed to the first heat exchanger 509.

Figure 16:
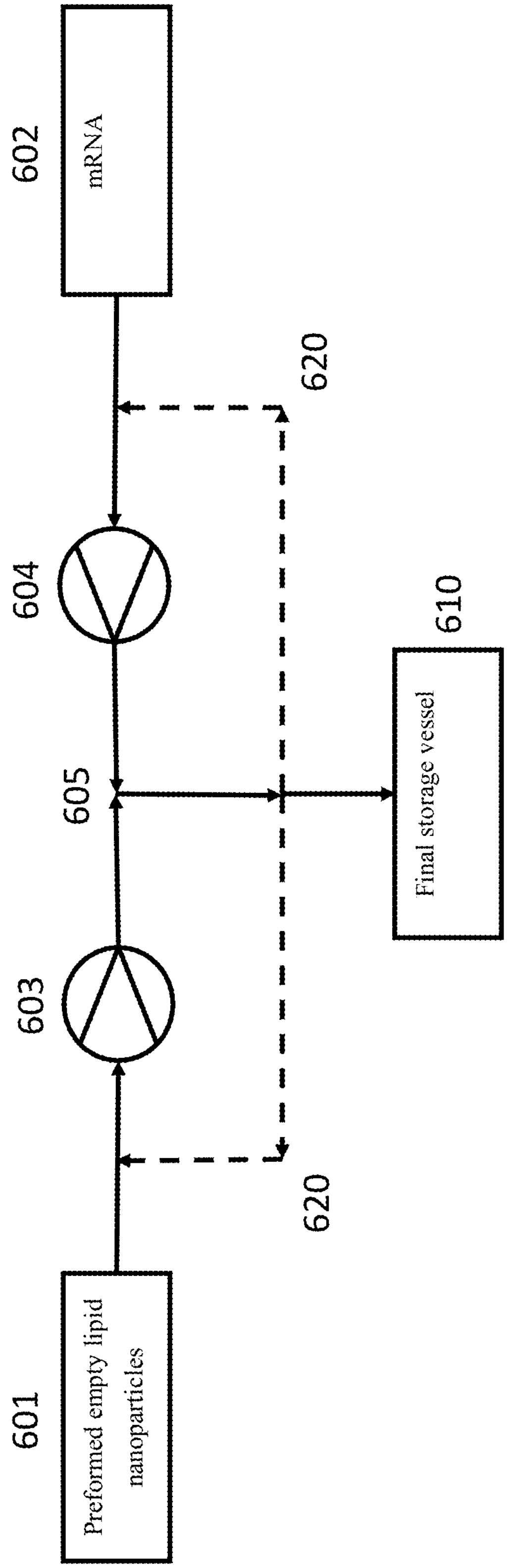
FIG. 16 illustrates an apparatus including a final storage vessel for use with the methods described herein.

FIG. 16 shows an apparatus configured for use with mRNA encapsulation processes described here. The apparatus may operate substantially in the same way as the apparatus shown in FIG. 11, but incorporating a final storage vessel 610. When the apparatus is in operation, the mixed fluid may be directed from the mixing junction 605 to the final storage vessel 610. The apparatus may be configured to direct the mixed fluid from the mixing junction 605 to the final storage vessel 610 after the mixed fluid has passed through the recycle loop 620 a desired number of times. In a particular embodiment, the mixed fluid is directed to the final storage vessel 610 after the mixed fluid has been directed through the recycle loop 620 a total of three times.

Figure 17:
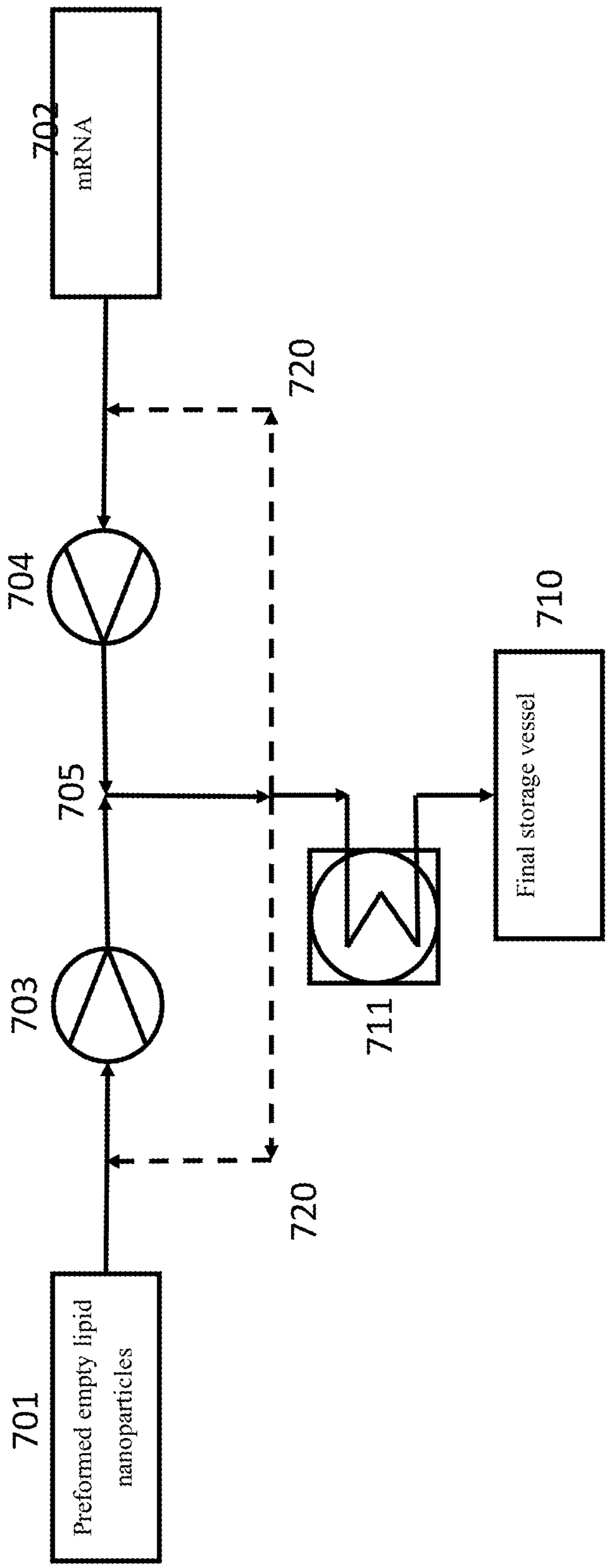
FIG. 17 illustrates an apparatus including a final storage vessel and a second heat exchanger for use with the methods described herein.

FIG. 17 shows an apparatus configured for use with mRNA encapsulation processes described here. The apparatus may operate substantially in the same way as the apparatus shown in FIG. 16, but incorporating a second heat exchanger 711. When the apparatus is in operation, the mixed fluid may be directed from the mixing junction 705 to a second heat exchanger 711, and from the second heat exchanger 711 to a final storage vessel 710. The apparatus may be configured to direct the mixed fluid from the mixing junction 705 to the second heat exchanger 711 after the mixed fluid has passed through the recycle loop 720 a desired number of times. In a particular embodiment, the mixed fluid is directed to the second heat exchanger 711 after the mixed fluid has been directed through the recycle loop 720 a total of three times.

Figure 18:
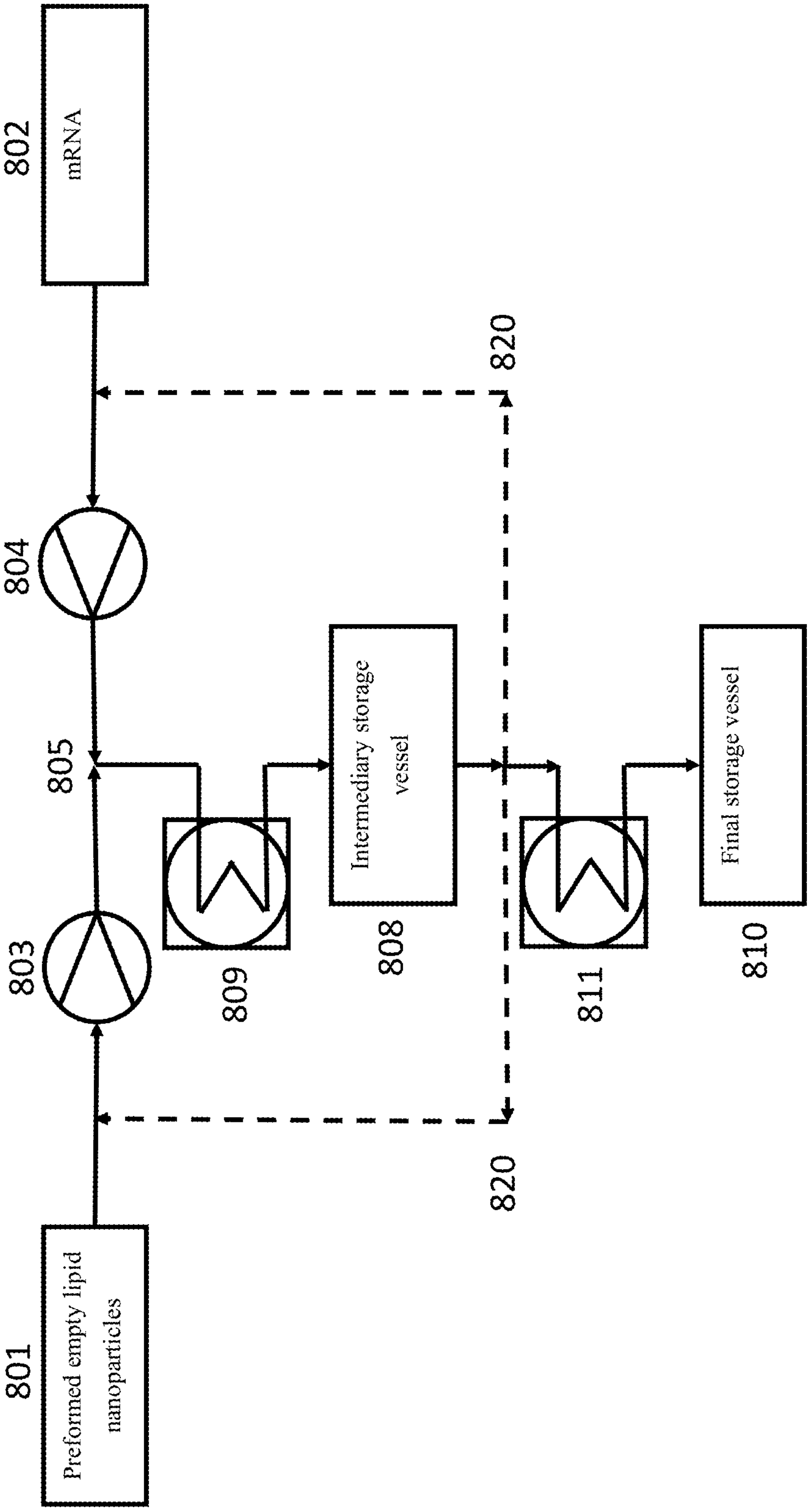
FIG. 18 illustrates an apparatus including an intermediary storage vessel, a final storage vessel, a first heat exchanger, and a second heat exchanger, with the recycle loop configurable to direct the mixed fluid upstream of the first or second pump, for use with the methods described herein.

FIG. 18 shows an apparatus configured for use with mRNA encapsulation processes described here. The apparatus may operate substantially in the same way as the apparatus shown in FIG. 17, but incorporating a first heat exchanger 809 and an intermediary storage vessel 808. When the apparatus is in operation, the mixed fluid may be directed from the mixing junction 805 to the first heat exchanger 809, and directed from the first heat exchanger 809 to the intermediary storage vessel 808. When the apparatus is configured to recycle the mixed fluid, the mixed fluid may be directed from the intermediary storage vessel 808 to the recycle loop 820. When the apparatus is configured to output mixed fluid, the mixed fluid may be directed from the intermediary storage vessel 808 to a second heat exchanger 811, and from the second heat exchanger 811 to a final storage vessel 810. In a particular embodiment, the mixed fluid is directed to the second heat exchanger 811 after the mixed fluid has been directed through the recycle loop 820 a total of three times.

Figure 19:
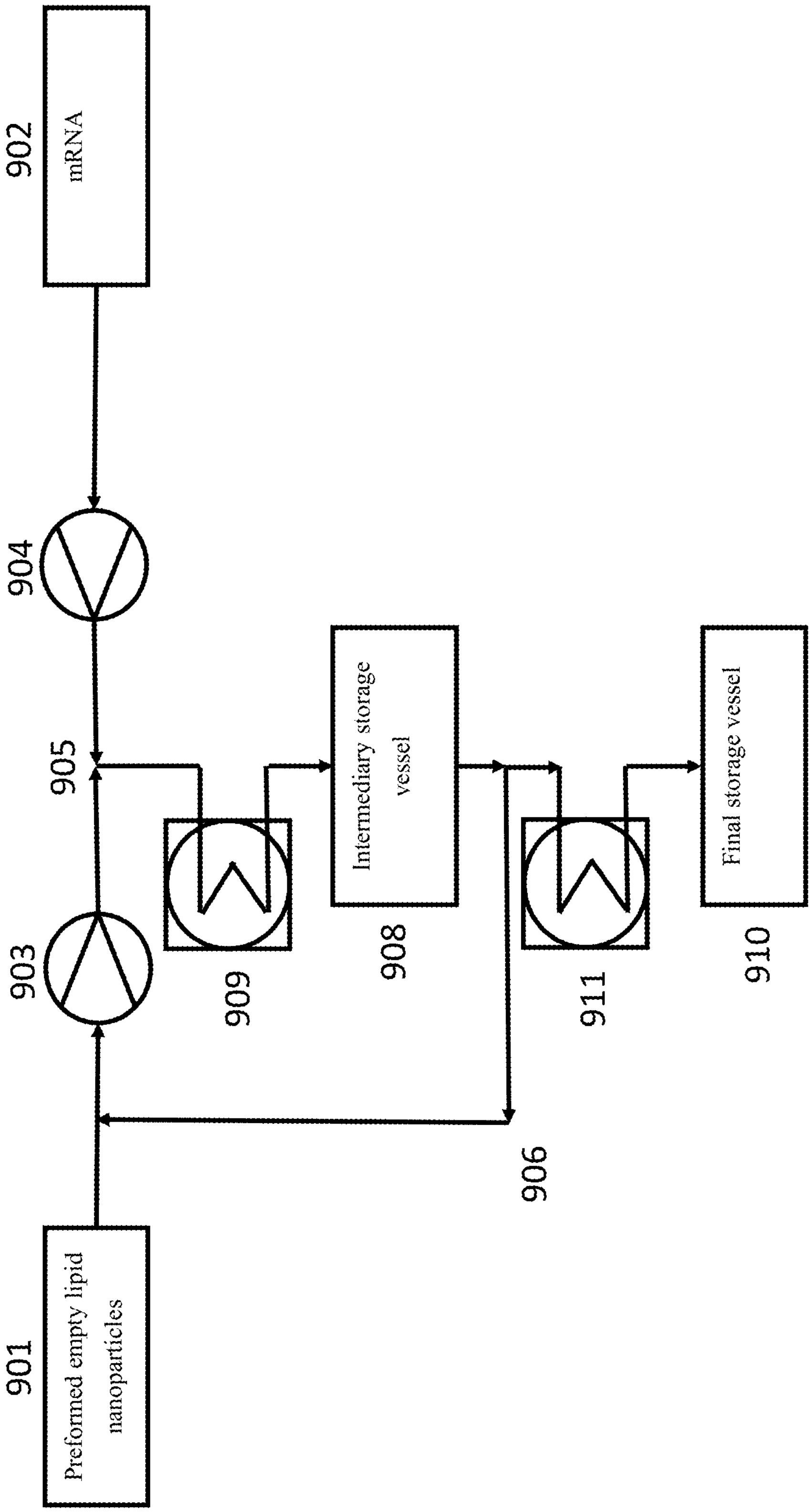
FIG. 19 illustrates the apparatus of claim 17 with the recycle loop configured to direct the mixed fluid upstream of the first pump for use with the methods described herein.

FIG. 19 shows an apparatus configured for use with mRNA encapsulation processes described here. The apparatus may operate substantially in the same way as the apparatus shown in FIG. 18, but with the recycle loop 906 configured to direct the mixed fluid from an intermediary storage vessel 908 to a position in the arrangement of LNP conduits upstream of the first pump 903.

Between cycles of operation or different production runs (e.g., to encapsulate mRNAs encoding different proteins, e.g. for different therapeutic uses), the apparatuses described herein may be cleaned, e.g., by (i) passing a first stream of RNase-free water through the apparatus, (ii) passing a stream of sodium hydroxide solution through the apparatus, and (iii) passing a second stream of RNase-free water through the apparatus. The RNase-free water may be water for injection.

In any one of the apparatuses described herein, optionally, the first heat exchanger may be incorporated into the intermediary storage vessel. Optionally, the second heat exchanger may be incorporated into the final storage vessel.

In any one of the apparatuses described herein, optionally, the first pump may be incorporated into the arrangement of LNP conduits and/or may be incorporated into the first storage vessel. Optionally, the second pump may be incorporated into the arrangement of mRNA conduits and/or may be incorporated into the second storage vessel.

In any one of the apparatuses described herein, optionally, an arrangement of conduits may be one conduit configured to direct fluid between, and through, component parts of the apparatus. Optionally, an arrangement of conduits may comprise a plurality of conduits operatively and/or fluidly coupled to direct fluid between, and through, component parts of the apparatus.

Purification

In some embodiments, the empty preformed lipid nanoparticles or the lipid nanoparticles containing mRNA are purified and/or concentrated. Various purification methods may be used.

In some embodiments, lipid nanoparticles are purified using Tangential Flow Filtration (TFF, also referred to as cross-flow filtration). TFF is a type of filtration wherein the material to be filtered is passed tangentially across a filter rather than through it. In TFF, undesired permeate passes through the filter, while the desired retentate passes along the filter and is collected downstream. It is important to note that the desired material is typically contained in the retentate in TFF, which is the opposite of what one normally encounters in traditional "dead-end" filtration.

Depending upon the material to be filtered, TFF is usually used for either microfiltration or ultrafiltration. Microfiltration is typically defined as instances where the filter has a pore size of between 0.05 μm and 1.0 μm, inclusive, while ultrafiltration typically involves filters with a pore size of less than 0.05 μm. Pore size also determines the nominal molecular weight limits (NMWL), also referred to as the molecular weight cut off (MWCO) for a particular filter, with microfiltration membranes typically having NMWLs of greater than 1,000 kilodaltons (kDa) and ultrafiltration filters having NMWLs of between 1 kDa and 1,000 kDa.

A principal advantage of tangential flow filtration is that non-permeable particles that may aggregate in and block the filter (sometimes referred to as "filter cake") during traditional "dead-end" filtration, are instead carried along the surface of the filter. This advantage allows tangential flow filtration to be widely used in industrial processes requiring continuous operation since down time is significantly reduced because filters do not generally need to be removed and cleaned.

Tangential flow filtration can be used for several purposes including concentration and diafiltration, among others. Concentration is a process whereby solvent is removed from a solution while solute molecules are retained. In order to effectively concentrate a sample, a membrane having a NMWL or MWCO that is substantially lower than the molecular weight of the solute molecules to be retained is used. Generally, one of skill may select a filter having a NMWL or MWCO of three to six times below the molecular weight of the target molecule(s).

Diafiltration is a fractionation process whereby small undesired particles are passed through a filter while larger desired nanoparticles are maintained in the retentate without changing the concentration of those nanoparticles in solution. Diafiltration is often used to remove salts or reaction buffers from a solution. Diafiltration may be either continuous or discontinuous. In continuous diafiltration, a diafiltration solution is added to the sample feed at the same rate that filtrate is generated. In discontinuous diafiltration, the solution is first diluted and then concentrated back to the starting concentration. Discontinuous diafiltration may be repeated until a desired concentration of nanoparticles is reached.

Purified and/or concentrated lipid nanoparticles may be formulated in a desired buffer such as, for example, PBS.

Lipid Nanoparticles Encapsulating mRNA

A process according to the present invention results in higher potency and efficacy, allowing for lower doses and thereby shifting the therapeutic index in a positive direction. In some embodiments, the process according to the present invention results in homogeneous and small particle sizes (e.g., less than 150 nm), as well as significantly improved encapsulation efficiency and/or mRNA recovery rate as compared to a prior art process.

A variety of methods known in the art are available for sizing of a population of lipid nanoparticles. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-450 (1981), incorporated herein by reference. Average liposome diameter may be reduced by sonication of formed liposomes. Intermittent sonication cycles may be alternated with QELS assessment to guide efficient liposome synthesis.

In some embodiments, a majority of purified nanoparticles in a composition, i.e., greater than about 50%, 55%, 60%, 65%, 70%, 75%, 80%, 85%, 90%, 95%, 96%, 97%, 98%, or 99% of the purified nanoparticles, have a size of about 150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm). In some embodiments, substantially all of the purified nanoparticles have a size of about 150 nm (e.g., about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, or about 80 nm). In some embodiments, a lipid nanoparticle has an average size of less than 120 nm. In some embodiments, a lipid nanoparticle has an average size of less than 100 nm. In some embodiments, a lipid nanoparticle has an average size of less than 90 nm. In some embodiments, a lipid nanoparticle has an average size of less than 80 nm. In some embodiments, a lipid nanoparticle has an average size of less than 70 nm. In some embodiments, a lipid nanoparticle has an average size of less than 60 nm. In some embodiments, a lipid nanoparticle has an average size of less than 50 nm. In some embodiments, a lipid nanoparticle has an average size of less than 30 nm. In some embodiments, a lipid nanoparticle has an average size of less than 20 nm.

In addition, more homogeneous nanoparticles with narrow particle size range are achieved by a process of the present invention. For example, greater than about 70%, 75%, 80%, 85%, 90%, 95%, 96%, 97%, 98%, 99% of the purified nanoparticles in a composition provided by the present invention have a size ranging from about 75-150 nm (e.g., about 75-145 nm, about 75-140 nm, about 75-135 nm, about 75-130 nm, about 75-125 nm, about 75-120 nm, about 75-115 nm, about 75-110 nm, about 75-105 nm, about 75-100 nm, about 75-95 nm, about 75-90 nm, or 75-85 nm). In some embodiments, substantially all of the purified nanoparticles have a size ranging from about 75-150 nm (e.g., about 75-145 nm, about 75-140 nm, about 75-135 nm, about 75-130 nm, about 75-125 nm, about 75-120 nm, about 75-115 nm, about 75-110 nm, about 75-105 nm, about 75-100 nm, about 75-95 nm, about 75-90 nm, or 75-85 nm).

In some embodiments, the dispersity, or measure of heterogeneity in size of molecules (PDI), of nanoparticles encapsulating mRNA provided by the present invention is less than about 0.5. In some embodiments, a lipid nanoparticle has a PDI of less than about 0.4. In some embodiments, a lipid nanoparticle has a PDI of less than about 0.3. In some embodiments, a lipid nanoparticle has a PDI of less than about 0.28. In some embodiments, a lipid nanoparticle has a PDI of less than about 0.25. In some embodiments, a lipid nanoparticle has a PDI of less than about 0.23 (e.g., less than about 0.23, 0.22, 0.21, 0.20, 0.19, 0.18, 0.17, 0.16, 0.15, 0.14, 0.13, 0.12, 0.11, 0.10, 0.09, or 0.08). In a particular embodiment, the PDI is less than about 0.16.

In some embodiments, greater than about 75%, 80%, 85%, 90%, 95%, 96%, 97%, 98%, or 99% of the purified lipid nanoparticles in a composition provided by the present invention encapsulate an mRNA within each individual particle. In some embodiments, substantially all of the purified lipid nanoparticles in a composition encapsulate an mRNA within each individual particle. In some embodiments, a lipid nanoparticle has an encapsulation efficiency of between 50% and 99%. In some embodiments, a lipid nanoparticle has an encapsulation efficiency of greater than about 60%. In some embodiments, a lipid nanoparticle has an encapsulation efficiency of greater than about 65%. In some embodiments, a lipid nanoparticle has an encapsulation efficiency of greater than about 70%. In some embodiments, a lipid nanoparticle has an encapsulation efficiency of greater than about 75%. In some embodiments, a lipid nanoparticle has an encapsulation efficiency of greater than about 80%. In some embodiments, a lipid nanoparticle has an encapsulation efficiency of greater than about 85%. In some embodiments, a lipid nanoparticle has an encapsulation efficiency of greater than about 90%. In some embodiments, a lipid nanoparticle has an encapsulation efficiency of greater than about 92%. In some embodiments, a lipid nanoparticle has an encapsulation efficiency of greater than about 95%. In some embodiments, a lipid nanoparticle has an encapsulation efficiency of greater than about 98%. In some embodiments, a lipid nanoparticle has an encapsulation efficiency of greater than about 99%. Typically, lipid nanoparticles for use with the invention have an encapsulation efficiency of at least 90%-95%.

In some embodiments, a composition according to the present invention is formulated so as to administer doses to a subject. In some embodiments, a composition of mRNA lipid nanoparticles as described herein is formulated at a dose concentration of less than 1.0 mg/kg mRNA lipid nanoparticles (e.g., 0.6 mg/kg, 0.5 mg/kg, 0.3 mg/kg, 0.016 mg/kg. 0.05 mg/kg, and 0.016 mg/kg. In some embodiments, the dose is decreased due to the unexpected finding that lower doses yield high potency and efficacy. In some embodiments, the dose is decreased by about 70%, 65%, 60%, 55%, 50%, 45% or 40%.

In some embodiments, the potency of mRNA-encapsulating lipid nanoparticles produced by a Step Up Remix and/or Step Down Remix process is from more than 100% (i.e., more than 200%, more than 300%, more than 400%, more than 500%, more than 600%, more than 700%, more than 800%, or more than 900%) to more than 1000% more potent when prepared by the Step Up Remix and/or Step Down Remix process as compared to Process B.

Therapeutic Use of Compositions

The present invention also provides delivering a composition of the invention for use in the treatment of a subject, e.g., a human subject or a cell of a human subject or a cell that is treated and delivered to a human subject.

Techniques for formulation and administration of compositions of the invention may be found in "Remington's Pharmaceutical Sciences," Mack Publishing Co., Easton, Pa., latest edition.

Provided mRNA-loaded nanoparticles, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical, and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

Delivery Methods

The present invention provides methods of delivering mRNA for in vivo protein production, comprising administering mRNA to a subject in need of delivery. In some embodiments, mRNA is administered via a route of delivery selected from the group consisting of intravenous delivery, subcutaneous delivery, oral delivery, subdermal delivery, ocular delivery, intratracheal injection pulmonary delivery (e.g. nebulization), intramuscular delivery, intrathecal delivery, or intraarticular delivery.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In some embodiments, the intramuscular administration is to a muscle selected from the group consisting of skeletal muscle, smooth muscle and cardiac muscle. In some embodiments the administration results in delivery of the mRNA to a muscle cell. In some embodiments the administration results in delivery of the mRNA to a hepatocyte (i.e., liver cell). In a particular embodiment, the intramuscular administration results in delivery of the mRNA to a muscle cell.

The choice of administration route depends on the target cell or tissues. Systemic delivery of the mRNA-encoded protein or peptide may be achieved, e.g., by intravenous, intramuscular or pulmonary administration of the mRNA, typically encapsulated in a lipid nanoparticle (e.g., a liposome). Intravenous delivery can be used to efficiently target hepatocytes. Intramuscular administration is typically the method of choice for delivering mRNA encoding an immunogenic protein or peptide (e.g., for use as a vaccine). Pulmonary delivery is commonly used to target the lung epithelium.

In some embodiments, mRNA-loaded lipid nanoparticles are administered by pulmonary delivery via nebulization, typically involving a suitable nebulizing apparatus (e.g., a mesh nebulizer). Additional teaching of pulmonary delivery and nebulization are described in published U.S. Application No. US 2018/0125989 and published U.S. Application No. US 2018/0333457, each of which is incorporated by reference in its entirety.

Alternatively or additionally, mRNA-loaded nanoparticles and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Dosing Regimens

Provided methods of the present invention contemplate single as well as multiple administrations of a therapeutically effective amount of the therapeutic agents (e.g., mRNA) described herein. Therapeutic agents can be administered at regular intervals, depending on the nature, severity and extent of the subject's condition. In some embodiments, a therapeutically effective amount of the therapeutic agents (e.g., mRNA) of the present invention may be administered intrathecally periodically at regular intervals (e.g., once every year, once every six-months, once every five-months, once every three-months, bimonthly (once every two-months), monthly (once every month), biweekly (once every two-weeks), twice a month, once every 30-days, once every 28-days, once every 14-days, once every 10-days, once every 7-days, weekly, twice a week, daily, or continuously).

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating a disease or disorder). For example, a therapeutically effective amount may be an amount sufficient to achieve a desired therapeutic and/or prophylactic effect. Generally, the amount of a therapeutic agent (e.g., mRNA) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg body weight.

In some embodiments, the therapeutically effective dose is greater than about 0.1 mg/kg body weight, greater than about 0.5 mg/kg body weight, greater than about 1.0 mg/kg body weight, greater than about 3.0 mg/kg body weight, greater than about 5.0 mg/kg body weight, greater than about 10 mg/kg body weight, greater than about 15 mg/kg body weight, greater than about 20 mg/kg body weight, greater than about 30 mg/kg body weight, greater than about 40 mg/kg body weight, greater than about 50 mg/kg body weight, greater than about 60 mg/kg body weight, greater than about 70 mg/kg body weight, greater than about 80 mg/kg body weight, greater than about 90 mg/kg body weight, greater than about 100 mg/kg body weight, greater than about 150 mg/kg body weight, greater than about 200 mg/kg body weight, greater than about 250 mg/kg body weight, greater than about 300 mg/kg body weight, greater than about 350 mg/kg body weight, greater than about 400 mg/kg body weight, greater than about 450 mg/kg body weight, greater than about 500 mg/kg body weight. In a particular embodiment, the therapeutically effective dose is 1.0 mg/kg. In some embodiments, the therapeutically effective dose of 1.0 mg/kg is administered intramuscularly or intravenously.

According to various embodiments, the timing of expression of delivered mRNA can be tuned to suit a particular medical need. In some embodiments, the expression of the protein encoded by delivered mRNA is detectable 1, 2, 3, 6, 12, 24, 48, 72, and/or 96 hours after administration of provided liposomes and/or compositions. In some embodiments, the expression of the protein encoded by delivered mRNA is detectable one-week, two-weeks, and/or one-month after administration.

Relative Potency and Efficacy of Compositions of the Invention

In some embodiments, administering the provided composition results in an increased mRNA expression level in a biological sample from a subject as compared to an equivalent composition formulated using the "Step Up Remix" and/or "Step Down Remix" processes described herein. Biological samples include, for example, whole blood, serum, plasma, urine and tissue samples (e.g., muscle, liver, skin fibroblasts). In some embodiments, administering the provided composition results in an increased mRNA expression level by at least about 10%, 20%, 30%, 40%, 50%, 60%, 70%, 80%, 90%, or 95% compared to an equivalent composition formulated using the "Step Up Remix" and/or "Step Down Remix" processes described herein.

Specific Peptides, Polypeptides and Proteins for Use with the Invention

In certain embodiments the present invention provides a method for producing a therapeutic composition comprising mRNA molecules that encode a peptide or polypeptide for use in the delivery to or treatment of the lung of a subject or a lung cell. In certain embodiments the present invention provides a method for producing a therapeutic composition having mRNA molecules that encode for cystic fibrosis transmembrane conductance regulator (CFTR) protein. In certain embodiments the present invention provides a method for producing a therapeutic composition having mRNA molecules that encode for ATP-binding cassette sub-family A member 3 protein. In certain embodiments the present invention provides a method for producing a therapeutic composition having mRNA molecules that encode for dynein axonemal intermediate chain 1 protein. In certain embodiments the present invention provides a method for producing a therapeutic composition having mRNA molecules that encode for dynein axonemal heavy chain 5 (DNAH5) protein. In certain embodiments the present invention provides a method for producing a therapeutic composition having mRNA molecules that encode for alpha-1-antitrypsin protein. In certain embodiments the present invention provides a method for producing a therapeutic composition having mRNA molecules that encode for forkhead box P3 (FOXP3) protein. In certain embodiments the present invention provides a method for producing a therapeutic composition having mRNA molecules that encode one or more surfactant protein, e.g., one or more of surfactant A protein, surfactant B protein, surfactant C protein, and surfactant D protein.

In certain embodiments the present invention provides a method for producing a therapeutic composition having mRNA molecules that encode a peptide or polypeptide for use in the delivery to or treatment of the liver of a subject or a liver cell. Such peptides and polypeptides can include those associated with a urea cycle disorder, associated with a lysosomal storage disorder, with a glycogen storage disorder, associated with an amino acid metabolism disorder, associated with a lipid metabolism or fibrotic disorder, associated with methylmalonic acidemia, or associated with any other metabolic disorder for which delivery to or treatment of the liver or a liver cell with enriched mRNA molecules provide a therapeutic benefit.

In certain embodiments the present invention provides a method for producing a therapeutic composition having mRNA molecules that encode for a protein associated with a urea cycle disorder. In certain embodiments the present invention provides a method for producing a therapeutic composition having mRNA molecules that encode for ornithine transcarbamylase (OTC) protein. In certain embodiments the present invention provides a method for producing a therapeutic composition having mRNA molecules that encode for argininoosuccinate synthetase 1 protein. In certain embodiments the present invention provides a method for producing a therapeutic composition having mRNA molecules that encode for carbamoyl phosphate synthetase I protein. In certain embodiments the present invention provides a method for producing a therapeutic composition having mRNA molecules that encode for argininosuccinate lyase protein. In certain embodiments the present invention provides a method for producing a therapeutic composition having mRNA molecules that encode for arginase protein.

In certain embodiments the present invention provides a method for producing a therapeutic composition having mRNA molecules that encode for a protein associated with a lysosomal storage disorder. In certain embodiments the present invention provides a method for producing a therapeutic composition having mRNA molecules that encode for alpha galactosidase protein. In certain embodiments the present invention provides a method for producing a therapeutic composition having mRNA molecules that encode for glucocerebrosidase protein. In certain embodiments the present invention provides a method for producing a therapeutic composition having mRNA molecules that encode for iduronate-2-sulfatase protein. In certain embodiments the present invention provides a method for producing a therapeutic composition having mRNA molecules that encode for iduronidase protein. In certain embodiments the present invention provides a method for producing a therapeutic composition having mRNA molecules that encode for N-acetyl-alpha-D-glucosaminidase protein. In certain embodiments the present invention provides a method for producing a therapeutic composition having mRNA molecules that encode for heparan N-sulfatase protein. In certain embodiments the present invention provides a method for producing a therapeutic composition having mRNA molecules that encode for galactosamine-6 sulfatase protein. In certain embodiments the present invention provides a method for producing a therapeutic composition having mRNA molecules that encode for beta-galactosidase protein. In certain embodiments the present invention provides a method for producing a therapeutic composition having mRNA molecules that encode for lysosomal lipase protein. In certain embodiments the present invention provides a method for producing a therapeutic composition having mRNA molecules that encode for arylsulfatase B (N-acetylgalactosamine-4-sulfatase) protein. In certain embodiments the present invention provides a method for producing a therapeutic composition having mRNA molecules that encode for transcription factor EB (TFEB).

In certain embodiments the present invention provides a method for producing a therapeutic composition having mRNA molecules that encode for a protein associated with a glycogen storage disorder. In certain embodiments the present invention provides a method for producing a therapeutic composition having mRNA molecules that encode for acid alpha-glucosidase protein. In certain embodiments the present invention provides a method for producing a therapeutic composition having mRNA molecules that encode for glucose-6-phosphatase (G6PC) protein. In certain embodiments the present invention provides a method for producing a therapeutic composition having mRNA molecules that encode for liver glycogen phosphorylase protein. In certain embodiments the present invention provides a method for producing a therapeutic composition having mRNA molecules that encode for muscle phosphoglycerate mutase protein. In certain embodiments the present invention provides a method for producing a therapeutic composition having mRNA molecules that encode for glycogen debranching enzyme.

In certain embodiments the present invention provides a method for producing a therapeutic composition having mRNA molecules that encode for a protein associated with amino acid metabolism. In certain embodiments the present invention provides a method for producing a therapeutic composition having mRNA molecules that encode for phenylalanine hydroxylase enzyme. In certain embodiments the present invention provides a method for producing a therapeutic composition having mRNA molecules that encode for glutaryl-CoA dehydrogenase enzyme. In certain embodiments the present invention provides a method for producing a therapeutic composition having mRNA molecules that encode for propionyl-CoA caboxylase enzyme. In certain embodiments the present invention provides a method for producing a therapeutic composition having mRNA molecules that encode for oxalase alanine-glyoxylate aminotransferase enzyme.

In certain embodiments the present invention provides a method for producing a therapeutic composition having mRNA molecules that encode for a protein associated with a lipid metabolism or fibrotic disorder. In certain embodiments the present invention provides a method for producing a therapeutic composition having mRNA molecules that encode for a mTOR inhibitor. In certain embodiments the present invention provides a method for producing a therapeutic composition having mRNA molecules that encode for ATPase phospholipid transporting 8B1 (ATP8B1) protein. In certain embodiments the present invention provides a method for producing a therapeutic composition having mRNA molecules that encode for one or more NF-kappa B inhibitors, such as one or more of I-kappa B alpha, interferon-related development regulator 1 (IFRD1), and Sirtuin 1 (SIRT1). In certain embodiments the present invention provides a method for producing a therapeutic composition having mRNA molecules that encode for PPAR-gamma protein or an active variant.

In certain embodiments the present invention provides a method for producing a therapeutic composition having mRNA molecules that encode for a protein associated with methylmalonic acidemia. For example, in certain embodiments the present invention provides a method for producing a therapeutic composition having mRNA molecules that encode for methylmalonyl CoA mutase protein. In certain embodiments the present invention provides a method for producing a therapeutic composition having mRNA molecules that encode for methylmalonyl CoA epimerase protein.

In certain embodiments the present invention provides a method for producing a therapeutic composition having full-length mRNA for which delivery to or treatment of the liver can provide therapeutic benefit. In certain embodiments the present invention provides a method for producing a therapeutic composition having mRNA molecules that encode for ATP7B protein, also known as Wilson disease protein. In certain embodiments the present invention provides a method for producing a therapeutic composition having mRNA molecules that encode for porphobilinogen deaminase enzyme. In certain embodiments the present invention provides a method for producing a therapeutic composition having mRNA molecules that encode for one or clotting enzymes, such as Factor VIII, Factor IX, Factor VII, and Factor X. In certain embodiments the present invention provides a method for producing a therapeutic composition having mRNA molecules that encode for human hemochromatosis (HFE) protein.

In certain embodiments the present invention provides a method for producing a therapeutic composition having mRNA molecules that encode a peptide or polypeptide for use in the delivery to or treatment of the cardiovasculature of a subject or a cardiovascular cell. In certain embodiments the present invention provides a method for producing a therapeutic composition having mRNA molecules that encode for vascular endothelial growth factor A protein. In certain embodiments the present invention provides a method for producing a therapeutic composition having mRNA molecules that encode for relaxin protein. In certain embodiments the present invention provides a method for producing a therapeutic composition having mRNA molecules that encode for bone morphogenetic protein-9 protein. In certain embodiments the present invention provides a method for producing a therapeutic composition having mRNA molecules that encode for bone morphogenetic protein-2 receptor protein.

In certain embodiments the present invention provides a method for producing a therapeutic composition having mRNA molecules that encode a peptide or polypeptide for use in the delivery to or treatment of the muscle of a subject or a muscle cell. In certain embodiments the present invention provides a method for producing a therapeutic composition having mRNA molecules that encode for dystrophin protein. In certain embodiments the present invention provides a method for producing a therapeutic composition having mRNA molecules that encode for frataxin protein. In certain embodiments the present invention provides a method for producing a therapeutic composition having mRNA molecules that encode a peptide or polypeptide for use in the delivery to or treatment of the cardiac muscle of a subject or a cardiac muscle cell. In certain embodiments the present invention provides a method for producing a therapeutic composition having mRNA molecules that encode for a protein that modulates one or both of a potassium channel and a sodium channel in muscle tissue or in a muscle cell. In certain embodiments the present invention provides a method for producing a therapeutic composition having mRNA molecules that encode for a protein that modulates a Kv7.1 channel in muscle tissue or in a muscle cell. In certain embodiments the present invention provides a method for producing a therapeutic composition having mRNA molecules that encode for a protein that modulates a Nav1.5 channel in muscle tissue or in a muscle cell.

In certain embodiments the present invention provides a method for producing a therapeutic composition having RNA molecules that encode a peptide or polypeptide for use in the delivery to or treatment of the nervous system of a subject or a nervous system cell. For example, in certain embodiments the present invention provides a method for producing a therapeutic composition having mRNA molecules that encode for survival motor neuron 1 protein. For example, in certain embodiments the present invention provides a method for producing a therapeutic composition having mRNA molecules that encode for survival motor neuron 2 protein. In certain embodiments the present invention provides a method for producing a therapeutic composition having mRNA molecules that encode for frataxin protein. In certain embodiments the present invention provides a method for producing a therapeutic composition having mRNA molecules that encode for ATP binding cassette subfamily D member 1 (ABCD1) protein. In certain embodiments the present invention provides a method for producing a therapeutic composition having mRNA molecules that encode for CLN3 protein.

In certain embodiments the present invention provides a method for producing a therapeutic composition having mRNA molecules that encode a peptide or polypeptide for use in the delivery to or treatment of the blood or bone marrow of a subject or a blood or bone marrow cell. In certain embodiments the present invention provides a method for producing a therapeutic composition having mRNA molecules that encode for beta globin protein. In certain embodiments the present invention provides a method for producing a therapeutic composition having mRNA molecules that encode for Bruton's tyrosine kinase protein. In certain embodiments the present invention provides a method for producing a therapeutic composition having mRNA molecules that encode for one or clotting enzymes, such as Factor VIII, Factor IX, Factor VII, and Factor X.

In certain embodiments the present invention provides a method for producing a therapeutic composition having mRNA molecules that encode a peptide or polypeptide for use in the delivery to or treatment of the kidney of a subject or a kidney cell. In certain embodiments the present invention provides a method for producing a therapeutic composition having mRNA molecules that encode for collagen type IV alpha 5 chain (COL4A5) protein.

In certain embodiments the present invention provides a method for producing a therapeutic composition having mRNA molecules that encode a peptide or polypeptide for use in the delivery to or treatment of the eye of a subject or an eye cell. In certain embodiments the present invention provides a method for producing a therapeutic composition having mRNA molecules that encode for ATP-binding cassette sub-family A member 4 (ABCA4) protein. In certain embodiments the present invention provides a method for producing a therapeutic composition having mRNA molecules that encode for retinoschisin protein. In certain embodiments the present invention provides a method for producing a therapeutic composition having mRNA molecules that encode for retinal pigment epithelium-specific 65 kDa (RPE65) protein. In certain embodiments the present invention provides a method for producing a therapeutic composition having mRNA molecules that encode for centrosomal protein of 290 kDa (CEP290).

In certain embodiments the present invention provides a method for producing a therapeutic composition having mRNA molecules that encode a peptide or polypeptide for use in the delivery of or treatment with a vaccine for a subject or a cell of a subject. For example, in certain embodiments the present invention provides a method for producing a therapeutic composition having mRNA molecules that encode for an antigen from an infectious agent, such as a virus. In certain embodiments the present invention provides a method for producing a therapeutic composition having mRNA molecules that encode for an antigen from influenza virus. In certain embodiments the present invention provides a method for producing a therapeutic composition having mRNA molecules that encode for an antigen from respiratory syncytial virus. In certain embodiments the present invention provides a method for producing a therapeutic composition having mRNA molecules that encode for an antigen from rabies virus. In certain embodiments the present invention provides a method for producing a therapeutic composition having mRNA molecules that encode for an antigen from cytomegalovirus. In certain embodiments the present invention provides a method for producing a therapeutic composition having mRNA molecules that encode for an antigen from rotavirus. In certain embodiments the present invention provides a method for producing a therapeutic composition having mRNA molecules that encode for an antigen from a hepatitis virus, such as hepatitis A virus, hepatitis B virus, or hepatitis C virus. In certain embodiments the present invention provides a method for producing a therapeutic composition having mRNA molecules that encode for an antigen from human papillomavirus. In certain embodiments the present invention provides a method for producing a therapeutic composition having mRNA molecules that encode for an antigen from a herpes simplex virus, such as herpes simplex virus 1 or herpes simplex virus 2. In certain embodiments the present invention provides a method for producing a therapeutic composition having mRNA molecules that encode for an antigen from a human immunodeficiency virus, such as human immunodeficiency virus type 1 or human immunodeficiency virus type 2. In certain embodiments the present invention provides a method for producing a therapeutic composition having mRNA molecules that encode for an antigen from a human metapneumovirus. In certain embodiments the present invention provides a method for producing a therapeutic composition having mRNA molecules that encode for an antigen from a human parainfluenza virus, such as human parainfluenza virus type 1, human parainfluenza virus type 2, or human parainfluenza virus type 3. In certain embodiments the present invention provides a method for producing a therapeutic composition having mRNA molecules that encode for an antigen from malaria virus. In certain embodiments the present invention provides a method for producing a therapeutic composition having mRNA molecules that encode for an antigen from zika virus. In certain embodiments the present invention provides a method for producing a therapeutic composition having mRNA molecules that encode for an antigen from chikungunya virus.

In certain embodiments the present invention provides a method for producing a therapeutic composition having mRNA molecules that encode for an antigen associated with a cancer of a subject or identified from a cancer cell of a subject. In certain embodiments the present invention provides a method for producing a therapeutic composition having mRNA molecules that encode for an antigen determined from a subject's own cancer cell, i.e., to provide a personalized cancer vaccine. In certain embodiments the present invention provides a method for producing a therapeutic composition having mRNA molecules that encode for an antigen expressed from a mutant KRAS gene.

In certain embodiments the present invention provides a method for producing a therapeutic composition having mRNA molecules that encode for an antibody. In certain embodiments, the antibody can be a bi-specific antibody. In certain embodiments, the antibody can be part of a fusion protein. In certain embodiments the present invention provides a method for producing a therapeutic composition having mRNA molecules that encode for an antibody to OX40. In certain embodiments the present invention provides a method for producing a therapeutic composition having mRNA molecules that encode for an antibody to VEGF. In certain embodiments the present invention provides a method for producing a therapeutic composition having mRNA molecules that encode for an antibody to tissue necrosis factor alpha. In certain embodiments the present invention provides a method for producing a therapeutic composition having mRNA molecules that encode for an antibody to CD3. In certain embodiments the present invention provides a method for producing a therapeutic composition having mRNA molecules that encode for an antibody to CD19.

In certain embodiments the present invention provides a method for producing a therapeutic composition having mRNA molecules that encode for an immunomodulator. In certain embodiments the present invention provides a method for producing a therapeutic composition having mRNA molecules that encode for Interleukin 12. In certain embodiments the present invention provides a method for producing a therapeutic composition having mRNA molecules that encode for Interleukin 23. In certain embodiments the present invention provides a method for producing a therapeutic composition having mRNA molecules that encode for Interleukin 36 gamma. In certain embodiments the present invention provides a method for producing a therapeutic composition having mRNA molecules that encode for a constitutively active variant of one or more stimulator of interferon genes (STING) proteins.

In certain embodiments the present invention provides a method for producing a therapeutic composition having mRNA molecules that encode for an endonuclease. In certain embodiments the present invention provides a method for producing a therapeutic composition having mRNA molecules that encode for an RNA-guided DNA endonuclease protein, such as Cas 9 protein. In certain embodiments the present invention provides a method for producing a therapeutic composition having mRNA molecules that encode for a meganuclease protein. In certain embodiments the present invention provides a method for producing a therapeutic composition having mRNA molecules that encode for a transcription activator-like effector nuclease protein. In certain embodiments the present invention provides a method for producing a therapeutic composition having mRNA molecules that encode for a zinc finger nuclease protein.

In some embodiments, the compositions and methods of the invention provide for the delivery of mRNA encoding a therapeutic peptide, polypeptide or protein to a subject, wherein the subject suffers from disease or disorder that is due to a deficiency in the peptide, polypeptide or protein encoded by the mRNA in the subject. The deficiency may be due to non-expression of the peptide, polypeptide or protein; expression of a non-functional peptide, polypeptide or protein, a dysfunctional peptide, polypeptide or protein, or peptide, polypeptide or protein with reduced function; or other functional impediment to the peptide, polypeptide or proteins. Diseases or disorders of this nature are commonly referred to as "protein deficiencies". Typically, these diseases or disorders are caused by one or more mutations in the gene encoding said peptide, polypeptide or protein in the subject. The replacement peptide, polypeptide or protein encoded by the mRNA does not include the one or more mutations that are the underlying cause of the protein deficiency. Diseases or disorders that are due to a protein deficiency include cystic fibrosis, lysosomal storage diseases, metabolic disorders (e.g., urea cycle disorders) etc.

In other embodiments, the compositions and methods of the invention provide for the delivery of mRNA encoding a therapeutic peptide, polypeptide or protein. Such therapeutic peptides, polypeptides or proteins include antibodies, immunogens, cytokines, allergens etc.

In some embodiments, the compositions and methods of the invention provide for the delivery of mRNA encoding a therapeutic protein (e.g., cytosolic, transmembrane or secreted).

In some embodiments, the present invention is used to prevent, treat and/or cure a subject affected with a disease or disorder listed or associated with the proteins listed above. In some embodiments, an mRNA encodes one or more of Cystic Fibrosis Transmembrane Conductance Regulator (CFTR), argininosuccinate synthetase (ASS1), Factor IX, survival motor neuron 1 (SMN1), or phenylalanine hydroxylase (PAH). In some embodiments, the present invention is used to prevent, treat and/or cure a subject affected with any one of cystic fibrosis, citrullinemia, hemophilia B, spinal muscular atrophy and phenylketonuria.

EXAMPLES

While certain compounds, compositions and methods of the present invention have been described with specificity in accordance with certain embodiments, the following examples serve only to illustrate the invention and are not intended to limit the same.

Example 1. Lipid Nanoparticle Formulation Processes with Preformed Lipid Nanoparticles A cationic lipid, a non-cationic lipid (DOPE), cholesterol and a PEG-modified lipid (DMG-PEG2K) were dissolved in ethanol and mixed with citrate buffer using a pump system. The instantaneous mixing of the two streams resulted in the formation of empty 4-component lipid nanoparticles through a self-assembly process. The formulation was then subjected to a TFF purification process, removing the citrate buffer and alcohol and exchanging it for storage buffer (10% trehalose). The resulting suspension of preformed empty lipid nanoparticles was then mixed with mRNA according to one of the three processes described below.

Figure 1A:
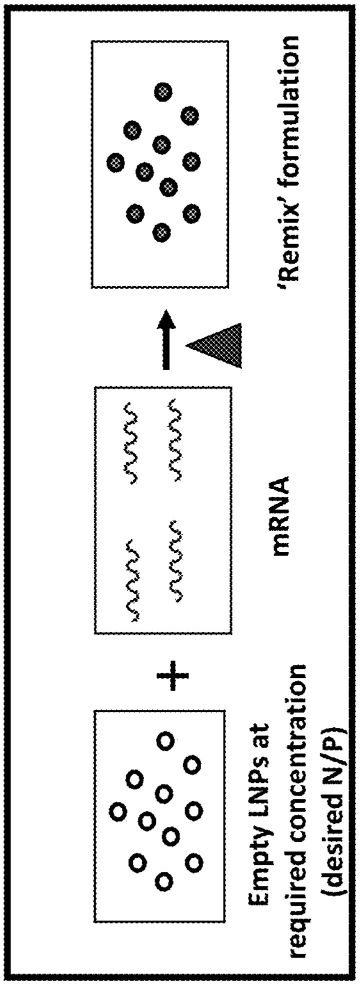
Figure 1C:
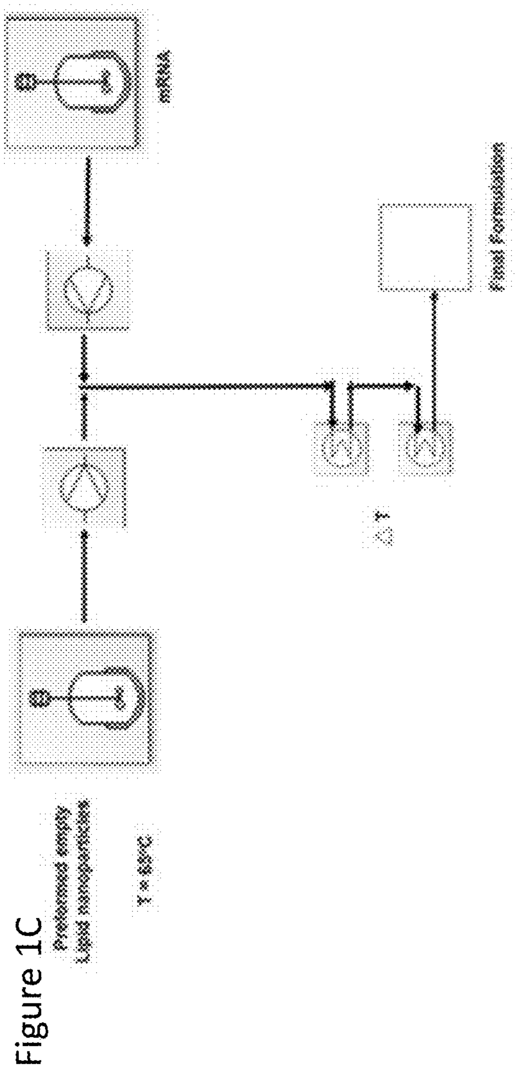

In a first experiment, a suspension of preformed empty lipid nanoparticles was heated to 65° C. and mixed with a room temperature solution of mRNA encoding the protein ornithine transcarbamylase (OTC). It was previously observed that a 4-fold molar excess of cationic lipid per mol mRNA is advantageous to yield a high percentage of encapsulated mRNA. This ratio has been found suitable independent of the actual number of positively charged nitrogens (N) relative to negatively charged phosphates (P) in the mRNA molecule that is to be encapsulated, but is nevertheless colloquially referred to as an "N/P ratio" of 4. This "Remix" process yielded a suspension of lipid nanoparticles encapsulating the OTC mRNA, as shown schematically in FIG. 1A. The N/P ratio relative to the formulation process time is shown in FIG. 1B. Mixing of the heated lipid nanoparticles with the room temperature mRNA solution was done using a pump system as illustrated in FIG. 1C.

Figure 2A:
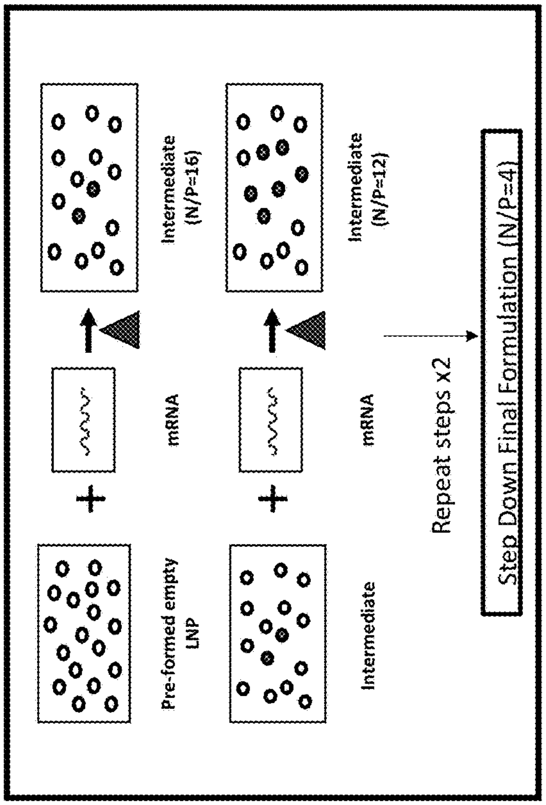
FIGS. 2A-2D show improved processes that builds on the conventional "Remix" process.
Figure 2B:
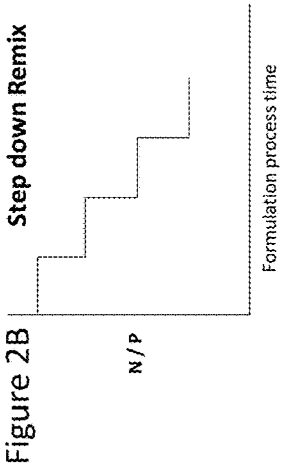

Instead of mixing all of the mRNA with all of the preformed empty lipid nanoparticles in a single step to achieve a desired N/P ratio, the mRNA or preformed empty lipid nanoparticles can also be mixed in a stepwise fashion, increasing ("Step Up") or decreasing ("Step Down") the N/P ratio until the desired ratio is achieved. Accordingly, in a second experiment, a first volume of mRNA was added to preformed empty lipid nanoparticles (as used in the Remix experiment above) to yield an intermediate suspension with an N/P ratio of 16 (i.e., an excess of preformed empty lipid nanoparticles). Then an additional volume was added to yield a new intermediate suspension with an N/P ratio of 12. These steps were repeated two more times until a final N/P ratio of 4 was achieved. This "Step Down Remix" process yielded a suspension of lipid nanoparticles encapsulating the mRNA. The process is illustrated schematically in FIG. 2A. The N/P ratio relative to the formulation process time for this process is shown in FIG. 2B.

Figure 2C:
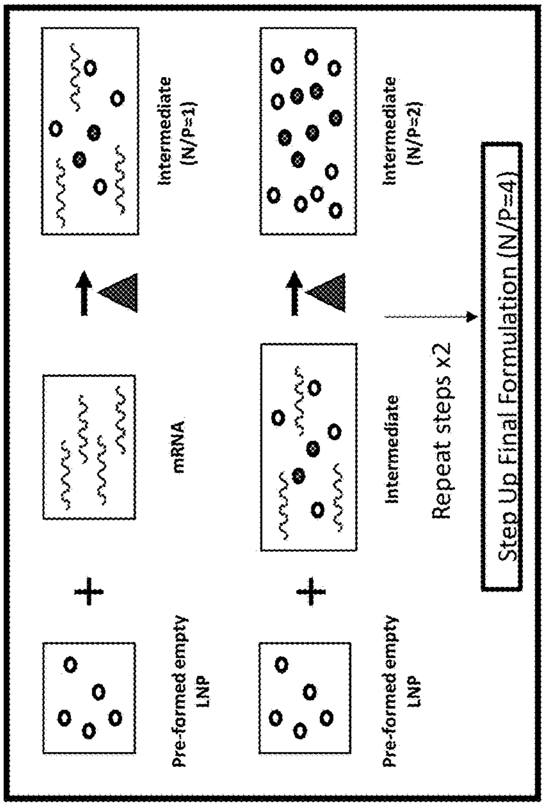
Figure 2D:
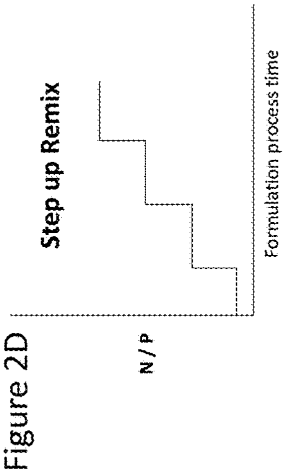

In a third experiment, a first volume of preformed empty lipid nanoparticles (as used in the Remix and Step Down experiments above) was added to a solution of mRNA to yield an intermediate suspension with an N/P ratio of 1. Then an additional volume of preformed empty lipid nanoparticles was added to a solution of mRNA to yield an intermediate suspension with an N/P ratio of 2. These steps were repeated two more times until a final N/P ratio of 4 was achieved. This "Step Up Remix" process yielded a suspension of lipid nanoparticles encapsulating the mRNA. The process is illustrated schematically in FIG. 2C. The N/P ratio relative to the formulation process time for this process is shown in FIG. 2D.

For the conventional "Remix" process, it was found to be advantageous to heat the preformed empty lipid nanoparticles to 65° C. prior to mixing and the combine it with a room temperature solution of mRNA. During mixing, the combined suspension is heated to 65° C. Typically, mixing is performed for at least 15 minutes to ensure that the maximum amount of mRNA is encapsulated in the lipid nanoparticles. Heating during mixing was shown to dramatically increase encapsulation efficiency.

Figure 3A:
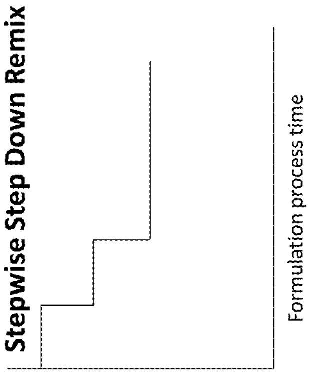
FIGS. 3A-3F show alternative versions to the exemplary Step Down and Step Up Remix processes shown in FIGS. 2A-2D. For example.
Figure 3B:
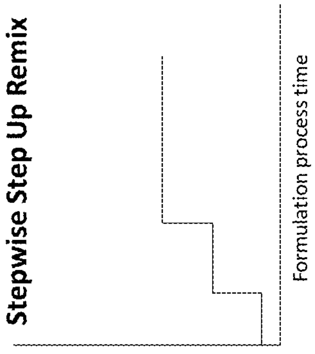
Figure 3C:
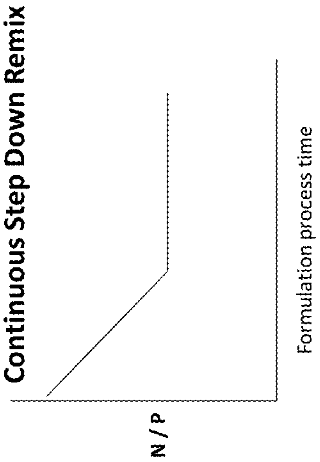
Figure 3D:
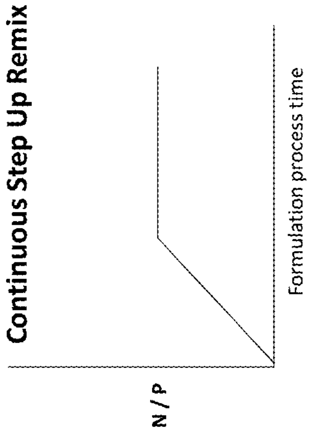
Figure 3E:
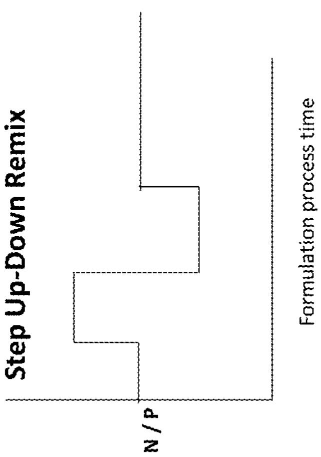
Figure 3F:
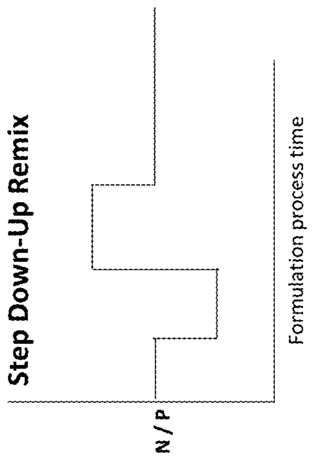

Accordingly, for both the "Step Down Remix" and the "Step Up Remix" processes, the suspension containing the preformed empty lipid nanoparticles was heated to 65° C. prior to mixing. After addition of each batch of mRNA ("Step Down Remix") or empty lipid nanoparticles ("Step Up Remix"), the combined suspension was heated to 65° C. during mixing. In order to ensure mRNA integrity, it is preferable to minimize the heat exposure of the mRNA solution. It was found that 4 minutes of mixing and heating after addition of each batch was sufficient for obtaining mRNA-loaded lipid nanoparticle formulations with improved characteristics relative to formulations prepared with the conventional "Remix" process. In particular with respect to the "Step Down Remix" process, this is considered advantageous because only one quarter of the mRNA is exposed to heat for approximately the same length of time as during the conventional "Remix" process, minimizing degradation as a consequence of heat exposure. This advantage is realized whether the mRNA is added to the lipid nanoparticles in several volumes followed by mixing for a set period of time (thus adjusting the N/P ratio in a stepwise fashion as shown in FIG. 3A), or continuously during mixing over a period of time until the desired N/P ratio is achieved (as illustrated in FIG. 3C).

Example 2. In Vivo Protein Expression from hOTC mRNA in Wildtype CDJ Mice

This example illustrates how stepwise alteration of the N/P ratio during the mixing of preformed lipid nanoparticles with mRNA can result in lipid nanoparticles that are more potent in inducing protein expression from the encapsulated mRNA.

Intravenous (IV) administration of two exemplary 4-component lipid nanoparticles was performed, both nanoparticles comprising a non-cationic lipid (DOPE), cholesterol and a PEG-modified lipid (DMG-PEG2K) and hOTC mRNA. The first formulation comprised a cDD-TE-4-E12 cationic lipid, while the second formulation comprised a cDD-TE-4-E10 cationic lipid. Studies with both formulations were undertaken in order to study mRNA delivery and resultant hOTC protein expression. Male CD1 mice at 6-8 weeks old were given a single bolus tail-vein injection of one of six formulations: either the cDD-TE-4-E10 or cDD-TE-4-E12 nanoparticles, each formed by one of the Remix, Step Down, or Step Up processes (i.e. six formulations in total). These were prepared as described in Example 1 at a hOTC mRNA dose of 1.0 mg/kg. The mice were sacrificed and perfused with saline 24 hours post-administration. Liver tissue was collected, and hOTC protein expression levels were measured in liver homogenate by ELISA.

Figure 4A:
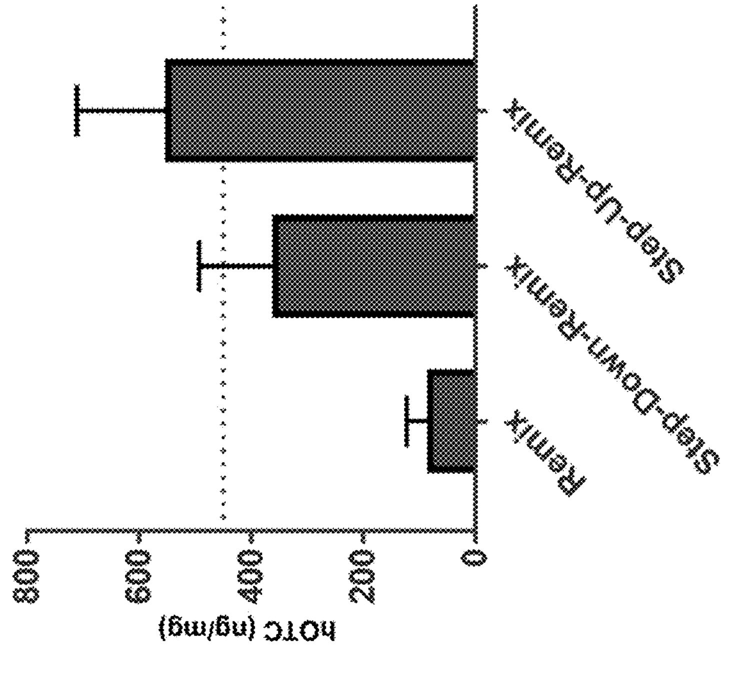
FIGS. 4A-4B illustrate in vivo protein expression from hOTC mRNA in the liver of wildtype CD1 mice for two lipid formulations, differing in that the cationic lipid is either cDD-TE-4-E10 (FIG. 4A) or that the cationic lipid is cDD-TE-4-E12 (FIG. 4B). The mRNA was formulated in lipid nanoparticles using the exemplary Remix, Step Down Remix, and Step Up Remix processes shown in FIGS. 1A-1C and 2A-2D. 6-8 weeks old male mice were given a single bolus tail-vein injection of the lipid nanoparticle formulations at a hOTC mRNA dose of 1.0 mg/kg. Liver homogenates were analyzed by ELISA to determine the amount of hOTC relative to total protein (shown in ng/mg). In each figure, the dashed line represents the approximate minimum expression level for therapeutic efficacy (about 450 ng hOTC per mg total protein).
Figure 4B:
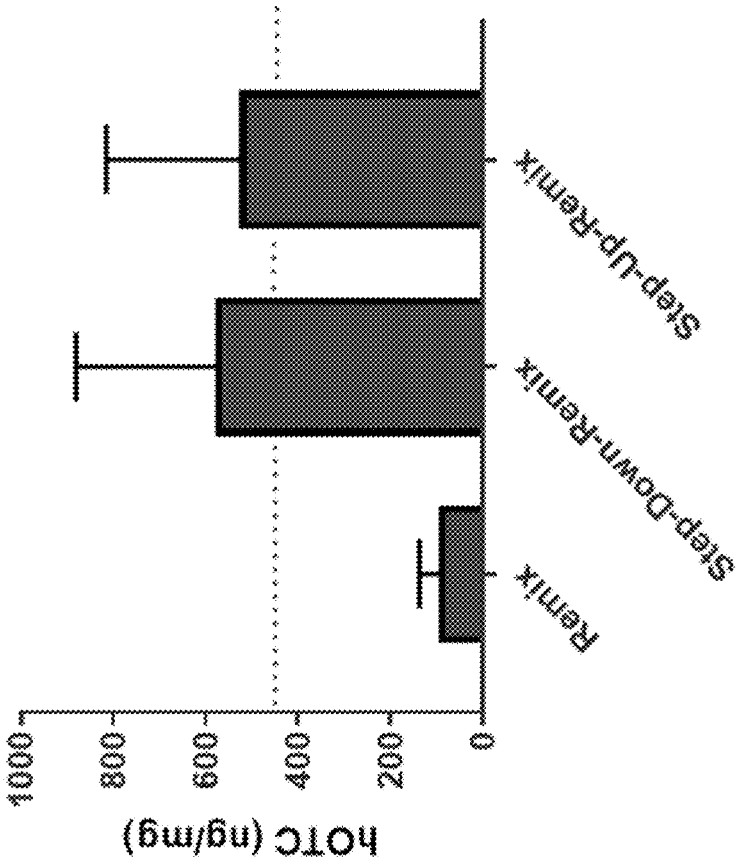

As shown in FIGS. 4A-4B, all three tested lipid nanoparticle formulations for cDD-TE-4-E10 (FIG. 4A) and all three tested lipid nanoparticle formulations for cDD-TE-4-E12 (FIG. 4B) were effective in delivering mRNA to the liver in vivo and resulted in expression of OTC protein encoded by the delivered mRNA. Surprisingly, however, the “Step Up Remix” and “Step Down Remix” processes resulted in formulations that were up to about 6 times more potent in inducing protein expression than the formulation prepared by the “Remix” process. In each figure, the dashed line represents the approximate minimum expression level for therapeutic efficacy (about 450 ng hOTC per mg total protein).

While both formulations exhibited improved expression when formulated by Step Up Remix or Step Down Remix, cDD-TE-4-E12 (a cationic lipid with 12-carbon alkyl chains) demonstrated improved expression relative to cDD-TE-4-E10 (a cationic lipid with 10-carbon alkyl chains). Without wishing to be bound by any particular theory, the inventors believe that Step Up Remix and Step Down Remix processes increase potency of the encapsulated mRNA (as assessed by in vivo protein expression) more effectively when the lipid formulation is prepared with a cationic lipid having longer alkyl chains.

Example 3. Improved In Vivo Expression of hOTC mRNA after Intravenous Delivery with Optimized Lipid Nanoparticle Formulations This example illustrates that stepwise alteration of the N/P ratio during the loading of preformed lipid nanoparticles with mRNA can further augment the potency of a lipid nanoparticle formulation, even if the lipid composition has already been optimized to maximize protein expression.

The cationic lipid plays a decisive role in determining the in vivo potency of a 4-component lipid nanoparticle formulation. Therefore, optimizing this lipid component can result in dramatic increases in potency of the resulting lipid nanoparticle. Moreover, it has been demonstrated that the potency of 4-component lipid nanoparticles can be further enhanced by replacing the non-cationic lipid component DOPE with DEPE (see U.S. provisional application 62/871,513, filed on Jul. 8, 2019, which is incorporated herein by reference in its entirety).

A first 4-component lipid nanoparticle was prepared with the optimized cationic lipid cDD-TE-4-E12, DOPE, cholesterol and DMG-PEG2K. A second 4-component lipid nanoparticle was prepared that was cDD-TE-4-E12, DEPE, cholesterol and DMG-PEG2K (i.e. identical to the second formulation, except that DOPE was replaced with DEPE as the non-cationic lipid component).

The first and second lipid nanoparticles were prepared using either the “Remix” process, the “Step Down Remix” process or the “Step Up Remix” process as described in Example 1, resulting in 6 lipid nanoparticle formulations. These lipid nanoparticle formulations were administered to male CD-1 mice as described in Example 2. They are summarized in the following table.

TABLE 3

Exemplary lipid nanoparticle formulations

| Lipid formulation | Process | Encapsulation |
|---|---|---|
| CDD-TE-4-E12, DOPE, cholesterol and DMG-PEG2K | Remix | 85.73% |
| CDD-TE-4-E12, DOPE, cholesterol and DMG-PEG2K | Step Down | 92.70% |
| CDD-TE-4-E12, DOPE, cholesterol and DMG-PEG2K | Step Up | 89.90% |
| CDD-TE-4-E12, DEPE, cholesterol and DMG-PEG2K | Remix | 91.60% |
| CDD-TE-4-E12, DEPE, cholesterol and DMG-PEG2K | Step Down | 96.06% |
| CDD-TE-4-E12, DEPE, cholesterol and DMG-PEG2K | Step Up | 95.66% |

Figure 5:
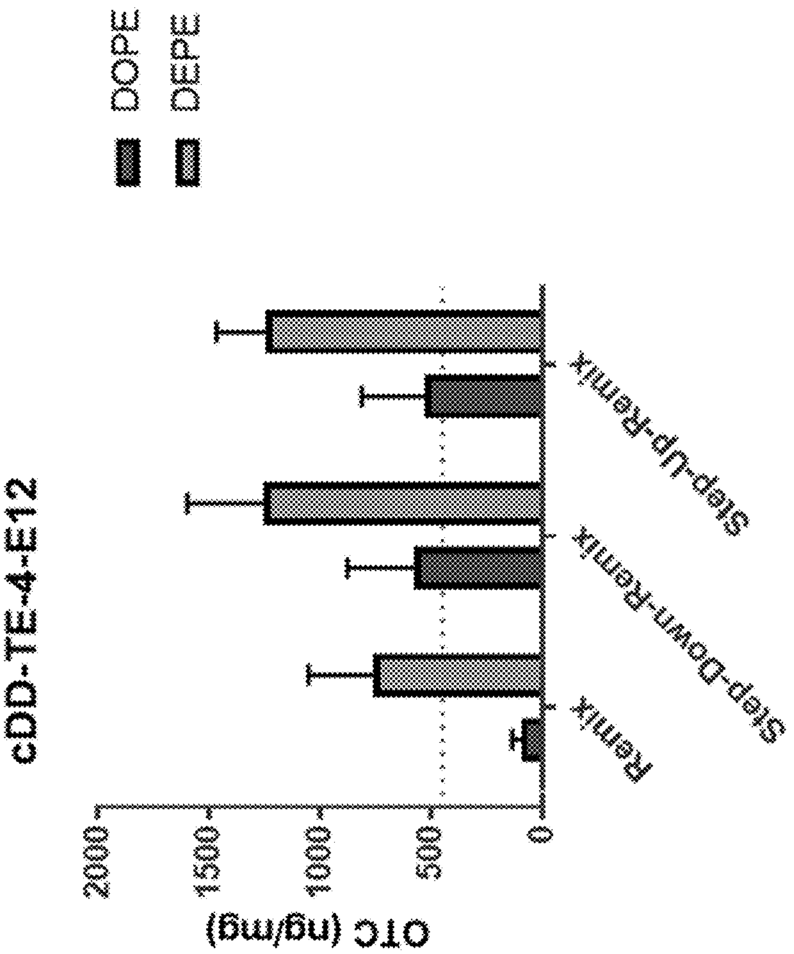
FIG. 5 illustrates that lipid nanoparticles formulated with exemplary Step Down and Step Up Remix processes can improve in vivo expression of hOTC mRNA relative to lipid nanoparticles formulated with a conventional Remix process, even when optimized lipid nanoparticle formulations are used. 6-8 weeks old male mice were given a single bolus tail-vein injection of the lipid nanoparticle formulations at a hOTC mRNA dose of 1.0 mg/kg. cDD-TE-4-E12-based 4-component liposomes with either DOPE or DEPE as the non-cationic lipid component were used as the test article. MC3-based lipid nanoparticles served as a control. Liver homogenates were analyzed by ELISA to determine the amount of hOTC relative to total protein (shown in ng/mg).

As shown in FIG. 5, all 6 tested lipid nanoparticle formulations were effective in delivering mRNA to the liver in vivo and resulted in expression of OTC protein encoded by the delivered mRNA. As observed in Example 2, Step Up Remix and Step Down Remix resulted in formulations that were many times more potent than those prepared by “Remix”. Surprisingly, potency gains were still observed with a highly optimized lipid nanoparticle formulation comprising the cationic lipid cDD-TE-4-E12 and the non-cationic lipid DEPE instead of DOPE. While potency gains were less pronounced with such a highly optimized formulation, OTC expression nearly doubled when the “Step Down Remix” process or the “Step Up Remix” process were used in place of the “Remix” process. Although not achieving a statistically significant difference, there was a trend for the “Step Down Remix” formulations to outperform the “Step Up Remix” formulations, presumably due to increased mRNA integrity as a result of reduced heat exposure of the mRNA. Accordingly, the “Step Down Remix” process was selected for further experiments.

Example 4. Improved In Vivo Expression of hOTC mRNA after Intravenous Delivery with Lipid Nanoparticle Formulations Prepared Using Different Numbers of Steps This example illustrates that the gradual adjustment of the N/P ratio in smaller step changes during encapsulation of mRNA into preformed lipid nanoparticles can result in lipid nanoparticles that are even more potent in inducing protein expression from the encapsulated mRNA than lipid nanoparticles prepared by processes with large(r) step changes of the N/P ratio.

A 4-component lipid nanoparticle comprising the cationic lipid cKK-E12 (also known as TBL-0346 or ML-(DOPE), cholesterol and a PEG-modified lipid (DMG-PEG2K) and hOTC mRNA was prepared as summarized in Table 4. Apart from the different number of steps, the preparation methods were the same as the "Step Up Remix" and "Step Down Remix" processes described in Example 1. The total process time was 16 minutes to minimize the duration during which the mRNA is exposed to elevated temperatures. Male CD1 mice at 6-8 weeks old were given a single bolus tail-vein injection of one of the four formulations at a hOTC mRNA dose of 0.5 mg/kg. The mice were sacrificed and perfused with saline 24 hours post-administration. Liver tissue was collected, and hOTC protein expression levels were measured in liver homogenate by ELISA.

TABLE 4

Exemplary lipid nanoparticle formulations

| Process | Steps | Size (nm) | PDI | Encap-sulation |
|---|---|---|---|---|
| Step Down | Four steps, a period of 4 minutes of mixing while heating after addition of each batch, the steps producing N/P values of 16, 8, 5.33, and 4 | 100 | 0.122 | 85% |
| Step Down | Eight steps, a period of 2 minutes of mixing while heating after addition of each batch, the steps producing N/P values of 32, 16, 10.67, 8, 6.4, 5.33, 4.57, and 4 | 107 | 0.181 | 81% |
| Step Up | Four steps, a period of 4 minutes of mixing while heating after addition of each batch, the steps producing N/P values of 1, 2, 3, 4 | 103 | 0.156 | 77% |
| Step Up | Eight steps, a period of 2 minutes of mixing while heating after addition of each batch, the steps producing N/P values of 1, 1.5, 2, 2.5, 3, 3.5, 4 | 116 | 0.176 | 76% |

Figure 6A:
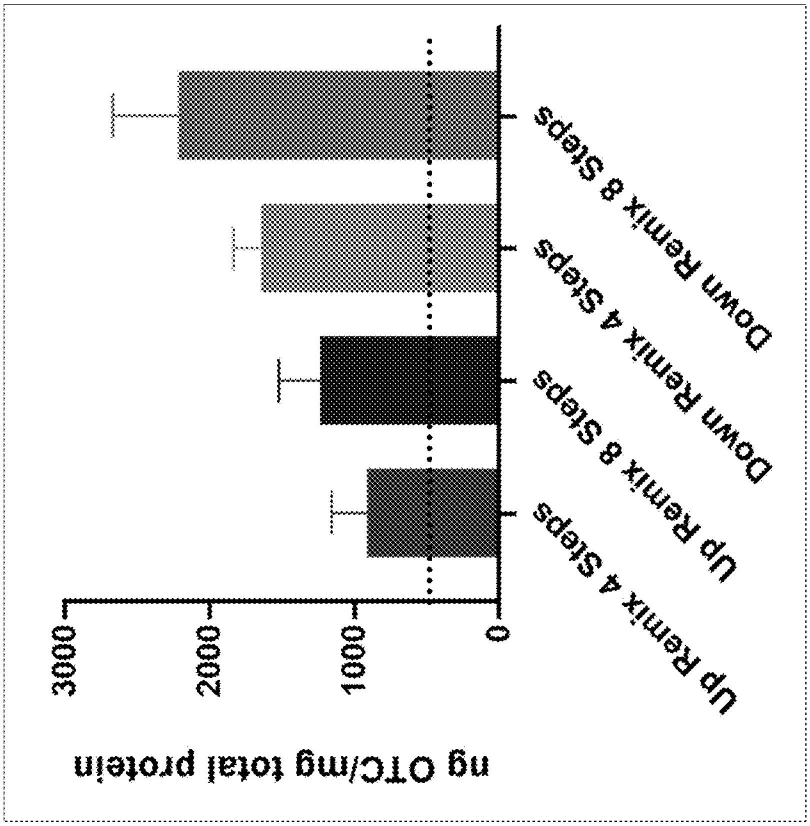
FIGS. 6A-6B illustrate that adjusting the number of steps (FIG. 6A) or the timing of the addition of batches (FIG. 6B) in exemplary Step Down and Step Up Remix processes can improve in vivo expression of hOTC mRNA. 6-8 weeks old male mice were given a single bolus tail-vein injection of the various lipid nanoparticle formulations at a hOTC mRNA dose of 0.5 mg/kg. Liver homogenates were analyzed by ELISA to determine the amount of hOTC relative to total protein (shown in ng/mg). In each figure, the dashed line represents the approximate minimum expression level for therapeutic efficacy (about 450 ng hOTC per mg total protein).

As shown in FIG. 6A, all four tested lipid nanoparticle formulations were effective in delivering mRNA to the liver in vivo and resulted in expression of OTC protein encoded by the delivered mRNA. Increasing the number of steps from four to eight improved OTC expression in both Step Up Remix and Step Down Remix formulations.

This example demonstrates that increasing the number of steps that are taken to achieve a predetermined N/P ratio further improves the potency of the resulting lipid nanoparticles, suggesting that a gradual adjustment of the N/P ratio in smaller step changes may be advantageous during encapsulation of mRNA into preformed lipid nanoparticles.

Example 5. Improved In Vivo Expression of hOTC mRNA after Intravenous Delivery with Lipid Nanoparticle Formulations Prepared Using Different Timing of Addition This example illustrates that a period of continuous alteration of the N/P ratio during the encapsulation of mRNA into preformed lipid nanoparticles results in mRNA-encapsulating lipid nanoparticles that are highly effective in inducing protein expression from the encapsulated mRNA.

A 4-component lipid nanoparticle comprising the cationic lipid cKK-E12 (also known as TBL-0346 or ML-2), and a PEG-modified lipid (DMG-PEG2K) and hOTC mRNA was prepared as summarized in Table 5. Apart from the timing of the stepwise additions, the preparation methods were the same as the "Step Up Remix" and "Step Down Remix" processes described in Example 1. The total process time was 16 minutes to minimize the duration during which the mRNA is exposed to elevated temperatures. Male CD1 mice at 6-8 weeks old were given a single bolus tail-vein injection of one of the four formulations at a hOTC mRNA dose of 0.5 mg/kg. The mice were sacrificed and perfused with saline 24 hours post-administration. Liver tissue was collected, and hOTC protein expression levels were measured in liver homogenate by ELISA.

TABLE 5

Exemplary lipid nanoparticle formulations

| Process | Steps | Size (nm) | PDI | Encap-sulation |
|---|---|---|---|---|
| Step Down | Four steps, a period of 4 minutes of mixing while heating after addition of each batch, the steps producing N/P values of 16, 8, 5.33, and 4 | 100 | 0.122 | 85% |
| Step Down | Four steps, no period of mixing while heating after addition of each batch, the steps producing N/P values of 16, 8, 5.33, and 4 | 109 | 0.16 | 82% |
| Step Up | Four steps, a period of 4 minutes of mixing while heating after addition of each batch, the steps producing N/P values of 1, 2, 3, 4 | 103 | 0.156 | 77% |
| Step Up | Four steps, no period of mixing while heating after addition of each batch, the steps producing N/P values of 1, 2, 3, 4 | 112 | 0.201 | 68% |

Figure 6B:
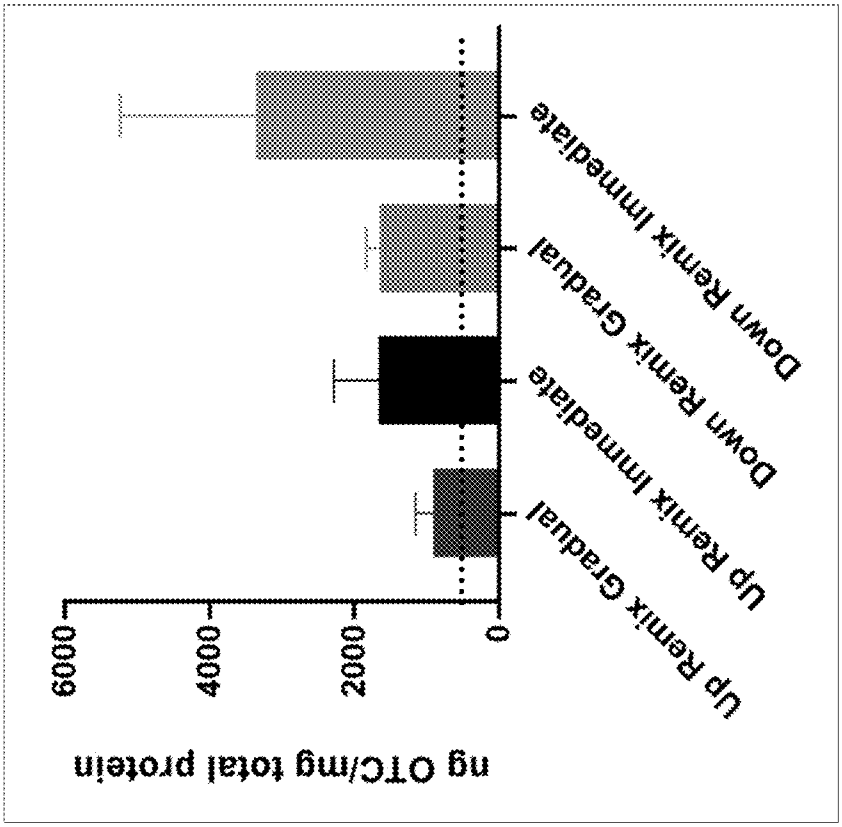

As shown in FIG. 6B, all four tested lipid nanoparticle formulations were effective in delivering mRNA to the liver in vivo and resulted in expression of OTC protein encoded by the delivered mRNA. Omitting mixing and heating after the addition of each step improved OTC expression in both Step Up Remix and Step Down Remix formulations. This beneficial effect on formulation potency was independent of the encapsulation efficiency for each formulation.

This example demonstrates that sequential stepwise alteration of the N/P ratio during encapsulation of mRNA into preformed lipid nanoparticle does not require intervening periods of mixing and heating to result in mRNA-encapsulating lipid nanoparticles that are highly efficient in inducing protein expression from the encapsulated mRNA. Rather, highly potent mRNA-encapsulating lipid nanoparticles can be prepared by the continuous addition of mRNA to preformed lipid nanoparticles. These results suggest that, although encapsulation of the mRNA occurs rapidly, the potency of the final mRNA-encapsulating lipid nanoparticle can be improved significantly by the gradual alteration of the N/P ratio during the encapsulation process.

Example 6. In Vivo Activity of hOTC mRNA in OTC$^{spf ash}$ Mice after 24 Hours This example illustrates that optimization of the formulation process results in potent lipid nanoparticle formulation that is highly effective in providing a missing protein through delivery of an mRNA encoding that protein, even at low mRNA dose levels.

Figure 7A:
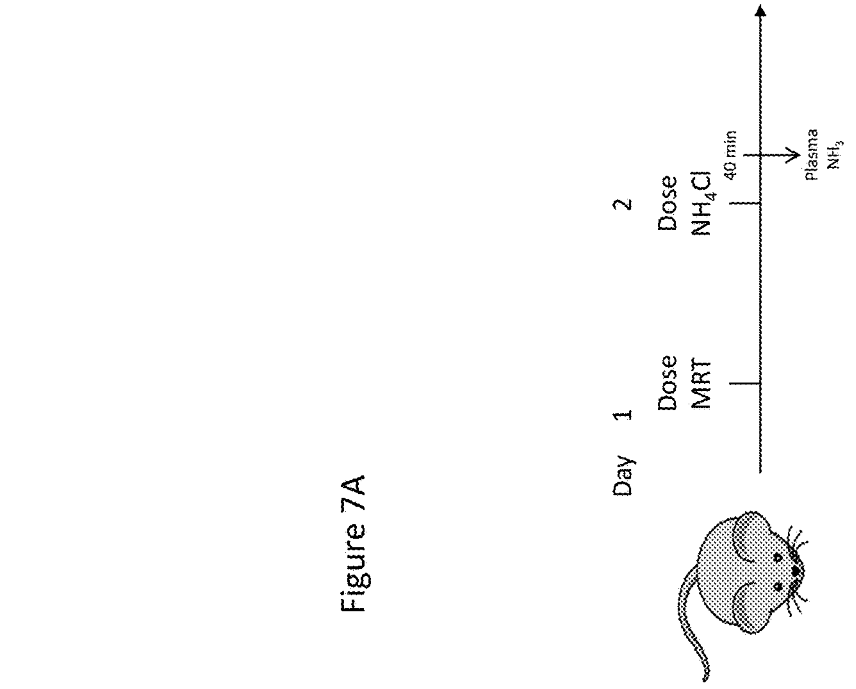
FIGS. 7A-7C illustrate the dose-dependent in vivo activity of hOTC mRNA in $OTC^{spfash}$ mice 24 hours after a single bolus injection of mRNA.

In this example, five OTC$^{spf ash}$ mice were administered a single dose of hOTC mRNA encapsulated in a lipid nanoparticle prepared by the "Step Down Remix" process described in Example 1. Its lipid composition was identical to lipid composition of the second 4-component lipid nanoparticle tested in Example 3 (cDD-TE-4-E12, DEPE, cholesterol, and DMG-PEG2K). Saline-treated wild-type and OTC$^{spf ash}$ mice served as controls. 24 hours post dose the animals were challenged with $NH_4Cl$, and plasma $NH_3$ levels were measured 40 minutes post challenge, as illustrated in FIG. 7A. At the conclusion of the experiment, the mice were terminated, and liver tissues from the mice were isolated and analyzed for OTC protein production using ELISA.

Figure 7B:
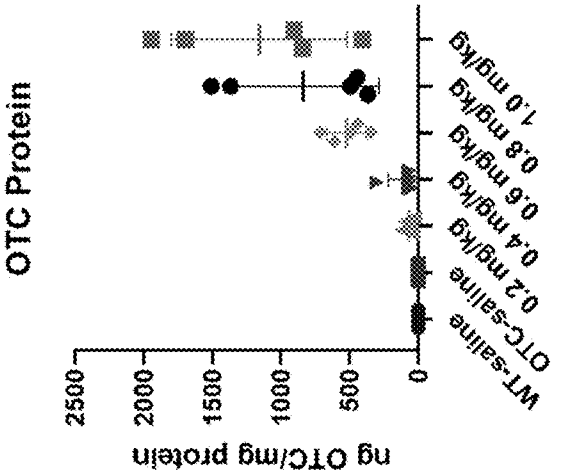
Figure 7C:
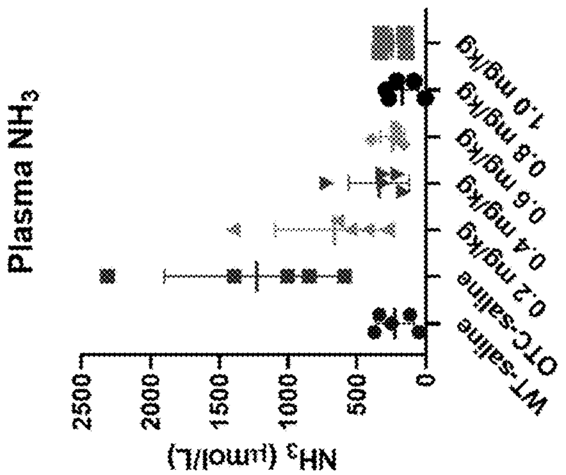

FIG. 7B shows that the amount of OTC protein detectable in the liver of $OTC^{spf/ash}$ mice increased in a dose-dependent fashion of hOTC mRNA administered to the animals. The results shown in FIG. 7C confirm that the expressed OTC protein is active in the liver and is effective at reduced plasma $NH_3$ levels in a dose-dependent manner. Starting from a dose of 0.4 mg/kg, plasma $NH_3$ levels in the treated mice were indistinguishable from the plasma $NH_3$ levels observed in saline-treated wildtype mice.

Example 7. In Vivo Activity of hOTC mRNA in $OTC^{spf/ash}$ Mice Weeks after Administration This example illustrates that mRNA encapsulated into lipid nanoparticles by the "Step Up Remix" or "Step Down Remix" processes remains active in vivo for at least 15 days post administration.

In this example, eight $OTC^{spf/ash}$ mice were administered a single 0.3 mg/kg dose of hOTC mRNA encapsulated in lipid nanoparticles prepared as described in Example 3. Saline-treated wild-type and $OTC^{spf/ash}$ mice served as controls. Animals were challenged with $NH_4Cl$ at 1, 2, 3 and 4 weeks post dose and plasma $NH_3$ levels were measured 40 minutes post challenge, as illustrated in FIG. 8A.

Figures 8A, 8B:
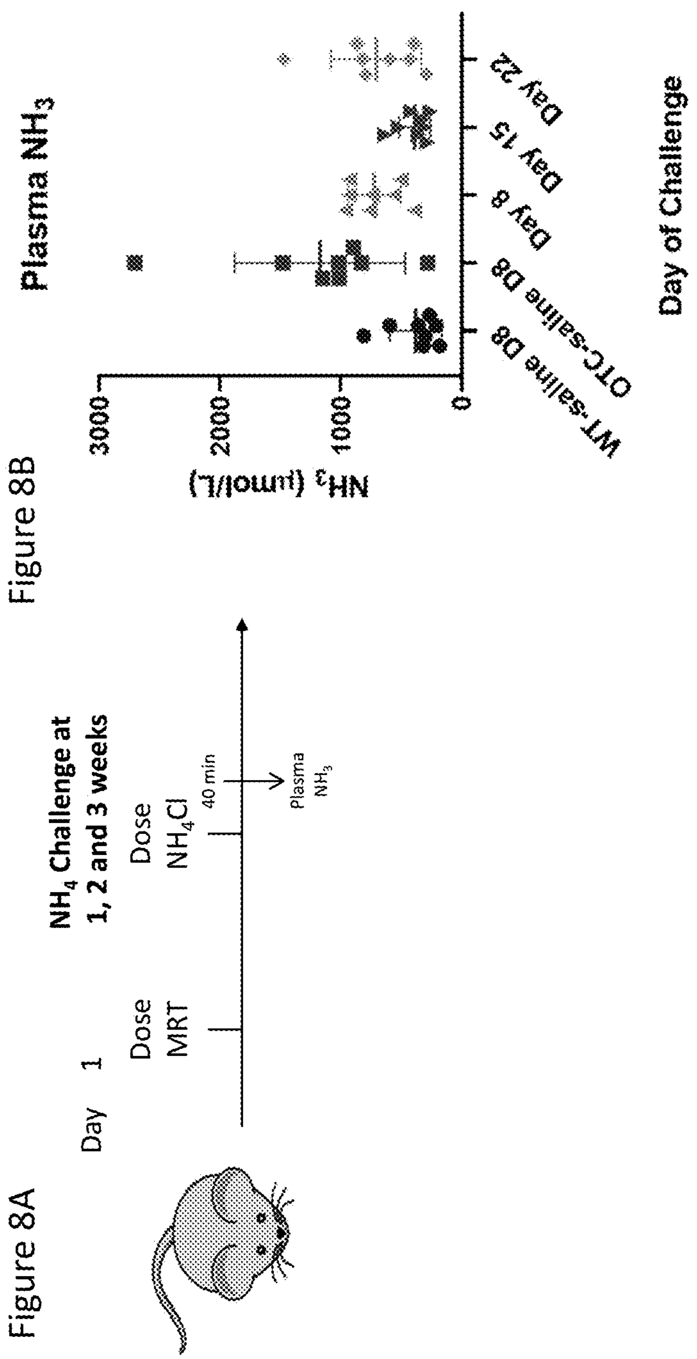
FIGS. 8A-8B illustrate the persistence of in vivo activity of hOTC mRNA in $OTC^{spf/ash}$ mice up to three weeks after a single bolus injection of mRNA.

As shown in FIG. 8B, even at a reduced dose of 0.3 mg/kg, the lipid nanoparticle formulation was effective at delivering sufficient amounts of hOTC mRNA to the liver of mice to result in amounts of OTC protein adequate to reduce plasma $NH_3$ levels to levels close to or undistinguishable from saline-treated wildtype mice for at least 15 days post administration. These results compare favorably to those of a previous study in which a 3 times higher dose (1.0 mg/kg) of hOTC mRNA delivered encapsulated in lipid nanoparticles prepared by the conventional "Remix" process yielded similar results (see Example 15 in International Patent Publication WO 2018/089801).

Example 8. The Addition of Empty Lipid Nanoparticles Boost the In Vivo Activity of hOTC mRNA in Wildtype Mice This example illustrates that the addition of empty lipid nanoparticles to an mRNA-encapsulating lipid nanoparticle formulation prepared with the conventional "Remix" process can also boost the potency of the resulting formulation.

Without wishing to be bound by any particular theory, the inventors believe that the stepwise increase ("Step Up") or decrease ("Step Down") of the N/P ratio when mixing mRNA with preformed empty lipid nanoparticles to achieve a desired N/P ratio results in fewer cationic lipids being associated with each mRNA molecule. This, in turn, makes more unbound cationic lipids available for fusion with the endosomal membrane after cellular uptake, so that the mRNA cargo is released more efficiently into the cytoplasm.

Accordingly, the mere presence of "free" cationic lipids in the endosomal compartment could therefore make endosomal escape more likely, independent of whether the "free" cationic lipid is associated with the same lipid nanoparticle that contains cationic lipids associated with mRNA or whether the "free" cationic lipid is provided by "empty" lipid nanoparticles that enter the endosomal compartment together with mRNA-loaded lipid nanoparticles.

Figure 9:
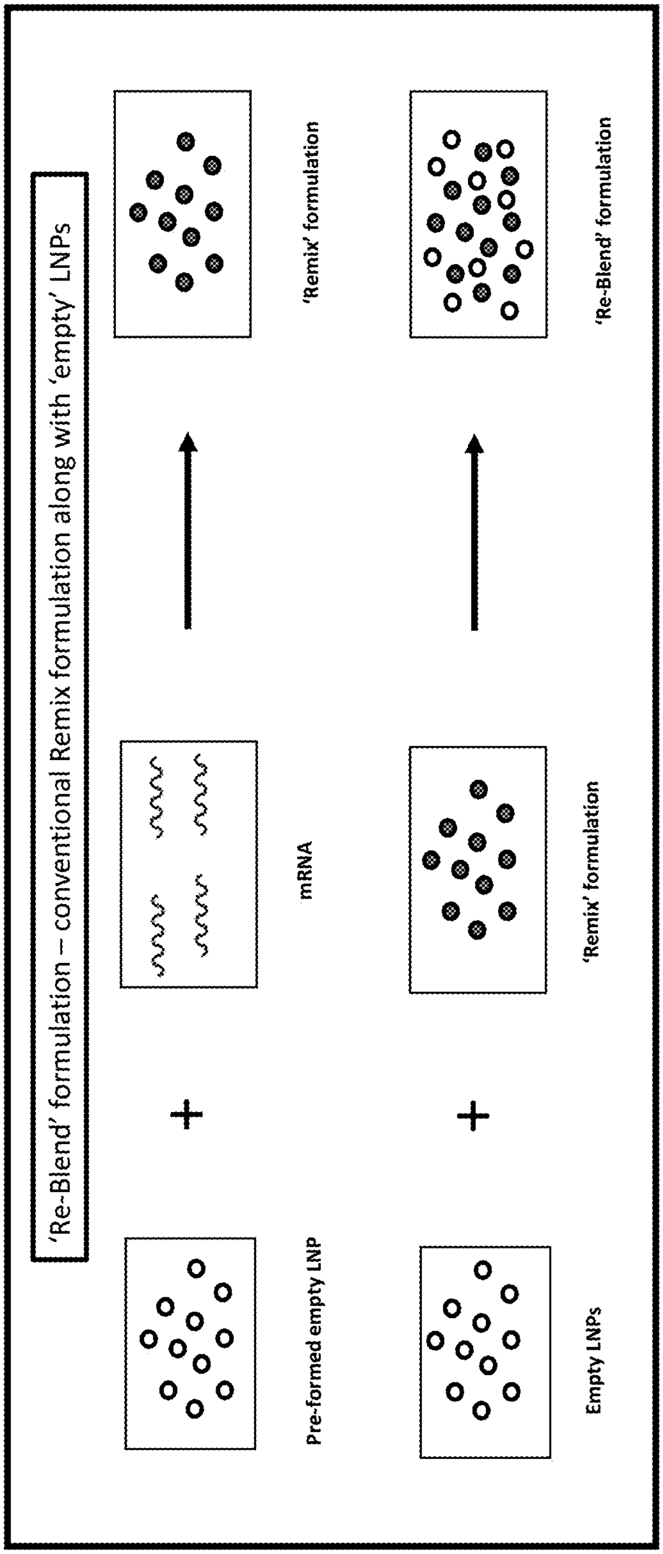
FIG. 9 illustrates a variation of the "Remix" process that is shown schematically in FIG. 1A. Pre-formed empty lipid nanoparticles are mixed with mRNA dissolved in an aqueous buffer to encapsulate it. Following the encapsulation and purification, the mRNA-loaded lipid nanoparticles are mixed with empty lipid nanoparticles to yield a mixture of mRNA-loaded and empty lipid nanoparticles ("Re-Blend Formulation"). This process is referred to herein as "Re-Blend" process.

To investigate whether the simple addition of (extra) empty lipid nanoparticles also could result in more efficient mRNA delivery, human erythropoietin (hEPO)-encoding mRNA was encapsulated into ML2-based 4-component lipid nanoparticles using the conventional "Remix" process described in Example 1. Post-encapsulation the loaded lipid nanoparticles were subjected to purification and buffer exchange using tangential flow filtration. The purified, buffered lipid nanoparticle formulations were mixed with empty lipid nanoparticles at a 1:1 ratio ("'Re-Blend' with MIL2"), as shown schematically in FIG. 9. Lipid nanoparticles prepared with the conventional "Remix" process without addition of empty lipid nanoparticles served as a control ("ML2 Remix").

Male CD1 mice at 6-8 weeks old were given a single bolus tail-vein injection of lipid nanoparticle formulations at a hEPO mRNA dose of 1.0 mg/kg or saline. Saline-treated animals served as a no-treatment control. hEPO expression was assessed in the serum of the test animals 6 hours and 24 hours post administration using ELISA. To assess whether there was any difference in tolerability between the two lipid nanoparticle formulations, the levels of ALT and AST (biomarkers for liver toxicity) were also determined.

Figure 10A:
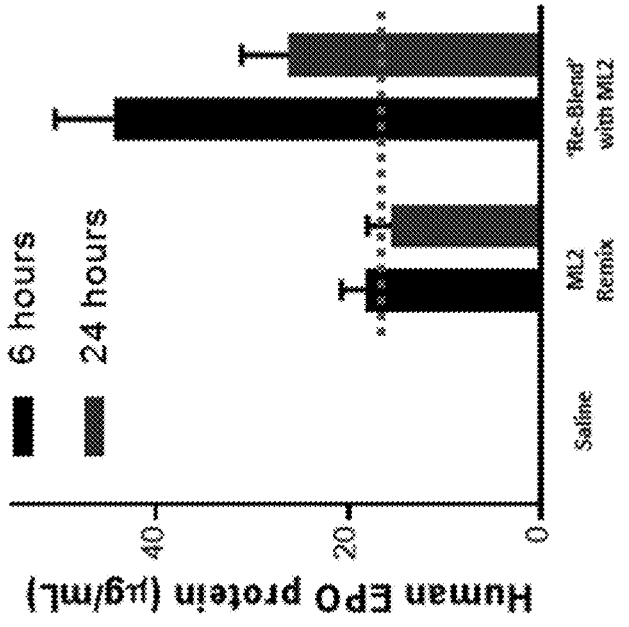
FIGS. 10A-10B illustrate how the addition of empty lipid nanoparticles to mRNA-loaded lipid nanoparticles prepared with the "Remix" process shown in FIG. 1A can boost the in vivo activity of hOTC mRNA in wildtype mice.
Figure 10B:
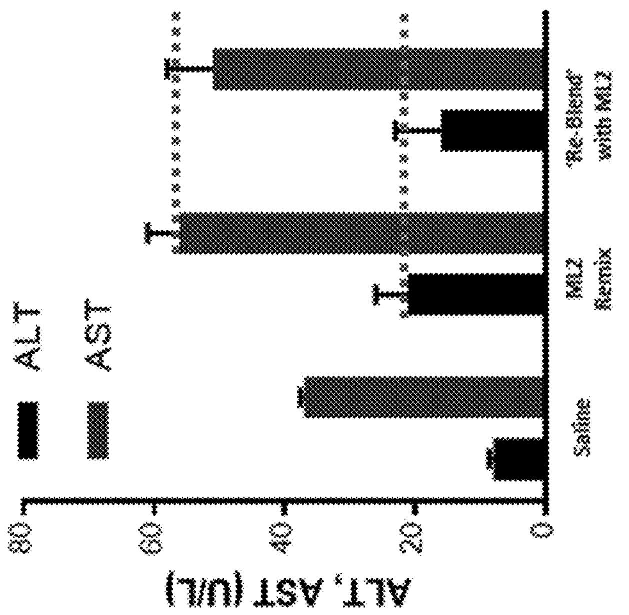

As can be seen from FIG. 10A, the control lipid nanoparticle formulation prepared with the conventional "Remix" process ("ML2 Remix") yielded serum levels of hEPO protein of about 20 μg/mL at both 6 hours and 24 hours post administration. When the same lipid nanoparticle formulation was mixed with "empty" lipid nanoparticles ("'Re-Blend' with ML2"), hEPO protein levels detectable in the serum at the 6-hour time point more than doubled. A smaller increase was seen at the 24-hour time point. The average EPO protein expression between 6 and 24 hours for the ML2 Remix control formulation is indicated with a dashed line. Tolerability was assessed on the basis of ALT and AST expression levels in the liver of the test animals. An increase in ALT and AST expression levels is indicative of liver toxicity. As can been seen from FIG. 10B, mice treated with the "Re-Blend" formulation showed comparable ALT/AST expression levels to the "ML2 Remix" benchmark. Average ALT and AST expression levels for the "ML2 Remix" control formulation are marked with dashed lines.

A general tendency has been observed that more potent cationic lipids (or larger amounts of them) are less tolerable when used for in vivo lipid nanoparticle delivery. Accordingly, an attempt to improve protein expression by using more potent cationic lipids or by administering larger amounts of a lipid nanoparticle formulation typically is negatively correlated with tolerability. The observation that the addition of empty lipid nanoparticles to a formulated composition of mRNA-encapsulating lipid nanoparticles can increase protein expression from the mRNA without change in tolerability is therefore surprising.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A composition comprising a first set of mRNA-encapsulating lipid nanoparticles (LNPs) comprising a first cationic lipid, a first non-cationic lipid, and a first PEG-modified lipid and a second set of empty LNPs comprising a second cationic lipid, a second non-cationic lipid, and a second PEG-modified lipid, wherein the first set of LNPs and the second set of LNPs are present at a ratio ranging from 20:1 to 1:20, wherein the first set of LNPs and the second set of LNPs have different lipid formulations.

2. The composition of claim 1, wherein the first cationic lipid and the second cationic lipid are different.

3. The composition of claim 1, wherein the first non-cationic lipid and the second non-cationic lipid are different.

4. The composition of claim 1, wherein the first cationic lipid and the second cationic lipid are the same and the first non-cationic lipid and the second non-cationic lipid are different.

5. The composition of claim 4, wherein the first non-cationic lipid is DOPE and the second non-cationic lipid is DEPE or wherein the first non-cationic lipid is DEPE and the second non-cationic lipid is DOPE.

6. The composition of claim 1, wherein the first set of LNPs and the second set of LNPs each have an average size ranging from about 75-150 nm in diameter.

7. The composition of claim 1, wherein the first set of LNPs and the second set of LNPs each have an average size of less than 100 nm in diameter.

8. The composition of claim 1, wherein the mRNA encodes a peptide, polypeptide or protein.

9. The composition of claim 1, wherein the first set of LNPs comprise cholesterol.

10. The composition of claim 1, wherein the second set of LNPs comprise cholesterol.

11. The composition of claim 1, wherein the first set of LNPs comprise cholesterol and wherein the second set of LNPs comprise cholesterol.

12. The composition of claim 2, wherein the first non-cationic lipid and the second non-cationic lipid are different.

13. The composition of claim 2, wherein the first cationic lipid and the second cationic lipid are the same and the first non-cationic lipid and the second non-cationic lipid are different.

14. The composition of claim 13, wherein the first non-cationic lipid is DOPE and the second non-cationic lipid is DEPE or wherein the first non-cationic lipid is DEPE and the second non-cationic lipid is DOPE.

15. The composition of claim 1, wherein the first set of LNPs and the second set of LNPs are present at a ratio ranging from 5:1 to 1:5.

16. The composition of claim 1, wherein the first set of LNPs and the second set of LNPs are present at a ratio ranging from 2:1 to 1:2.

17. The composition of claim 1, wherein the first set of LNPs and the second set of LNPs are present at a ratio ranging from 10:1 to 1:10.

18. The composition of claim 1, wherein the first set of LNPs and the second set of LNPs are present at a ratio ranging from 3:1 to 1:3.

* * * * *

SEQUENCE LISTING

```
Sequence total quantity: 5
SEQ ID NO: 1            moltype = RNA  length = 1065
FEATURE                 Location/Qualifiers
misc_feature            1..1065
                        note = chemically synthesized oligonucleotide
source                  1..1065
                        mol_type = other RNA
                        organism = synthetic construct
SEQUENCE: 1
atgctgttca accttcggat cttgctgaac aacgctgcgt tccggaatgg tcacaacttc  60
atggtccgga acttcagatg cggccagccg ctccagaaca aggtgcagct caaggggagg  120
gacctcctca ccctgaaaaa cttcaccgga gaagagatca agtacatgct gtggctgtca  180
gccgacctca aattccggat caagcagaag ggcgaatacc ttcctttgct gcagggaaag  240
tccctgggga tgatcttcga gaagcgcagc actcgcacta gactgtcaac tgaaaccggc  300
ttcgcgctgc tgggaggaca cccctgcttc ctgaccaccc aagatatcca tctgggtgtg  360
aacgaatccc tcaccgacac agcgcgggtg ctgtcgtcca tggcagacgc ggtcctcgcc  420
cgcgtgtaca agcagtctga tctggacact ctggccaagg aagcctccat tcctatcatt  480
aatggattgt ccgacctcta ccatcccatc cagattctgg ccgattatct gactctgcaa  540
gaacattaca gctccctgaa ggggcttacc ctttcgtgga tcggcgacgg caacaacatt  600
ctgcacagca ttatgatgag cgctgccaag tttggaatgc acctccaagc agcgaccccg  660
aagggatacg agccagacgc ctccgtgacg aagctggctg agcagtacgc caaggagaac  720
ggcactaagc tgctgctcac caacgaccct ctcgaagccg cccacggtgg caacgtgctg  780
atcaccgata cctggatctc catgggacag gaggaggaaa agaagaagcg cctgcaagca  840
tttcaggggt accaggtgac tatgaaaacc gccaaggtcg ccgcctcgga ctggaccttc  900
ttgcactgtc tgcccagaaa gcccgaagag gtggacgacg aggtgttcta cagcccgcgg  960
tcgctggtct ttccggaggc cgaaaacagg aagtggacta tcatggccgt gatggtgtcc  1020
ctgctgaccg attactcccc gcagctgcag aaaccaaagt tctga                 1065

SEQ ID NO: 2            moltype = RNA  length = 1239
FEATURE                 Location/Qualifiers
misc_feature            1..1239
                        note = chemically synthesized oligonucleotide
source                  1..1239
                        mol_type = other RNA
                        organism = synthetic construct
SEQUENCE: 2
atgagcagca agggcagcgt ggtgctggcc tacagcggcg gcctggacac cagctgcatc  60
ctggtgtggc tgaaggagca gggctacgac gtgatcgcct acctggccaa catcggccag  120
aaggaggact tcgaggaggc ccgcaagaag gccctgaagc tgggcgccaa gaaggtgttc  180
atcgaggacg tgagccgcga gttcgtggag gagttcatct ggcccgccat ccagagcagc  240
gccctgtacg aggaccgcta cctgctgggc accagcctgg cccgccccctg catcgcccgc  300
aagcaggtgg agatcgccca gcgcgagggc gccaagtacg tgagccacgg cgccaccggc  360
aagggcaacg accaggtgcg cttcgagctg agctgctaca gcctggcccc ccagatcaag  420
gtgatcgccc cctggcgcat gcccgagttc tacaaccgct tcaagggccg caacgacctg  480
atggagtacg ccaagcagca cggcatcccc atccccgtga cccccaagaa cccctggagc  540
atggacgaga acctgatgca catcagctac gaggccggca tcctggagaa ccccaagaac  600
caggcccccc ccggcctgta caccaagacc caggaccccg ccaaggcccc caacaccccc  660
gacatcctgg agatcgagtt caagaagggc gtgcccgtga aggtgaccaa cgtgaaggac  720
ggcaccaccc accagaccag cctggagctg ttcatgtacc tgaacgaggt ggccggcaag  780
cacggcgtgg gccgcatcga catcgtggag aaccgcttca tcggcatgaa gagccgcggc  840
atctacgaga cccccgccgg caccatcctg taccacgccc acctggacat cgaggccttc  900
accatggacc gcgaggtgcg caagatcaag cagggcctgg gcctgaagtt cgccgagctg  960
gtgtacaccg gcttctggca cagccccgag tgcgagttcg tgcgccactg catcgccaag  1020
agccaggagc gcgtggaggg caaggtgcag gtgagcgtgc tgaagggcca ggtgtacatc  1080
ctgggccgcg agagccccct gagcctgtac aacgaggagc tggtgagcat gaacgtgcag  1140
ggcgactacg agcccaccga cgccaccggc ttcatcaaca tcaacagcct gcgcctgaag  1200
gagtaccacc gcctgcagag caaggtgacc gccaagtga                         1239

SEQ ID NO: 3            moltype = RNA  length = 4443
FEATURE                 Location/Qualifiers
misc_feature            1..4443
                        note = chemically synthesized oligonucleotide
source                  1..4443
                        mol_type = other RNA
                        organism = synthetic construct
SEQUENCE: 3
atgcaacgct ctcctcttga aaaggcctcg gtggtgtcca agctcttctt ctcgtggact  60
agacccatcc tgagaaaggg gtacagacag cgcttggagc tgtccgatat ctatcaaatc  120
ccttccgtgg actccgcgga caacctgtcc gagaagctcg agagagaatg ggacagagaa  180
ctcgcctcaa agaagaaccc gaagctgatt aatgcgctta ggcggtgctt tttctggcgg  240
ttcatgttct acggcatctt cctctacctg ggagaggtca ccaaggccgt gcagcccctg  300
ttgctgggac ggattattgc ctcctacgac cccgacaaca aggaagaaag aagcatcgct  360
atctacttgg gcatcggtct gtgcctgctt ttcatcgtcc ggaccctctt gttgcatcct  420
gctattttcg gcctgcatca cattggcatg cagatgagaa ttgccatgtt ttccctgatc  480
tacaagaaaa ctctgaagct ctcgagccgc gtgcttgaca agatttccat cggccagctc  540
gtgtccctgc tctccaacaa tctgaacaag ttcgacgagg gcctcgccct ggcccacttc  600
gtgtggatcg cccctctgca agtggcgctt ctgatgggcc tgatctggga gctgctgcaa  660
gcctcggcat tctgtgggct tggattcctg atcgtgctgg cactgttcca ggccggactg  720
```

-continued

```
gggcggatga tgatgaagta cagggaccag agagccggaa agatttccga acggctggtg  780
atcacttcgg aaatgatcga aaacatccag tcagtgaagg cctactgctg ggaagaggcc  840
atggaaaaga tgattgaaaa cctccggcaa accgagctga agctgacccg caaggccgct  900
tacgtgcgct atttcaactc gtccgctttc ttcttctccg ggttcttcgt ggtgtttctc  960
tccgtgctcc cctacgccct gattaaggga atcatcctca ggaagatctt caccaccatt  1020
tccttctgta tcgtgctccg catggccgtg acccggcagt tcccatgggc cgtgcagact  1080
tggtacgact ccctgggagc cattaacaag atccaggact tccttcaaaa gcaggagtac  1140
aagaccctcg agtacaacct gactactacc gaggtcgtga tggaaaacgt caccgccttt  1200
tgggaggagg gatttggcga actgttcgag aaggccaagc agaacaacaa caaccgcaag  1260
acctcgaacg gtgacgactc cctcttcttt tcaaacttca gcctgctcgg gacgcccgtg  1320
ctgaaggaca ttaacttcaa gatcgaaaga ggacagctcc tggcggtggc cggatcgacc  1380
ggagccggaa agacttccct gctgatggtg atcatgggag agcttgaacc tagcgaggga  1440
aagatcaagc actccggccg catcagcttc tgtagccagt tttcctggat catgcccgga  1500
accattaagg aaaacatcat cttcggcgtg tcctacgatg aataccgcta ccggtccgtg  1560
atcaaagcct gccagctgga agaggatatt tcaaagttcg cggagaaaga taacatcgtg  1620
ctgggcgaag ggggtattac cttgtcgggg ggccagcggg ctagaatctc gctggccaga  1680
gccgtgtata aggacgccga cctgtatctc ctggactccc ccttcggata cctggacgtc  1740
ctgaccgaaa aggagatctt cgaatcgtgc gtgtgcaagc tgatggctaa caagactcgc  1800
atcctcgtga cctccaaaat ggagcacctg aagaaggcag acaagattct gattctgcat  1860
gaggggtcct cctactttta cggcaccttc tcggagttgc agaacttgca gcccgacttc  1920
tcatcgaagc tgatgggttg cgacagcttc gaccagttct ccgccgaaag aaggaactcg  1980
atcctgacgg aaaccttgca ccgcttctct ttggaaggcg acgcccctgt gtcatggacc  2040
gagactaaga agcagagctt caagcagacc ggggaattcg gcgaaaagag gaagaacagc  2100
atcttgaacc ccattaactc catccgcaag ttctcaatcg tgcaaaagac gccactgcag  2160
atgaacggca ttgaggagga ctccgacgaa ccccttgaga ggcgcctgtc cctggtgccg  2220
gacagcgagc agggagaagc catcctgcct cggatttccg tgatctccac tggtccgacg  2280
ctccaagccc ggcggcggca gtccgtgctg aacctgatga cccacagcgt gaaccagggc  2340
caaaacattc accgcaagac taccgcatcc acccggaaag tgtccctggc acctcaagcg  2400
aatcttaccg agctcgacat ctactcccgg agactgtcgc aggaaaccgg gctcgaaatt  2460
tccgaagaaa tcaacgagga ggatctgaaa gagtgcttct tcgacgatat ggagtcgata  2520
cccgccgtga cgacttggaa cacttatctg cggtacatca ctgtgcacaa gtcattgatc  2580
ttcgtgctga tttggtgcct ggtgattttc ctggccgagg tcgcggcctc actggtggtg  2640
ctctggctgt tgggaaacac gcctctgcaa gacaagggaa actccacgca ctcgagaaac  2700
aacagctatg ccgtgattat cacttccacc tcctcttatt acgtgttcta catctacgtc  2760
ggagtggcgg ataccctgct cgcgatgggt ttcttcagag gactgccgct ggtccacacc  2820
ttgatcaccg tcagcaagat tcttcaccac aagatgttgc atagcgtgct gcaggccccc  2880
atgtccaccc tcaacactct gaaggccgga ggcattctga acagattctc caaggacatc  2940
gctatcctgg acgatctcct gccgcttacc atctttgact tcatccagct gctgctgatc  3000
gtgattggag caatcgcagt ggtggcggtg ctgcagcctt acattttcgt ggccactgtg  3060
ccggtcattg tggcgttcat catgctgcgg gcctacttcc tccaaaccag ccagcagctg  3120
aagcaactgg aatccgaggg acgatccccc atcttcactc accttgtgac gtcgttgaag  3180
ggactgtgga ccctccgggc tttcggacgg cagccctact tcgaaaccct cttccacaag  3240
gccctgaacc tccacaccgc caattggttc ctgtacctgt ccaccctgcg gtggttccag  3300
atgcgcatcg agatgatttt cgtcatcttc ttcatcgcgg tcacattcat cagcatcctg  3360
actaccggag agggagaggg acgggtcgga ataatcctga ccctcgccat gaacattatg  3420
agcaccctgc agtgggcagt gaacagctcg atcgacgtgg acagcctgat gcgaagcgtc  3480
agccgcgtgt tcaagttcat cgacatgcct actgagggaa aacccactaa gtccactaag  3540
ccctacaaaa atggccagct gagcaaggtc atgatcatcg aaaactccca cgtgaagaag  3600
gacgatattt ggccctccgg aggtcaaatg accgtgaagg acctgaccgc aaagtacacc  3660
gagggaggaa acgccattct cgaaaacatc agcttctcca tttcgccggg acagcgggtc  3720
ggccttctcg ggcggaccgg ttccgggaag tcaactctgc tgtcggcttt cctccggctg  3780
ctgaataccg agggggaaat ccaaattgac ggcgtgtctt gggattccat tactctgcag  3840
cagtggcgga aggccttcgg cgtgatcccc cagaaggtgt tcatcttctc gggtaccttc  3900
cggaagaacc tggatcctta cgagcagtgg agcgaccaag aaatctggaa ggtcgccgac  3960
gaggtcggcc tgcgctccgt gattgaacaa tttcctggaa agctggactt cgtgctcgtc  4020
gacgggggat gtgtcctgtc gcacggacat aagcagctca tgtgcctcgc acggtccgtg  4080
ctctccaagg ccaagattct gctgctggac gaaccttcgg cccacctgga tccggtcacc  4140
taccagatca tcaggaggac cctgaagcag gcctttgccg attgcaccgt gattctctgc  4200
gagcaccgca tcgaggccat gctggagtgc cagcagttcc tggtcatcga ggagaacaag  4260
gtccgccaat acgactccat tcaaaagctc ctcaacgagc ggtcgctgtt cagacaagct  4320
atttcaccgt ccgatagagt gaagctcttc ccgcatcgga acagctcaaa gtgcaaatcg  4380
aagccgcaga tcgcagcctt gaaggaagag actgaggaag aggtgcagga cacccggctt  4440
taa                                                                4443
```

```
SEQ ID NO: 4            moltype = RNA  length = 4443
FEATURE                 Location/Qualifiers
misc_feature            1..4443
                        note = chemically synthesized oligonucleotide
source                  1..4443
                        mol_type = other RNA
                        organism = synthetic construct
SEQUENCE: 4
atgcagcggt ccccgctcga aaaggccagt gtcgtgtcca aactcttctt ctcatggact  60
cggcctatcc ttagaaaggg gtatcggcag aggcttgagt tgtctgacat ctaccagatc  120
ccctcggtag attcggcgga taacctctcg gagaagctcg aacgggaatg ggaccgcgaa  180
ctcgcgtcta agaaaaaccc gaagctcatc aacgcactga gaaggtgctt cttctggcgg  240
ttcatgttct acggtatctt cttgtatctc ggggaggtca caaaagcagt ccaacccctg  300
ttgttgggtc gcattatcgc ctcgtacgac cccgataaca aagaagaacg gagcatcgcg  360
atctacctcg ggatcggact gtgtttgctt ttcatcgtca gaacactttt gttgcatcca  420
```

-continued

```
gcaatcttcg gcctccatca catcggtatg cagatgcgaa tcgctatgtt tagcttgatc  480
tacaaaaaga cactgaaact ctcgtcgcgg gtgttggata agatttccat cggtcagttg  540
gtgtccctgc ttagtaataa cctcaacaaa ttcgatgagg gactggcgct ggcacatttc  600
gtgtggattg ccccgttgca agtcgccctt ttgatgggcc ttatttggga gctgttgcag  660
gcatctgcct tttgtggcct gggatttctg attgtgttgg cattgtttca ggctgggctt  720
gggcggatga tgatgaagta tcgcgaccag agagcgggta aaatctcgga aagactcgtc  780
atcacttcgg aaatgatcga aaacatccag tcggtcaaag cctattgctg ggaagaagct  840
atggagaaga tgattgaaaa cctccgccaa actgagctga aactgacccg caaggcggcg  900
tatgtccggt atttcaattc gtcagcgttc ttcttttccg ggttcttcgt tgtctttctc  960
tcggttttgc cttatgcctt gattaagggg attatcctcc gcaagatttt caccacgatt  1020
tcgttctgca ttgtattgcg catggcagtg acacggcaat ttccgtgggc cgtgcagaca  1080
tggtatgact cgcttggagc gatcaacaaa atccaagact tcttgcaaaa gcaagagtac  1140
aagaccctgg agtacaatct tactactacg gaggtagtaa tggagaatgt gacggctttt  1200
tgggaagagg gttttggaga actgtttgag aaagcaaagc agaataacaa caaccgcaag  1260
acctcaaatg gggacgattc cctgtttttc tcgaacttct ccctgctcgg aacacccgtg  1320
ttgaaggaca tcaatttcaa gattgagagg ggacagcttc tcgcggtagc gggaagcact  1380
ggtgcgggaa aaactagcct cttgatggtg attatggggg agcttgagcc cagcgagggg  1440
aagattaaac actccgggcg tatctcattc tgtagccagt tttcatggat catgcccgga  1500
accattaaag agaacatcat tttcggagta tcctatgatg agtaccgata cagatcggtc  1560
attaaggcgt gccagttgga agaggacatt tctaagttcg ccgagaagga taacatcgtc  1620
ttgggagaag gggtattac attgtcggga gggcagcgag cgcggatcag cctcgcgaga  1680
gcggtataca aagatgcaga tttgtatctg cttgattcac cgtttggata cctcgacgta  1740
ttgacagaaa aagaaatctt cgagtcgtgc gtgtgtaaac ttatggctaa taagacgaga  1800
atcctggtga catcaaaaat ggaacacctt aagaaggcgg acaagatcct gatcctccac  1860
gaaggatcgt cctactttta cggcactttc tcagagttgc aaaacttgca gccggacttc  1920
tcaagcaaac tcatggggtg tgactcattc gaccagttca gcgcggaacg gcggaactcg  1980
atcttgacgg aaacgctgca ccgattctcg cttgagggtg atgccccggt atcgtggacc  2040
gagacaaaga agcagtcgtt taagcagaca ggagaatttg gtgagaaaag aaagaacagt  2100
atcttgaatc ctattaactc aattcgcaag ttctcaatcg tccagaaaac tccactgcag  2160
atgaatggaa ttgaagagga ttcggacgaa cccctggagc gcaggcttag cctcgtgccg  2220
gattcagagc aaggggaggc cattcttccc cggatttcgg tgatttcaac cggacctaca  2280
cttcaggcga ggcgaaggca atccgtgctc aacctcatga cgcattcggt aaaccagggg  2340
caaaacattc accgcaaaac gacggcctca acgagaaaag tgtcacttgc accccaggcg  2400
aatttgactg aactcgacat ctacagccgt aggctttcgc aagaaaccgg acttgagatc  2460
agcgaagaaa tcaatgaaga agatttgaaa gagtgtttct ttgatgacat ggaatcaatc  2520
ccagcggtga caacgtggaa cacatacttg cgttacatca cggtgcacaa gtccttgatt  2580
ttcgtcctca tctggtgtct cgtgatcttt ctcgctgagg tcgcagcgtc acttgtggtc  2640
ctctggctgc ttggtaatac gcccttgcaa gacaaaggca attctacaca ctcaagaaac  2700
aattcctatg ccgtgattat cacttctaca agctcgtatt acgtgtttta catctacgta  2760
ggagtggccg acactctgct cgcgatgggt ttcttccgag gactcccact cgttcacacg  2820
cttatcactg tctccaagat tctccaccat aagatgcttc atagcgtact gcaggctccc  2880
atgtccacct tgaatacgct caaggcggga ggtattttga atcgcttctc aaaagatatt  2940
gcaattttgg atgaccttct gcccctgacg atcttcgact tcatccagtt gttgctgatc  3000
gtgattgggg ctattgcagt agtcgctgtc ctccagcctt acatttttgt cgcgaccgtt  3060
ccggtgatcg tggcgtttat catgctgcgg gcctatttct tgcagacgtc acagcagctt  3120
aagcaactgg agtctgaagg gaggtcgcct atctttacgc atcttgtgac cagtttgaag  3180
ggattgtgga cgttgcgcgc ctttggcagg cagccctact ttgaaacact gttccacaaa  3240
gcgctgaatc tccatacggc aaattggttt ttgtatttga gtaccctccg atggtttcag  3300
atgcgcattg agatgatttt tgtgatcttc tttatcgcgg tgacttttat ctccatcttg  3360
accacgggag agggcgaggg acgggtcggt attatcctga cactcgccat gaacattatg  3420
agcactttgc agtgggcagt gaacagctcg attgatgtgg atagcctgat gaggtccgtt  3480
tcgagggtct ttaagttcat cgacatgccg acggagggaa agcccacaaa aagtacgaaa  3540
ccctataaga atgggcaatt gagtaaggta atgatcatcg agaacagtca cgtgaagaag  3600
gatgacatct ggcctagcgg gggtcagatg accgtgaagg acctgacggc aaaatacacc  3660
gagggaggga acgcaatcct tgaaaacatc tcgttcagca ttagccccgg tcagcgtgtg  3720
gggttgctcg ggaggaccgg gtcaggaaaa tcgacgttgc tgtcggcctt cttgagactt  3780
ctgaatacag agggtgagat ccagatcgac ggcgtttcgt gggatagcat caccttgcag  3840
cagtggcgga aagcgtttgg agtaatcccc caaaaggtct ttatctttag cggaaccttc  3900
cgaaagaatc tcgatcctta tgaacagtgg tcagatcaag agatttggaa agtcgcggac  3960
gaggttggcc ttcggagtgt aatcgagcag tttccgggaa aactcgactt tgtccttgta  4020
gatgggggat gcgtcctgtc gcatgggcac aagcagctca tgtgcctggc gcgatccgtc  4080
ctctctaaag cgaaaattct tctcttggat gaaccttcgg cccatctgga cccggtaacg  4140
tatcagatca tcagaaggac acttaagcag gcgtttgccg actgcacggt gattctctgt  4200
gagcatcgta tcgaggccat gctcgaatgc cagcaatttc ttgtcatcga agagaataag  4260
gtccgccagt acgactccat ccagaagctg cttaatgaga gatcattgtt ccggcaggcg  4320
atttcaccat ccgatagggt gaaacttttt ccacacagaa attcgtcgaa gtgcaagtcc  4380
aaaccgcaga tcgcggcctt gaaagaagag actgaagaag aagttcaaga cacgcgtctt  4440
taa                                                                4443
```

```
SEQ ID NO: 5            moltype = RNA  length = 1359
FEATURE                 Location/Qualifiers
misc_feature            1..1359
                        note = chemically synthesized oligonucleotide
source                  1..1359
                        mol_type = other RNA
                        organism = synthetic construct
SEQUENCE: 5
atgagcaccg ccgtgctgga gaaccccggc ctgggccgca agctgagcga cttcggccag  60
gagaccagct acatcgagga caactgcaac cagaacggcg ccatcagcct gatcttcagc  120
```

-continued

```
ctgaaggagg aggtgggcgc cctggccaag gtgctgcgcc tgttcgagga gaacgacgtg  180
aacctgaccc acatcgagag ccgccccagc cgcctgaaga aggacgagta cgagttcttc  240
acccacctgg acaagcgcag cctgcccgcc ctgaccaaca tcatcaagat cctgcgccac  300
gacatcggcg ccaccgtgca cgagctgagc cgcgacaaga agaaggacac cgtgccctgg  360
ttcccccgca ccatccagga gctggaccgc ttcgccaacc agatcctgag ctacggcgcc  420
gagctggacg ccgaccaccc cggcttcaag gaccccgtgt accgcgcccg ccgcaagcag  480
ttcgccgaca tcgcctacaa ctaccgccac ggccagccca tcccccgcgt ggagtacatg  540
gaggaggaga agaagacctg gggcaccgtg ttcaagaccc tgaagagcct gtacaagacc  600
cacgcctgct acgagtacaa ccacatcttc cccctgctgg agaagtactg cggcttccac  660
gaggacaaca tcccccagct ggaggacgtg agccagttcc tgcagacctg caccggcttc  720
cgcctgcgcc ccgtggccgg cctgctgagc agccgcgact tcctgggcgg cctggccttc  780
cgcgtgttcc actgcaccca gtacatccgc cacggcagca agcccatgta cacccccgag  840
cccgacatct gccacgagct gctgggccac gtgcccctgt tcagcgaccg cagcttcgcc  900
cagttcagcc aggagatcgg cctggccagc ctgggcgccc ccgacgagta catcgagaag  960
ctggccacca tctactggtt caccgtggag ttcggcctgt gcaagcaggg cgacagcatc  1020
aaggcctacg gcgccggcct gctgagcagc ttcggcgagc tgcagtactg cctgagcgag  1080
aagcccaagc tgctgcccct ggagctggag aagaccgcca tccagaacta caccgtgacc  1140
gagttccagc ccctgtacta cgtggccgag agcttcaacg acgccaagga gaaggtgcgc  1200
aacttcgccg ccaccatccc ccgccccttc agcgtgcgct acgaccccta cacccagcgc  1260
atcgaggtgc tggacaacac ccagcagctg aagatcctgg ccgacagcat caacagcgag  1320
atcggcatcc tgtgcagcgc cctgcagaag atcaagtaa                         1359
```